US012202782B2

(12) United States Patent
Dixon et al.

(10) Patent No.: US 12,202,782 B2
(45) Date of Patent: Jan. 21, 2025

(54) PROCESSES AND INTERMEDIATES FOR PREPARING MCL1 INHIBITORS

(71) Applicant: Gilead Sciences, Inc., Foster City, CA (US)

(72) Inventors: Darryl D. Dixon, San Mateo, CA (US); Michael A. Ischay, San Mateo, CA (US); Trevor C. Johnson, San Mateo, CA (US); Jeffrey E. Merit, San Mateo, CA (US); Christopher S. Regens, San Francisco, CA (US); Eric A. Standley, Foster City, CA (US); Dietrich P. Steinhuebel, San Francisco, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 17/528,532

(22) Filed: Nov. 17, 2021

(65) Prior Publication Data
US 2022/0177409 A1 Jun. 9, 2022

Related U.S. Application Data

(60) Provisional application No. 63/115,723, filed on Nov. 19, 2020.

(51) Int. Cl.
| | |
|---|---|
| *C07C 205/06* | (2006.01) |
| *C07C 49/255* | (2006.01) |
| *C07C 205/37* | (2006.01) |
| *C07C 211/45* | (2006.01) |
| *C07C 217/86* | (2006.01) |
| *C07C 255/54* | (2006.01) |
| *C07C 255/59* | (2006.01) |
| *C07C 317/22* | (2006.01) |
| *C07C 381/10* | (2006.01) |
| *C07D 209/48* | (2006.01) |
| *C07D 231/14* | (2006.01) |
| *C07D 267/12* | (2006.01) |
| *C07D 317/12* | (2006.01) |
| *C07D 317/24* | (2006.01) |
| *C07D 513/04* | (2006.01) |
| *C07D 513/08* | (2006.01) |

(52) U.S. Cl.
CPC .......... *C07C 205/06* (2013.01); *C07C 211/45* (2013.01); *C07D 267/12* (2013.01); *C07D 317/12* (2013.01); *C07D 513/04* (2013.01)

(58) Field of Classification Search
CPC ... C07C 205/06; C07C 205/37; C07C 211/45; C07C 217/86; C07C 255/54; C07C 255/59; C07C 43/1781; C07C 49/255; C07C 381/10; C07C 2601/04; C07D 267/12; C07D 317/12; C07D 317/22; C07D 317/24; C07D 513/04; C07D 513/08; C07D 209/48; C07D 231/14
See application file for complete search history.

(56) References Cited

U.S. PATENT DOCUMENTS

| | | | |
|---|---|---|---|
| 10,703,733 B2 | 7/2020 | Chu et al. | |
| 10,988,451 B2 | 4/2021 | Chu et al. | |
| 11,325,891 B2 | 5/2022 | Brak et al. | |
| 11,760,736 B2 | 9/2023 | Brak et al. | |
| 2015/0065738 A1 | 3/2015 | Yokoyama et al. | |
| 2016/0068545 A1 | 3/2016 | Brown et al. | |
| 2017/0088560 A1 | 3/2017 | Brown et al. | |
| 2018/0289720 A1 | 10/2018 | Harrington et al. | |
| 2019/0352271 A1 | 11/2019 | Chu et al. | |
| 2020/0331870 A1 | 10/2020 | Chu et al. | |
| 2021/0171543 A1 | 6/2021 | Chu et al. | |
| 2021/0179570 A1 | 6/2021 | Brak et al. | |
| 2022/0340535 A1 | 10/2022 | Chu et al. | |
| 2023/0013713 A1 | 1/2023 | Brak et al. | |

FOREIGN PATENT DOCUMENTS

| | | |
|---|---|---|
| WO | WO-1997/016430 A1 | 5/1997 |
| WO | WO-2016/033486 A1 | 3/2016 |
| WO | WO-2017/147410 A1 | 8/2017 |
| WO | WO-2018/183418 A1 | 10/2018 |
| WO | WO-2019/036575 A1 | 2/2019 |
| WO | WO-2019/046150 A1 | 3/2019 |
| WO | WO-2019/079578 A1 | 4/2019 |
| WO | WO-2019/173181 A1 | 9/2019 |
| WO | WO-2019/209667 A1 | 10/2019 |
| WO | WO-2019/222112 A1 | 11/2019 |
| WO | WO-2019/222266 A1 | 11/2019 |
| WO | WO-2019/222269 A1 | 11/2019 |
| WO | WO-2020/023657 A1 | 1/2020 |
| WO | WO-2020/097577 A1 | 5/2020 |
| WO | WO-2020/147802 A1 | 7/2020 |
| WO | WO-2021/005043 A1 | 1/2021 |
| WO | WO-2021/096860 A1 | 5/2021 |
| WO | WO-2021/108254 A1 | 6/2021 |
| WO | WO-2021/202452 A1 | 10/2021 |
| WO | WO-2021/225823 A1 | 11/2021 |
| WO | WO-2021/226168 A1 | 11/2021 |

(Continued)

OTHER PUBLICATIONS

Rombauts et al., 2021, caplus an 2021:114898.*
Invitation to Pay Additional Fees and Partial Search Report dated Mar. 10, 2022 for Intl. Appl. No. PCT/US2021/059648.
Intl. Search Report-Written Opinion dated May 3, 2022 for Intl. Appl. No. PCT/US2021/059648.
Office Action dated Jun. 30, 2022 for Taiwanese Appl. No. 110142990.
Notice of Allowance dated Oct. 13, 2022 for Taiwanese Appl. No. 110142990.
Non-Final Office Action dated Sep. 27, 2021 for U.S. Appl. No. 17/100,107.

(Continued)

*Primary Examiner* — Sun Jae Yoo

(57) ABSTRACT

The present disclosure relates to methods and intermediates for the synthesis of certain compounds that inhibit MCL1, for use in the treatment of cancers.

2 Claims, No Drawings

(56) References Cited

FOREIGN PATENT DOCUMENTS

| WO | WO-2021/250102 A1 | | 12/2021 |
|---|---|---|---|
| WO | WO-2022/008674 A1 | | 1/2022 |
| WO | WO-2022051317 A1 | * | 3/2022 |

OTHER PUBLICATIONS

Examination Report dated Oct. 18, 2023 for Australian Appl. No. 2021381769.

Notice of Allowance dated Nov. 6, 2023 for Taiwanese Appl. No. 111147005.

Office Action dated Mar. 28, 2024 for Chinese Appl. No. 202180077387.9.

Office Action dated Jun. 4, 2024 for Japanese Appl. No. 2023-530214.

Jones, J. et al. (1982) "Enzymes in organic synthesis. 26.Synthesis of enantiomerically pure grandisol from an enzyme-generated chiral synthon", Canadian Journal of Chemistry, 60(15):2007-2011.

Pichon, C. et al. (2000) "Enzymatic acylation of cyclobutene and cyclobutane meso-diols at low temperature", Tetrahedron: Asymmetry, 11(11):2429-2434.

Office Action dated Apr. 28, 2023 for Taiwanese Appl. No. 11114700.

Intl. Preliminary Report on Patentability dated Jun. 1, 2023 for Intl. Appl. No. PCT/US2021/059648.

* cited by examiner

PROCESSES AND INTERMEDIATES FOR PREPARING MCL1 INHIBITORS

CROSS REFERENCE TO RELATED APPLICATIONS

This application claims benefit under 35 U.S.C. § 119(e) to U.S. Provisional Application No. 63/115,723, filed Nov. 19, 2020, which is hereby incorporated herein by reference in its entirety for all purposes.

FIELD

The present disclosure relates to methods and intermediates for the synthesis of certain compounds which inhibit MCL1, for use in the treatment of cancers.

BACKGROUND

Apoptosis (programmed cell death) is a process for elimination of unwanted or potentially dangerous cells from an organism. Avoidance of apoptosis is critical for the development and sustained growth of tumors. Myeloid cell leukemia 1 protein (MCL1) is an antiapoptotic member of the Bcl-2 family of proteins. MCL1 is overexpressed in many cancers. Overexpression of MCL1 prevents cancer cells from undergoing apoptosis. Research has shown that MCL1 inhibitors can be used to treat cancers. Compounds that inhibit MCL1 have been disclosed, but there remains a need for synthetic methods for preparing such compounds on a manufacturing scale.

PCT Application No. PCT/US2019/032053 (Publication No. WO 2019/222112) discloses novel compounds useful as MCL1 inhibitors. This patent publication discloses that compounds according to Formula (I):

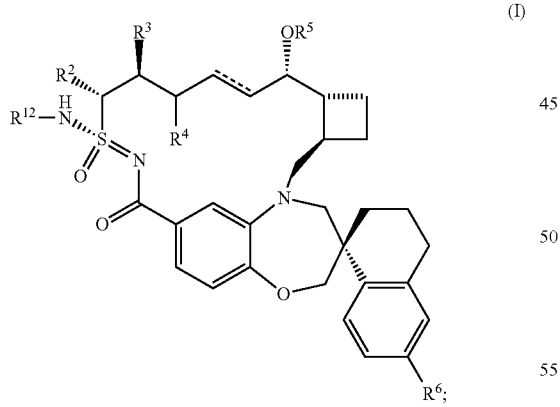

(I)

and pharmaceutically acceptable salts thereof, are effective as inhibitors of MCL1, and are useful in the treatment of cancers. Each of $R^2$, $R^3$, $R^4$, $R^5$, $R^6$ and $R^{12}$ are as defined in PCT/US2019/032053.

There is currently a need for synthetic methods and intermediates that can be used to prepare the compound of Formula (I) and salts thereof. There is also a need for methods for preparing intermediate compounds that can be used to prepare the compound of formula I and salts thereof.

BRIEF SUMMARY

In one embodiment, the present disclosure provides a method for preparing a compound 1:

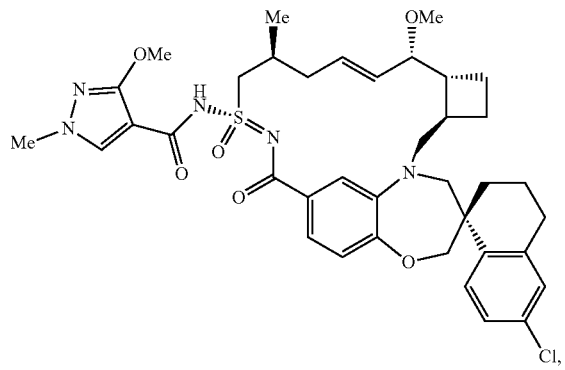

1 or a salt thereof, comprising preparing a compound of formula 9-A:

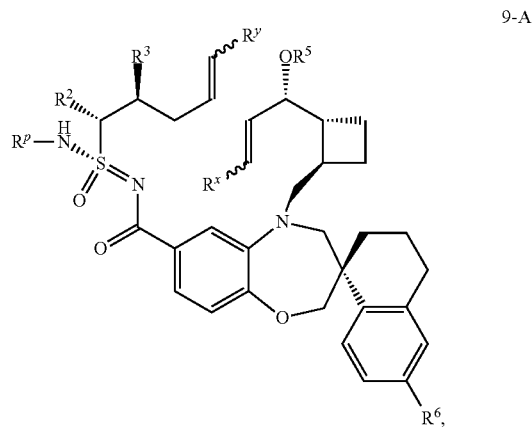

9-A by reacting a corresponding compound of formula 1-K:

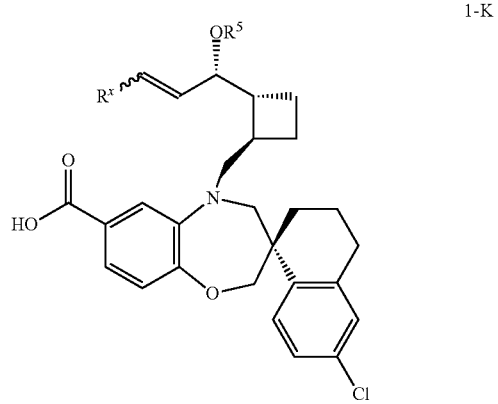

1-K with a corresponding compound of formula 6-L:

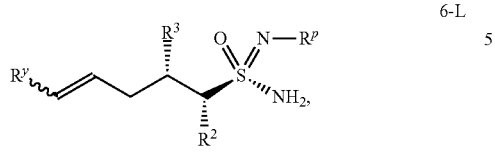

to provide the compound of formula 9-A or the salt thereof, wherein the compound of formula 1-K is prepared by converting a corresponding compound of formula 1-Q:

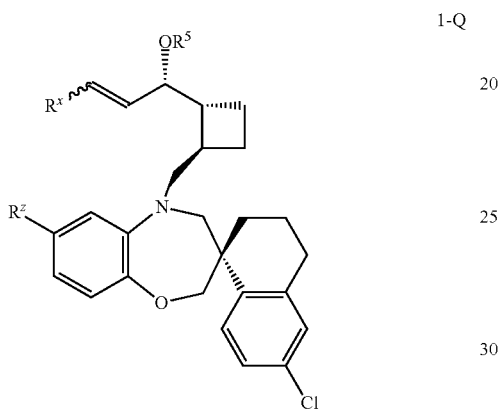

to the compound of formula 1-K or salt thereof, wherein $R^x$ and $R^y$ are each independently H or $C_{1-6}$alkyl; $R^2$ is H; $R^3$ and $R^5$ are each independently $CH_3$; $R^z$ is halogen or CN; and $R^p$ is selected from —C(=O)—$C_{1-6}$alkyl, —C(=O)—$C_{6-10}$aryl, —C(=O)—O—$C_{1-6}$alkyl, —C(=O)—O—$C_{1-6}$alkyl-$C_{6-10}$aryl, and —C(=O)—O—$C_{6-10}$aryl, wherein each aryl is optionally substituted with one to four groups independently selected from $C_{1-3}$alkyl and —O$C_{1-3}$alkyl.

In one embodiment, the present disclosure provides a method for preparing a compound of formula 1-Q:

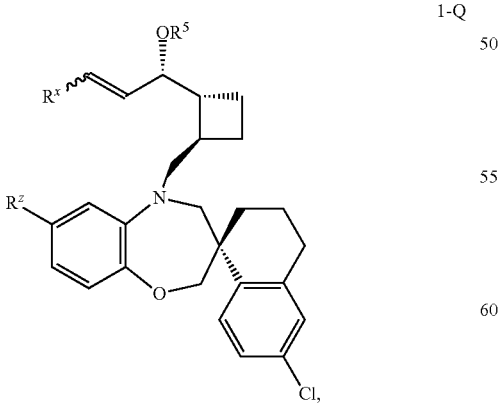

or a salt thereof, by reacting a corresponding compound of formula 1-P:

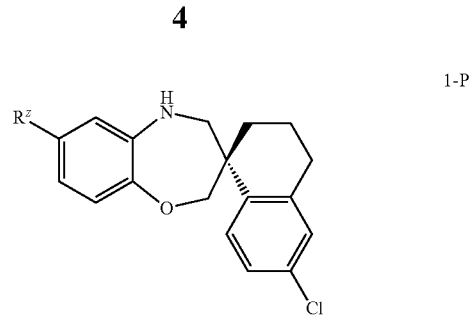

with a corresponding compound of formula 1-I:

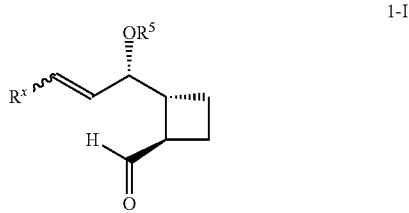

to provide the compound of formula 1-P.

In one embodiment, the present disclosure provides a method for preparing a compound of formula 1-P:

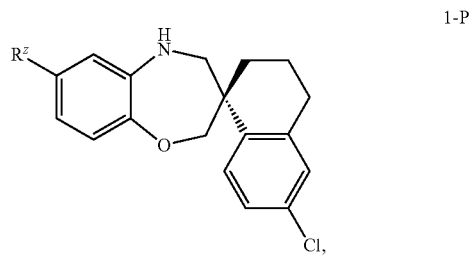

by converting a corresponding compound of formula 1-N:

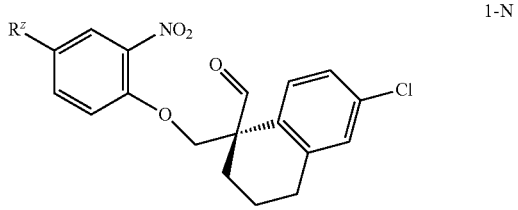

to the compound of formula 1-P, wherein the compound of formula 1-N is prepared by converting a corresponding compound of formula 1-M:

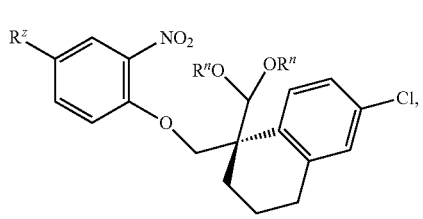

1-M to the compound of formula 1-N, wherein each $R''$ is independently $C_{1-6}$alkyl, or the two $R''$ moieties join together to form a $C_{2-4}$alkyl bridge, wherein the bridge is optionally substituted by one to four groups independently selected from $C_{1-3}$alkyl and phenyl.

In one embodiment, the present disclosure provides a method for preparing a compound 1:

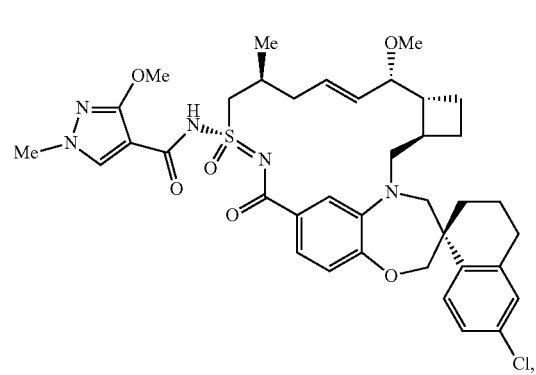

1 or a salt thereof, comprising preparing the compound of formula 1-K:

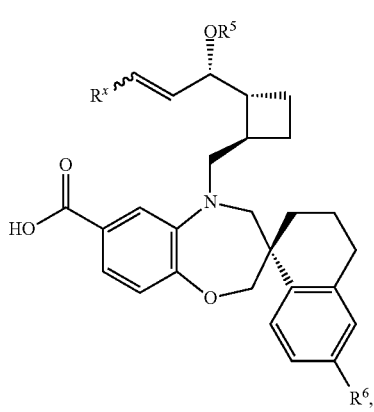

1-K by converting a corresponding compound of formula 2-L:

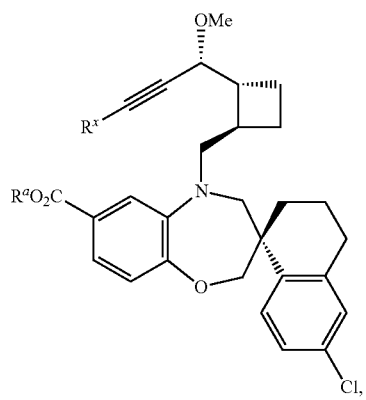

2-L to the compound of formula 1-K or the salt thereof, wherein $R^x$ is H or $C_{1-6}$alkyl; $R^5$ is $CH_3$; $R^6$ is Cl; and $R^a$ is $C_{1-6}$alkyl.

In one embodiment, the present disclosure provides a method for preparing a compound 1:

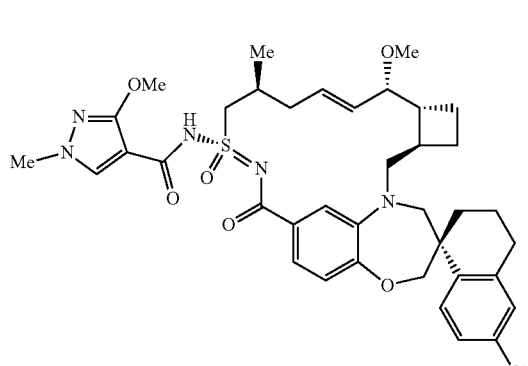

1 or a salt thereof, comprising preparing the compound of formula 1-K:

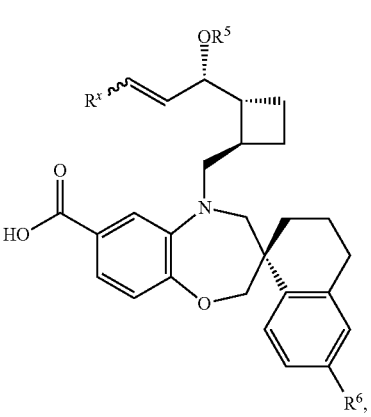

1-K by converting a corresponding compound of formula 3-H:

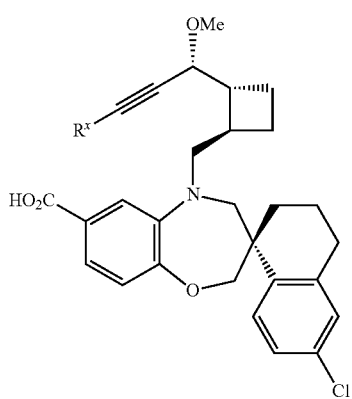

3-H

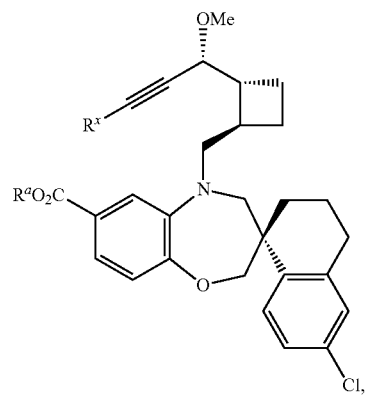

2-L to the compound of formula 1-K or the salt thereof, wherein $R^x$ is H or $C_{1-6}$alkyl; $R^5$ is $CH_3$; and $R^6$ is Cl.

In one embodiment, the present disclosure provides a method for preparing a compound of formula 3-H:

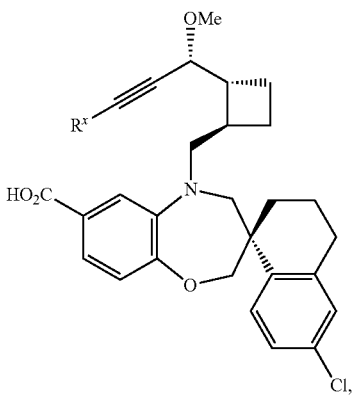

3-H by converting a corresponding compound of formula 2-L:

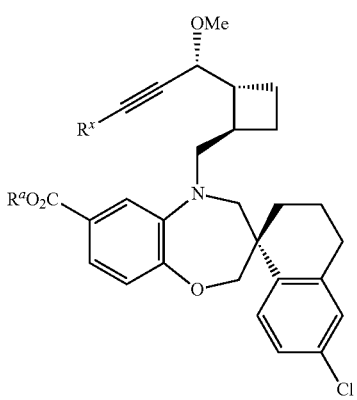

2-L to provide the compound of formula 3-H.

In one embodiment, the present disclosure provides a method for preparing a compound of formula 2-L:

by reacting a corresponding compound of formula 2-K:

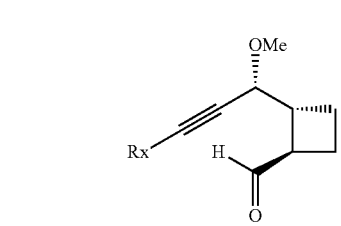

2-K with a compound of formula 5-I:

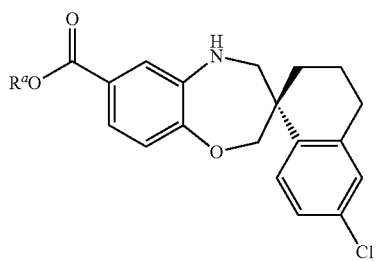

5-I to provide the compound of formula 2-L.

In one embodiment, the present disclosure provides a method for preparing a compound of formula 2-K:

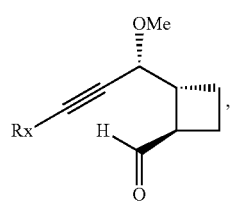

2-K by converting a corresponding compound of formula 2-H:

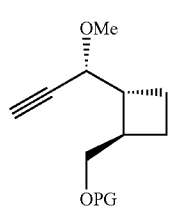
2-H to the compound of formula of 2-K, wherein the compound of formula 2-H is prepared by converting a corresponding compound of formula 2-G:

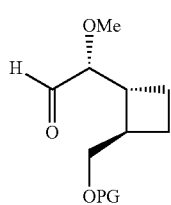
2-G to the compound of formula 2-H, wherein the compound of formula 2-G is prepared by converting a corresponding compound of formula 2-F:

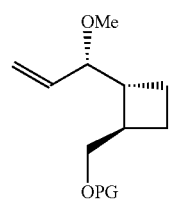
2-F to the compound of formula 2-G;
wherein PG is selected from a tri-$C_{1-6}$alkyl silyl group, a di-$C_{1-6}$alkyl-phenyl silyl group, a $C_{1-6}$alkyl-di-phenyl silyl group, and a tri-phenyl silyl group.

In one embodiment, the present disclosure provides a method for preparing a compound of formula 2-L:

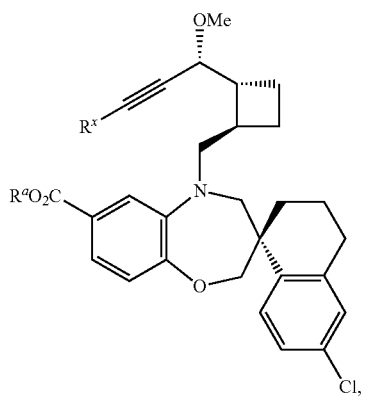
2-L by converting a corresponding compound of formula 3-G:

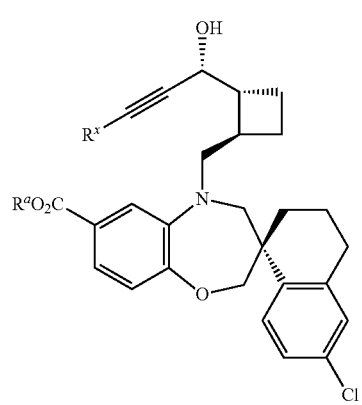
3-G to the compound of formula 2-L, wherein the compound of formula 3-G is prepared by reacting a corresponding compound of formula 3-E:

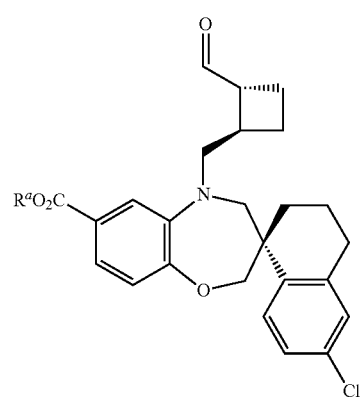
3-E with a compound:

to provide the compound of formula 3-E;
wherein $R^a$ is $C_{1-6}$alkyl.

In one embodiment, the present disclosure provides a method for preparing a compound 1:

or a salt thereof, comprising reacting a corresponding compound of formula 4-N:

[Structure of compound 1]

[Structure of compound 4-N]

or salt thereof, with a compound:

[Structure of 3-methoxy-1-methyl-1H-pyrazole-4-carboxylic acid]

to provide the compound 1 or the salt thereof, wherein the compound of formula 4-N is prepared by converting a corresponding compound of formula 4-M:

[Structure of compound 4-M]

to the compound of formula 4-N or the salt thereof, wherein $R^c$ is $C_{1-6}$alkyl.

In one embodiment, the present disclosure provides a method for preparing a compound of formula 4-M:

[Structure of compound 4-M]

or the salt thereof, by converting a corresponding compound of formula 4-L:

[Structure of compound 4-L]

or the salt thereof, to the compound of formula 4-M or the salt thereof, wherein the compound of formula 4-L is prepared by reacting a corresponding compound of formula 4-K:

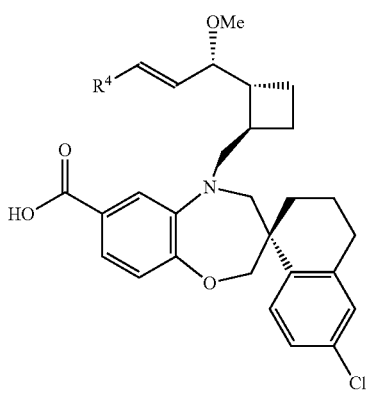

4-K with a corresponding compound of formula 4-J:

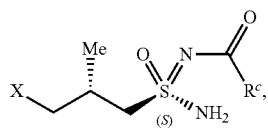

4-J or a salt thereof, to provide the compound of formula 4-L, wherein the compound of formula 4-J is prepared by converting a corresponding compound of formula 4-I:

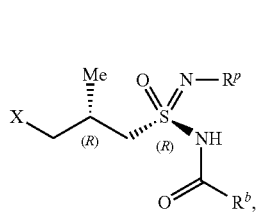

4-I or a salt thereof, to the compound of formula 4-J or the salt thereof, wherein $R^4$ is halogen or boronate, $R^b$ is $C_{1-6}$alkyl, $R^c$ is $C_{1-6}$alkyl, and $R^p$ is selected from —C(=O)—$C_{1-6}$alkyl, —C(=O)—$C_{6-10}$aryl, —C(=O)—O—$C_{1-6}$alkyl, —C(=O)—O—$C_{1-6}$alkyl-$C_{6-10}$aryl, and —C(=O)—O—$C_{6-10}$aryl, wherein each aryl is optionally substituted with one to four groups independently selected from $C_{1-3}$alkyl and —O$C_{1-3}$alkyl, X is halogen,

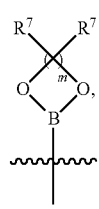

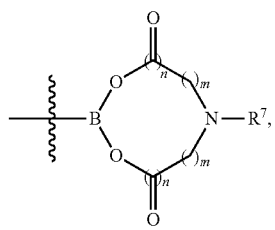

$C(O)_2R^1$, —$OS(O)_2R^2$, or —$OP(O)(R^2)_2$, wherein R is H or $C_{1-6}$alkyl, each $R^2$ is $C_{1-6}$alkyl or $C_{6-10}$aryl, each $R^7$ is independently H or $C_{1-3}$alkyl, wherein each alkyl or aryl is optionally substituted with one to four halogen or $C_{1-3}$alkyl, m is 1, 2, or 3, and n is 0 or 1.

In one embodiment, the present disclosure provides a method for preparing a compound of formula 4-I:

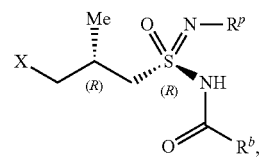

4-I or the salt thereof, by converting a corresponding compound of formula 4-H:

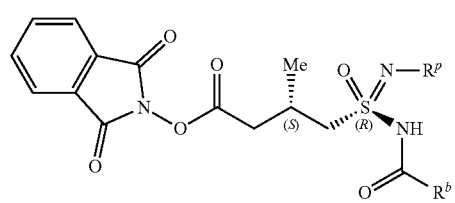

4-H to the compound of formula 4-I, wherein the compound of formula 4-H is prepared by converting a corresponding compound of formula 4-G:

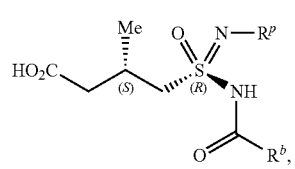

4-G or a salt thereof, to the compound of formula 4-H or the salt thereof.

In one embodiment, the present disclosure provides a method for preparing a compound of formula 4-G:

4-G

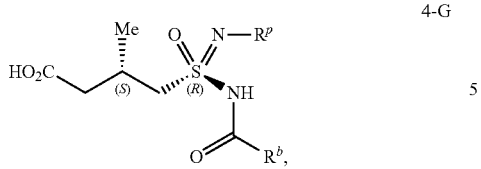

or the salt thereof, by converting a corresponding compound of formula 4-F:

4-F

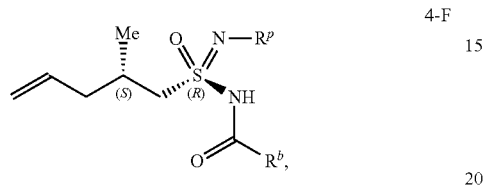

or a salt thereof, to the compound of formula 4-G or the salt thereof.

In one embodiment, the present disclosure provides a method for preparing a compound 1:

1

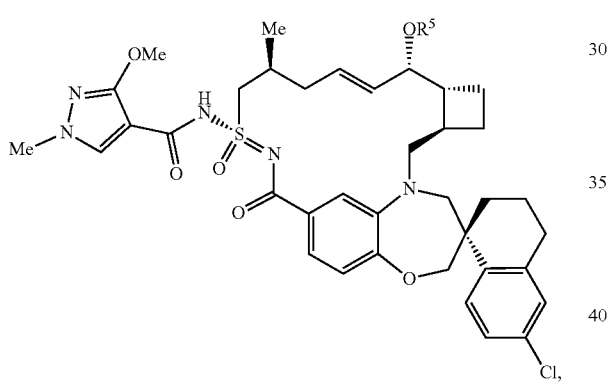

or a salt thereof, by converting a corresponding compound of formula 9-J:

9-J

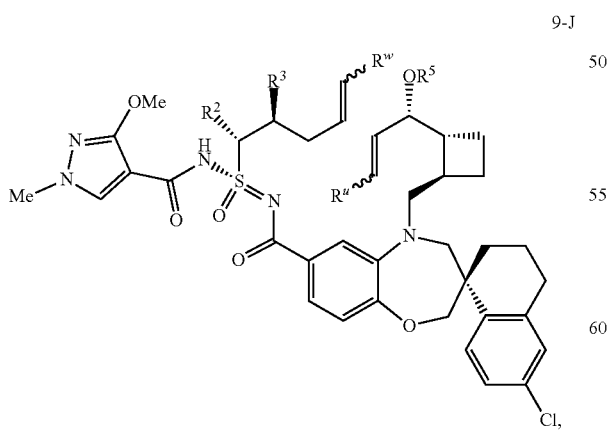

or a salt thereof, to the compound 1 or the salt thereof, wherein the compound of formula 9-J, or the salt thereof, is prepared by reacting a corresponding compound of formula 9-L:

9-L

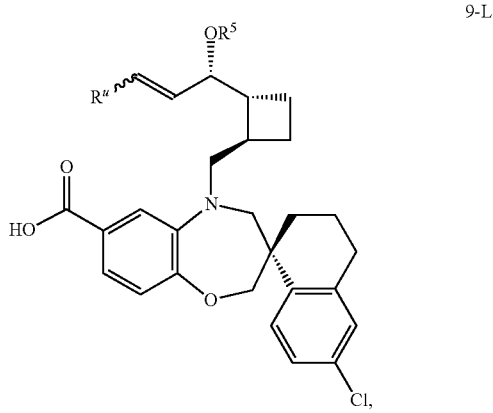

or a salt thereof, with a corresponding compound of formula 9-I:

P-I

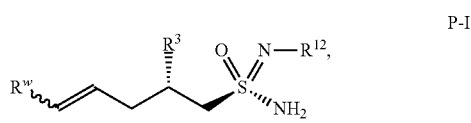

or a salt thereof, to provide the compound of formula 9-J or the salt thereof, wherein $R^u$ and $R^w$ are each independently H, $C_{1-6}$alkyl or $C_{6-10}$aryl; $R^2$ is H; $R^3$ and $R^5$ are each independently $CH_3$; and $R^{12}$ is

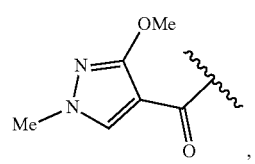

In one embodiment, the present disclosure provides a method for preparing a compound of formula 9-I:

P-I

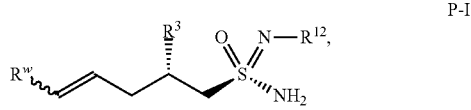

or a salt thereof, by converting a corresponding compound of formula 9-H:

9-H

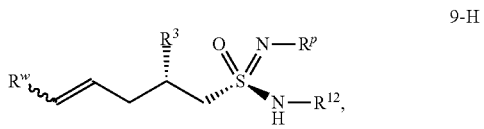

or a salt thereof, to the corresponding compound of formula 9-I, wherein the compound of formula 9-H, or the salt thereof, is prepared by reacting a corresponding compound of formula 9-G:

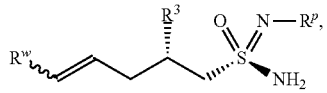

or a salt thereof, with a corresponding compound of formula 9-K:

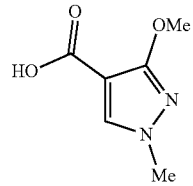

or a salt thereof, to provide the compound of formula 9-H or the salt thereof.

In one embodiment, the present disclosure provides a method of preparing a compound of formula 9-J:

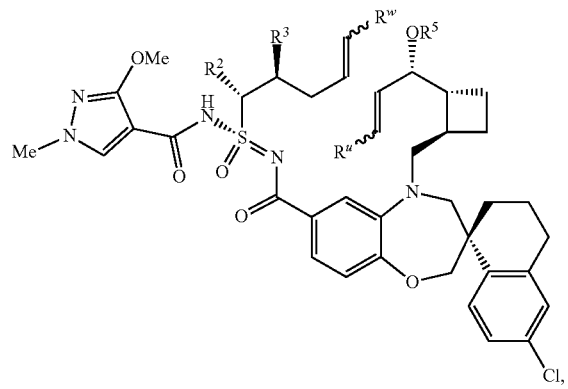

or a salt thereof, by reacting a corresponding compound of formula 9-L:

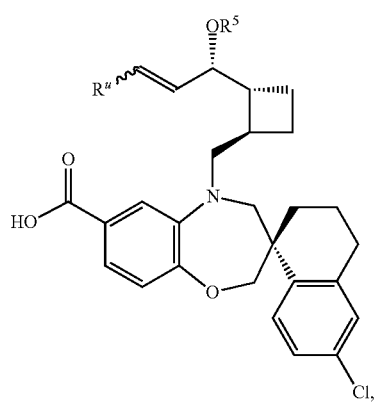

or a salt thereof, with a corresponding compound of formula 9-I:

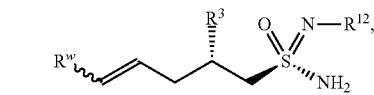

or a salt thereof, to provide the compound of formula 9-J or the salt thereof.

In one embodiment, the present disclosure provides a method of preparing a compound of formula 9-I:

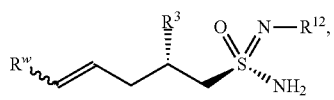

or a salt thereof, by converting a corresponding compound of formula 9-H:

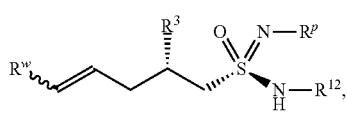

or a salt thereof, to the corresponding compound of formula 9-I.

In one embodiment, the present disclosure provides a method of preparing a compound of formula 9-H:

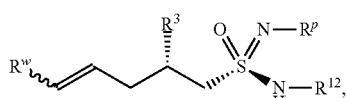

or a salt thereof, by reacting a corresponding compound of formula 9-G:

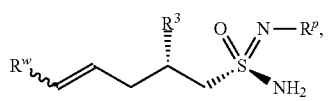

or a salt thereof, with a corresponding compound of formula 9-K:

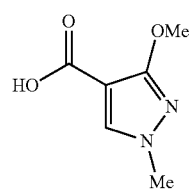

or a salt thereof, to provide the compound of formula 9-H or the salt thereof.

DETAILED DESCRIPTION

I. General

The present disclosure provides methods for preparing a compound 1 or a salt thereof. The present disclosure also provides methods for preparing compounds of Formula 1-M, 1-N, 1-O, 1-P, 1-Q, 1-R, 1-S, 2-G, 2-H, 2-I, 2-J, 2-K, 2-L, 1-J, 1-K, 3-F, 3-G, 2-L, 3-H, 4-G, 4-H, 4-I, 4-J, 4-L, 4-M, 4-N, 5-K, 5-L, 5-M, 5-N, 5-P, 5-Q, 6-M, 6-N, 7-C, 7-D, 7-E, 7-F, 8-B, 8-C, 8-D, 8-E, 8-F, and 9-A. The present disclosure also provides methods for preparing compounds of Formula 1-I, 5-D, 5-E, 9-H, 9-I, 9-J, 10-B, 10-C, 10-D, 10-E, 10-F, and 10-G.

II. Definitions

The abbreviations used herein have their conventional meaning within the chemical and biological arts.

The description set forth herein is made with the understanding that the present disclosure is to be considered as an exemplification of the claimed subject matter, and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading. Unless defined otherwise, all technical and scientific terms used herein have the same meaning as commonly understood by one of ordinary skill in the art.

When trade names are used herein, it is intended to independently include the tradename product and the active pharmaceutical ingredient(s) of the tradename product.

As used herein and in the appended claims, the singular forms "a" and "an", and "the" include plural referents unless the context clearly dictates otherwise. Thus, e.g., reference to "the compound" includes a plurality of such compounds and reference to "the assay" includes reference to one or more assays, and so forth.

A squiggly line " ∿∿ " that is between two chemical groups is used to indicate a mixture of isomers at this point.

"Isomers" are different compounds that have the same molecular formula. Isomers include stereoisomers, enantiomers and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. A mixture of enantiomers at a ratio other than 1:1 is a "scalemic" mixture.

"Diastereoisomers" or "diastereomers" are stereoisomers that have at least two asymmetric atoms, but which are not mirror-images of each other.

The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and/or hindered rotation about a bond axis and may thus give rise to enantiomers, diastereomers, and other stereoisomeric forms that may be defined, in terms of absolute stereochemistry, as (R)- or (S)-. The present disclosure is meant to include all such possible isomers, including racemic mixtures, scalemic mixtures, diastereomeric mixtures, optically pure forms and intermediate mixtures. Optically active (R)- and (S)-isomers may be prepared using chiral synthons or chiral reagents, or resolved using conventional techniques.

Except as expressly defined otherwise, the present disclosure includes all tautomers of compounds detailed herein, even if only one tautomer is expressly represented (e.g., both tautomeric forms are intended and described by the presentation of one tautomeric form where a pair of two tautomers may exist). For example, if reference is made to a compound containing an amide (e.g., by structure or chemical name), it is understood that the corresponding imidic acid tautomer is included by this disclosure and described the same as if the amide were expressly recited either alone or together with the imidic acid. Where more than two tautomers may exist, the present disclosure includes all such tautomers even if only a single tautomeric form is depicted by chemical name and/or structure.

Compounds described herein may have chiral centers and/or geometric isomeric centers (E- and Z-isomers), and it is to be understood that all such optical, enantiomeric, diastereoisomeric and geometric isomers are encompassed. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s).

In some embodiments disclosed herein, a catalyst used for a reaction may be an "asymmetric" or catalyst. The term "asymmetric catalyst" as used herein refers to a catalyst that promotes the enantioselective and/or diastereoselective transformation of an achiral center or molecule into a chiral center or molecule, respectively. For example, an asymmetric catalyst may generate an enantiomeric excess of a product. Exemplary asymmetric catalysts comprise a transition metal and a chiral ligand. Non-limiting examples of chiral ligands include BINAP/SEGPHOS®, salens, bisoxazolines, tartrate ligands, cinchona alkaloids, DuPhos phospholanes, BPE phospholanes, DSM phosphoramidites, Solvias® Josiphos families, phosphine-oxazolines, the Reetz and Trost ligands, and ChiralQuest phosphines.

Also provided are pharmaceutically acceptable hydrates, solvates, co-crystals, tautomeric forms, polymorphs, and prodrugs of the compounds described herein.

The term "hydrate" refers to the complex formed by the combining of a compound of Formula I, or any Formula disclosed herein, and water.

The term "solvate" refers to a complex formed by the combining of a compound of Formula I, or any other Formula as disclosed herein, and a solvent or a crystalline solid containing amounts of a solvent incorporated within the crystal structure. As used herein, the term "solvate" includes hydrates.

Any formula or structure given herein, or any Formula disclosed herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes compounds of Formula A or Formula I or Formula I(a), or any Formula disclosed herein, in which from 1 to "n" hydrogens attached to a carbon atom is/are replaced by deuterium, in which n is the number of hydrogens in the molecule. Such compounds may exhibit increased resistance to metabolism and thus may be useful for increasing the half-life of any compound of Formula I when administered to a mammal. See, for example, Foster, "Deuterium Isotope Effects in Studies of Drug Metabolism", *Trends Pharmacol. Sci.* 5(12):524-527 (1984). Such compounds are synthesized by means well known in the art, for example by employing starting materials in which one or more hydrogen atoms have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life or reduced dosage requirements. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the Formula I, or any Formula disclosed herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

The modifier "about" used in connection with a quantity is inclusive of the stated value and has the meaning dictated by the context (e.g., includes the degree of error associated with measurement of the particular quantity). Absent any other definition or any context to the contrary, the term about may be interpreted as ±10%, ±5%, or ±3%, or ±2%, or ±1%.

The term "chiral" refers to molecules which have the property of non-superimposability of the mirror image partner, and the term "achiral" refers to molecules which are superimposable on their mirror image partner.

A prefix such as "$C_{u-v}$" or ($C_u$-$C_v$) indicates that the following group has from u to v carbon atoms, where u and v are integers. For example, "$C_{1-6}$alkyl" indicates that the alkyl group has from 1 to 6 carbon atoms.

A dash ("-" or "—") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. Unless chemically or structurally required, no directionality is indicated or implied by the order in which a chemical group is written or named.

A squiggly line on a chemical group as shown below, for example,

indicates a point of attachment, i.e., it shows the broken bond by which the group is connected to another described group.

The term "substituted" or "optionally substituted" means that one or more hydrogen atoms on a carbon atom (either aliphatic or aromatic) is replaced with one or more atoms or groups other than hydrogen, provided that the designated carbon atom's normal valence is not exceeded. A "substituent" is an atom or group that replaces a hydrogen atom on a carbon when it is "substituted." Unless specified otherwise, where a group is described as optionally substituted, any substituents of the group are themselves unsubstituted. The term "optionally substituted," if not otherwise modified, includes at least the following optional substituents: halogen, hydroxy, amino, thiol, $C_{1-6}$alkyl, $C_{1-6}$haloalkyl, $C_{2-6}$alkynyl, $C_{3-10}$cycloalkyl, $C_{6-10}$aryl, 3-12 membered heterocycloalkyl, and 5-10 membered heteroaryl, —OC$_{1-6}$alkyl, —C(O)—C$_{1-6}$alkyl, —C(O)O—C$_{1-6}$alkyl, —C(O)—OH, —C(O)—NH$_2$, —C(O)N(C$_{1-6}$alkyl)(C$_{1-6}$alkyl), —C(O)NH(C$_{1-6}$alkyl)-OC(O)N(C$_{1-6}$alkyl)(C$_{1-6}$alkyl), OC(O)NH(C$_{1-6}$alkyl), —N(C$_{1-6}$alkyl)(C$_{1-6}$alkyl), —NH(C$_{1-6}$alkyl), —N(C$_{1-6}$alkyl)-C(O)—(C$_{1-6}$alkyl), NH—C(O)—(C$_{1-6}$alkyl), —N(C$_{1-6}$alkyl)-C(O)O—(C$_{1-6}$alkyl), —S(O)$_2$NH$_2$, —S(O)$_{(1\ or\ 2)}$(C$_{1-6}$alkyl), —S(O)$_2$N(C$_{1-6}$alkyl)(C$_{1-6}$alkyl), —N(C$_{1-6}$alkyl)S(O)$_2$R$^b$, —N$_3$, —CN, and —NO$_2$.

As used herein, "alkyl" is a linear or branched saturated monovalent hydrocarbon. Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), and 2,3-dimethyl-2-butyl (—C(CH$_3$)$_2$CH(CH$_3$)$_2$), 3,3-dimethyl-2-butyl (—CH(CH$_3$)C(CH$_3$)$_3$. Whenever any alkyl group may exist in more than one isomeric form, for example n-butyl, sec-butyl, and tert-butyl, any reference herein that lacks a prefix, e.g., "butyl", should be interpreted as the normal isomer (e.g., "n-butyl"). Thus, "propyl" means "n-propyl," and "butyl" means "n-butyl."

"Alkenyl" refers to an aliphatic group containing at least one carbon-carbon double bond. Examples of alkenyl groups include ethenyl, propenyl, butadienyl (including 1,2-butadienyl, and 1,3-butadienyl).

"Alkoxy" as used herein refers to a radical of the formula —OR$_A$ where R$_A$ is an alkyl radical as defined above. Non-limiting examples of alkoxy include methoxy, ethoxy, propoxy, and butoxy.

"Alkynyl" refers to an aliphatic group containing at least one carbon-carbon triple bond.

"Aryl" refers to a monoradical or diradical aromatic carbocyclic group having a single ring (e.g., monocyclic) or multiple rings (e.g., bicyclic or tricyclic) including fused ring systems wherein one or more fused rings is/are fully or partially unsaturated. Non-limiting examples of aryl groups as used herein include phenyl, naphthyl, fluorenyl, indanyl, tetrahydroindanyl, and anthryl. Aryl, however, does not encompass or overlap in any way with heteroaryl defined below. If one or more aryl groups are fused with a heteroaryl ring, the resulting ring system is heteroaryl. The classification of mono or diradical indicates whether the aryl group terminates the chain (monoradical) or is within a chain (diradical). The above definition does not preclude additional substituents on the aryl group. For example, as used herein, the aryl group in "A-aryl-B" is a diradical whereas the aryl group in "A-B-aryl" is monoradical, though additional substituents may be present on each aryl group.

The term "aryloxy" refers to the group —O-aryl.

"Cycloalkyl" refers to a saturated or partially saturated cyclic alkyl group having a single ring or multiple rings including fused, bridged, and spiro ring systems. Examples of cycloalkyl groups include cyclopropyl, cyclobutyl, cyclopentyl, and cyclohexyl. "Cycloalkyl" does not include any rings containing heteroatoms in the ring.

"Halo" and "halogen" are used herein to refer to fluoro (—F), chloro (—Cl), bromo (—Br) and iodo (—I).

When the prefix "halo" is appended to another term it refers to any one or more of the hydrogen associated with that term being independently replaced by a halogen atom. Thus, the term "haloalkyl" as used herein refers to an alkyl as defined herein, wherein one or more hydrogen atoms of the alkyl are independently replaced by a halogen substituent, which may be the same or different. For example, C$_{1-6}$haloalkyl (or haloC$_{1-6}$alkyl) is a C$_{1-6}$alkyl wherein one or more of the hydrogen atoms of the C$_{1-6}$alkyl have been replaced by a halo substituent. Examples of haloalkyl groups include, but are not limited to, fluoromethyl, fluorochloromethyl, difluoromethyl, difluorochloromethyl, trifluoromethyl, 1,1,1-trifluoroethyl, and pentafluoroethyl. Up to all hydrogen atoms of the associated term may be replaced by halogen, thus resulting in a perfluorinated substituent (e.g., perfluoroalkyl).

"Heteroaryl" refers to a monoradical or diradical aromatic group having a single ring, multiple rings, or multiple fused rings, with one or more ring heteroatoms independently selected from nitrogen, oxygen, and sulfur. The heteroatoms within the "heteroaryl" may be oxidized, e.g., —N(O)—, —S(O)—, —S(O)$_2$—. The term includes fused ring systems wherein one or more fused rings is/are fully or partially unsaturated. The classification of mono or diradical indicates whether the heteroaryl group terminates the chain (monoradical) or is within a chain (diradical). The above definition does not preclude additional substituents on the heteroaryl group. For example, the heteroaryl group in "A-heteroaryl-B" is a diradical whereas the heteroaryl group in "A-B-heteroaryl" is monoradical, though additional substituents may be present on each heteroaryl group. Heteroaryl does not encompass or overlap with aryl as defined above. Non-limiting examples of heteroaryl groups include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl.

The term "heteroaryloxy" refers to the group —O-heteroaryl.

The term "heterocyclyl," "heterocycle," or "heterocyclic" or "heterocycloalkyl" refers to a monoradical or diradical saturated or unsaturated group having a single ring or multiple condensed rings having one or more heteroatoms selected from nitrogen, sulfur, phosphorus, and/or oxygen within the ring. The heteroatoms within the "heterocyclyl" may be oxidized, e.g. —N(O)—, —S(O)—, —S(O)$_2$—. A heterocyclyl may be a single ring or multiple rings wherein the multiple rings may be fused, bridged, or spiro. Any non-aromatic ring containing at least one heteroatom is considered a heterocyclyl, regardless of the attachment (i.e., can be bound through a carbon atom or a heteroatom). Exemplary heterocyclic groups include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, thietanyl, trithianyl, tetrahydropyranyl, thiomorpholinyl, thiamorpholinyl, 1-oxo-thiomorpholinyl, and 1,1-dioxo-thiomorpholinyl.

The term "cyano" refers to the group —CN.

The term "oxo" refers to a group =O.

The term "carboxy" refers to a group —C(O)—OH.

The term "dioxane" refers to "1,4-dioxane."

Compounds described herein may be prepared and/or formulated as pharmaceutically acceptable salts. Pharmaceutically acceptable salts are non-toxic salts of a free base form of a compound that possesses the desired pharmacological activity of the free base. These salts may be derived from inorganic or organic acids or bases. For example, a compound that contains a basic nitrogen may be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington: The Science and Practice of Pharmacy, 21$^{st}$ Edition, Lippincott Williams and Wilkins, Philadelphia, Pa., 2006.

Non-limiting examples of "pharmaceutically acceptable salts" of the compounds disclosed herein also include salts derived from an appropriate base, such as an alkali metal (for example, sodium, potassium), an alkaline earth metal (for example, magnesium), ammonium and $NY_4^+$ (wherein Y is $C_1$-$C_4$ alkyl). Also included are base addition salts, such as sodium or potassium salts.

The terms "nonpolar," "polar aprotic," and "polar protic" as used herein to refer to solvents, is intended as a means of classifying solvents for use in the various methods and steps described herein. For the purposes of classification herein, the term "nonpolar solvent" means any ethereal solvent, hydrocarbon solvent or halogenated solvent, carbon dioxide, and carbon disulfide, as well as other solvents traditionally classified as nonpolar solvents. Ethereal solvents include dimethyl ether, diethyl ether, dipropyl ether, diisopropyl ether, dibutyl ether, methyl isopropyl ether, methyl t-butyl ether, cyclopentyl methyl ether, tetrahydrofuran, 2-methyltetrahydrofuran, 1,4-dioxane, 1,2-dimethoxyethane, diethylene glycol diethyl ether, triethylene glycol dimethyl ether, and anisole. Hydrocarbon solvents include petroleum ether, pentane (or mixed pentanes), heptane (or mixed heptanes), hexane (or mixed hexanes), octane, isooctane, decane, dodecane, cyclopentane, cyclohexane, methylcyclohexane, benzene, toluene, o-xylene, m-xylene, p-xylene, pyridine, chlorobenzene, 1,2-dichlorobenzene, fluorobenzene, phenol, anisole, trifluorotoluene, hexachlorobenzene, hexafluorobenzene, and benzonitrile. Halogenated solvents include dichloromethane, tetrachloromethane, chloroform, 1,1-dichloroethane, 1,1,1,-trichloroethane, vinyl chloride, vinylidene dichloride, trichloroethylene, perchloroethylene, chlorobenzene, 1,2-dichlorobenzene, fluorobenzene, trifluorotoluene, hexachlorobenzene, and hexafluorobenzene. For the purposes of classification herein, the term "polar aprotic solvent" means any ester, nitrile, or ketone solvent, as well as N,N-dimethylformamide, N,N-dimethylacetamide, dimethylsulfoxide, sulfolane, N-methyl-2-pyrrolidinone, N,N-dimethylethyleneurea, N,N-dimethylpropyleneurea, hexamethylphosphoric acid triamide, dimethyl carbonate, diethyl carbonate, ethylene carbonate, propylene carbonate, and nitromethane, as well as other solvents traditionally classified as polar protic solvents. Ester solvents include methyl acetate, ethyl acetate, propyl acetate, isopropyl acetate, butyl acetate, isobutyl acetate, t-butyl acetate, vinyl acetate, 2,2, 2-trichloroethyl acetate, and 2-ethoxyethyl acetate. Nitrile solvents include acetonitrile, propionitrile, and benzonitrile. Ketone solvents include acetone, methyl ethyl ketone, methyl n-butyl ketone, methyl isobutyl ketone, methyl t-butyl ketone, 3-pentanone, cyclopentanone, cyclohexanone, and 2,5-hexanedione. For the purposes of classification herein, the term "polar protic solvents" means any alcohol or acid solvent, or water, or ammonia, as well as other solvents traditionally classified as polar protic solvents. Alcohol solvents include methanol, ethanol, n-propanol, isopropanol, n-butanol, isobutanol, sec-butanol, tert-butanol, pentanol, 3-methyl-1-butanol, cyclopentanol, cyclohexanol, phenol, 2-methyoxyethanol, 2-ethoxyethanol, ethylene glycol, 1,2-propylene glycol, 1,3-propylene glycol, glycerol, 1,4,-butanediol, and 1,4-cyclohexanediol. Acid solvents include formic acid, acetic acid, trichloroacetic acid, and trifluoroacetic acid.

"Salt" refers to acid or base salts of the compounds used in the methods of the present disclosure. Salts useful in the present disclosure include, but are not limited to, hemisulfate, sulfate, chloride, bromide, carbonate, nitrate, and acetate salts. A hemisulfate salt refers a compound in which only one of two basic groups is formed a salt with sulfuric acid. A carbonate salt includes a hydrogencarbonate (or bicarbonate) salt. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

II. Methods of Preparing Compounds

The present disclosure includes several methods of preparing the compound 1.

A. Method of Preparing Compound 1 from Formula 1-L and Formula 5-E

In one embodiment, the present disclosure provides a method of making a compound selected from 1-M. 1-N, 1-O, 1-P, 1-Q, 1-R, 1-S, 1-K, 9-A and compound 1, as shown in Scheme 1, wherein $R^x$ and $R^y$ are independently H, $C_{1-6}$alkyl, or $C_{6-10}$aryl, wherein the alkyl is optionally substituted with $C_{6-10}$aryl, $R^2$ is H, $R^3$ is methyl, $R^5$ is methyl, $R^z$ is halo or CN, each $R''$ is independently $C_{1-6}$alkyl, or the two $R''$ moieties join together to form a $C_{2-4}$alkyl bridge, wherein the bridge is optionally substituted by one to four groups independently selected from $C_{1-3}$alkyl and phenyl, and $R^p$ is selected from —C(=O)—$C_{1-6}$alkyl, —C(=O)-heteroaryl, —C(=O)—O—$C_{1-6}$alkyl, and —C(=O)—O—$C_{1-6}$alkyl-$C_{6-10}$aryl, wherein each aryl or heteroaryl is optionally substituted with one to four groups independently selected from $C_{1-3}$alkyl and —$OC_{1-3}$alkyl, wherein each heteroaryl has one to four heteroatoms; wherein each heteroatom is independently selected from N, O, and S, and wherein each heteroaryl has 5 to 10 ring members. In one embodiment, $R^z$ is Br. In one embodiment, $R^z$ is CN. In one embodiment, $R''$ is methyl. In one embodiment, $R^z$ is Br, and $R''$ is methyl. In one embodiment, $R^z$ is CN, and $R''$ is methyl. In one embodiment, $R^x$ is methyl. In one embodiment, $R^x$ is H. In one embodiment, two $R''$ moieties join together to form a cyclic acetal. In one embodiment, two $R''$ moieties join together to form a bridge selected from $CH_2CH_2$—, —$CH(CH_3)CH(CH_3)$—, —$CH_2CH(CH_3)$—, —$CH_2CH(C_6H_5)$—, —$C(CH_3)_2C(CH_3)_2$—, —$CH_2CH_2CH_2$—, —$CH_2CBr_2CH_2$—, —$CH_2(C=CH)CH_2$—, —$CH_2CH(C_6H_5)CH_2$—, —$CH(CH_3)CH_2CH(CH_3)$—, —$CH_2CH(CH_3)CH_2$—, —$CH_2C(CH_3)_2CH_2$—, —$CH_2C(CH_2CH_3)_2CH_2$—, —$CH_2CH_2CH_2CH_2$—, —CH$_2$CH$_2$CH$_2$CH$_2$CH$_2$—, —CH(C$_6$H$_5$)CH(C$_6$H$_5$), —CH$_2$CH(C$_6$H$_5$)CH$_2$—, and -(o-C$_6$H$_4$)—. In one embodiment, two R″ moieties join together to form —C(CH$_3$)$_2$C(CH$_3$)$_2$—.

Scheme 1
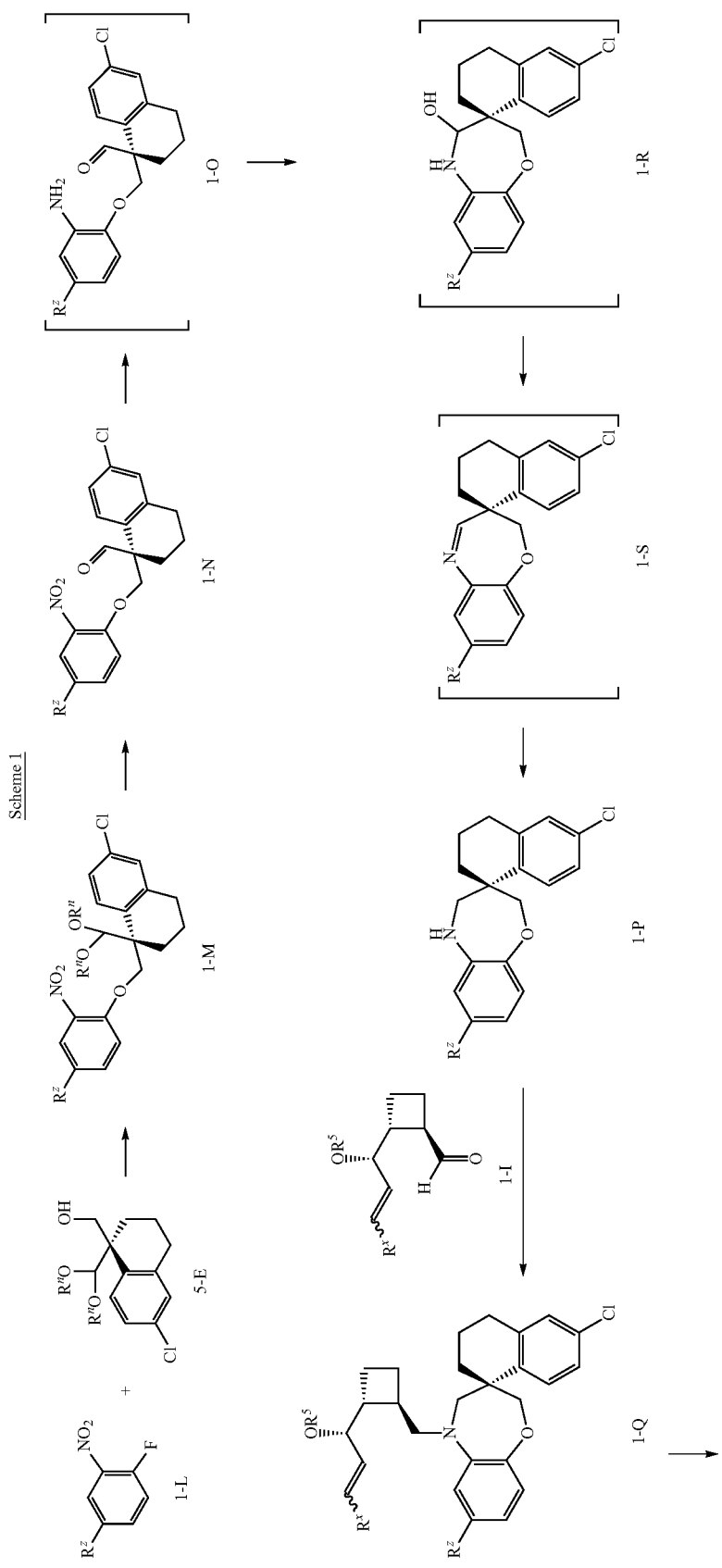

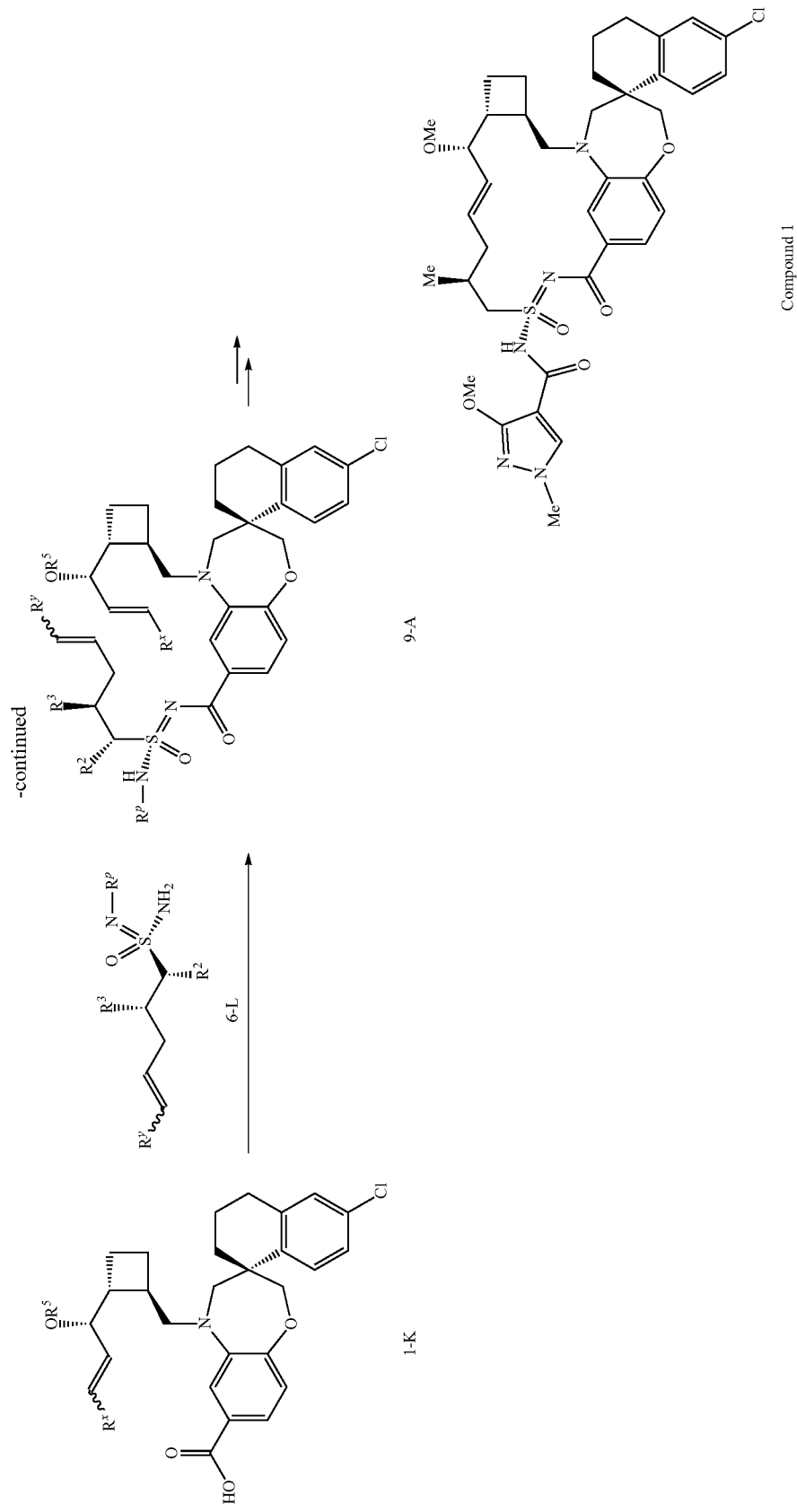

In one embodiment, the present disclosure provides a method to prepare a compound 1-M from a compound 1-L and a compound 5-E.

In one embodiment, the method comprises the step of reacting a compound 1-L with a compound 5-E, a base in a suitable solvent, for a time and under conditions effective to form a compound 1-M. In one embodiment, a promoter is present.

In one embodiment, the base is selected from inorganic bases (lithium carbonate, sodium carbonate, potassium carbonate, potassium tert-butoxide, calcium carbonate, potassium phosphate, sodium phosphate), metal hydrides such as sodium and potassium; alkoxides such as sodium methoxide, sodium tert-butoxide, or lithium tert-butoxide, or tert-pentoxide analogs, alkali amide bases such as lithium, sodium and potassium hexamethyldisilazane and lithium diisopropylamide. In one embodiment, the base is potassium tert-butoxide.

In one embodiment, the promoter is selected from NaI and tetrabutylammonium iodide.

In one embodiment, the solvent is selected from ethers (e.g., 2-methyltetrahydrofuran, tert-butyl methyl ether (MTBE), cyclopentyl methyl ether (CPME), tetrahydrofuran (THF)), polar aprotic solvents (e.g., dimethyl sulfoxide (DMSO), N,N-dimethylformamide (DMF), N,N-dimethyl acetamide, N-methyl-2-pyrrolidone (NMP)), nitriles (e.g., acetonitrile), hydrocarbon solvents (e.g., toluene, heptane (n-heptane, heptanes), halogenated solvents (e.g., dichloromethane, 1,2-dichloroethane, chloroform, chlorobenzene), alcohols (e.g., 2-propanol). In one embodiment, the solvent is tetrahydrofuran (THF).

In one embodiment, the temperature of the reaction is from −50 to 100° C. In one embodiment, the temperature of the reaction is from 0 to 100° C. In one embodiment, the temperature of the reaction is from −50 to −35° C. In one embodiment, the temperature of the reaction is from 0 to 20° C.

In one embodiment, the present disclosure provides a method to prepare a compound 1-N from a compound 1-M.

In one embodiment, the method comprises the step of treating a compound 1-M with an acid in a suitable solvent, for a time and under conditions effective to form a compound 1-N.

In one embodiment, the acid is selected from methanesulfonic acid, trifluoromethanesulfonic acid, benzenesulfonic acid, p-toluenesulfonic acid, camphorsulfonic acid, pyridinium p-toluenesulfonate, sulfuric acid, hydrochloric acid, hydrobromic acid, acetic acid, formic acid, phosphoric acid, oxalic acid, citric acid, Lewis acids such as erbium(III) triflate. In one embodiment, the acid is methanesulfonic acid.

In one embodiment, the solvent is selected from ethers (e.g., 2-methyltetrahydrofuran, tert-butyl methyl ether, cyclopentyl methyl ether, tetrahydrofuran), polar aprotic solvents (e.g., dimethyl sulfoxide, N,N-dimethylformamide, N,N-dimethylacetamide, N-methyl-2-pyrrolidone), nitriles (e.g., acetonitrile), hydrocarbons (e.g., toluene, n-heptane), halogenated solvents (e.g., dichloromethane, 1,2-dichloroethane, chloroform, chlorobenzene), alcohols (e.g., 2-propanol), esters (e.g., ethyl acetate, isopropyl acetate), ketones (e.g., acetone, 2-butanone, 4-methyl-2-pentanone), water, or a combination thereof. In one embodiment, the solvent is a combination of tetrahydrofuran (THF) and water.

In one embodiment, the temperature of the reaction is from 0 to 100° C. In one embodiment, the temperature of the reaction is from 40 to 60° C.

In one embodiment, the present disclosure provides a method to prepare a compound 1-O from a compound 1-N.

In one embodiment, the method comprises the step of treating a compound 1-N with a reducing agent in a suitable solvent, for a time and under conditions effective to form a compound 1-O.

In one embodiment, the reducing agent is selected from tin or zinc in combination with acids such as hydrochloric acid, acetic acid, ammonium chloride, transition metal such as Pd, Pd(OH)$_2$, Pt, PtO$_2$ or Rh in combination with H$_2$ or a formate salt, poisoned heterogeneous catalysts such as Pt/S/C, and iron powder. In one embodiment, the reducing agent is iron powder.

In one embodiment, the solvent is selected from mixtures of acid (e.g., acetic acid, hydrogen chloride) in combination with other solvents including ethers (e.g., tetrahydrofuran, 2-methyltetrahydrofuran, methyl tert-butyl ether, cyclopentyl methyl ether), polar aprotic solvents (e.g., N,N-dimethylacetamide, N,N-dimethylformamide, N-methylpyrrolidinone, dimethyl sulfoxide), nitriles (e.g., acetonitrile), hydrocarbons (e.g., toluene, n-heptane), halogenated solvents (e.g., dichloromethane, 1,2-dichloroethane, chloroform, chlorobenzene), alcohols (e.g., 2-propanol), esters (e.g., ethyl acetate, isopropyl acetate). In one embodiment, the solvent is acetic acid.

In one embodiment, the temperature of the reaction is from 0 to 100° C. In one embodiment, the temperature of the reaction is from 40 to 60° C.

In one embodiment, the present disclosure provides a method to prepare a compound 1-P from a compound 1-O.

In one embodiment, the method comprises the step of treating a compound 1-O with a reducing agent in a suitable solvent, for a time and under conditions effective to form a compound 1-P. In one embodiment, an additive is present. In one embodiment, an intermediate 1-R is formed. In one embodiment, an intermediate 1-S is formed.

In one embodiment, the reducing agent is selected from sodium cyano borohydride, sodium and lithium borohydride, trialkyl silanes (e.g., triethylsilane) in combination with additives, poisoned heterogeneous catalysts (e.g., Pt/S/C), transition metal (e.g., Pd or Rh) in combination with H$_2$ or a formate salt with additives, Pd and Pt catalysts (e.g., Pd(OH)$_2$, PtO$_2$), and sodium triacetoxyborohydride. In one embodiment, the reducing agent is sodium triacetoxyborohydride.

In one embodiment, the additive is selected from trifluoroacetic acid, pivalic acid, B(OR)$_3$, Ti(OEt)$_4$, and Ti(O-i-Pr)$_4$, wherein R is C$_{1-6}$alkyl.

In one embodiment, the solvent is selected from ethers (e.g., tetrahydrofuran, 2-methyltetrahydrofuran, methyl tert-butyl ether, cyclopentyl methyl ether), polar aprotic solvents (e.g., dimethyl sulfoxide, N,N-dimethylformamide, N,N-dimethylacetamide, N-methyl-2-pyrrolidone), nitriles (e.g., acetonitrile), hydrocarbons (e.g., toluene, n-heptane), halogenated solvents (e.g., dichloromethane, 1,2-dichloroethane, chloroform, chlorobenzene), alcohols (e.g., 2-propanol), esters (e.g., ethyl acetate, isopropyl acetate), and acid (e.g., acetic acid). In one embodiment, the solvent is acetic acid.

In one embodiment, the temperature of the reaction is from 0 to 80° C. In one embodiment, the temperature of the reaction is from 10 to 30° C.

In one embodiment, the present disclosure provides a method to prepare a compound 1-Q from a compound 1-P.

In one embodiment, the method comprises the step of treating a compound 1-P with a compound 1-I, a reducing agent and an acid in a suitable solvent, for a time and under conditions effective to form a compound 1-Q.

In one embodiment, the reducing agent is selected from silanes (e.g., triisopropylsilane, triphenylsilane, triethylsilane, diethylsilane), sodium borohydride, sodium borohydride/acetic acid, sodium triacetoxyborohydride, sodium cyanoborohydride, titanium isopropoxide/sodium cyanoborohydride, zinc/acetic acid, sodium borohydride/magnesium perchlorate, zinc borohydride/zinc chloride, tetramethylammonium triacetoxyborohydride. In one embodiment, the reducing agent is triethylsilane.

In one embodiment, the acid is selected from acetic acid, citric acid, pivalic acid, p-toluenesulfonic acid, methanesulfonic acid, hydrochloric acid, and trifluoroacetic acid. In one embodiment, the acid is trifluoroacetic acid.

In one embodiment, the solvent is selected from ethers (e.g., 2-methyltetrahydrofuran, tetrahydrofuran, methyl tert-butyl ether, cyclopentyl methyl ether), hydrocarbon solvents (e.g., toluene, n-heptane), halogenated solvents (e.g., 1,2-dichloroethane, dichloromethane, chloroform, chlorobenzene), polar aprotic solvents (e.g., N,N-dimethylacetamide, N,N-dimethylformamide, N-methyl-2-pyrrolidinone, dimethyl sulfoxide). In one embodiment, the solvent is dichloromethane.

In one embodiment, the temperature of the reaction is from −30 to 50° C. In one embodiment, the temperature of the reaction is from 10 to 30° C.

In one embodiment, the present disclosure provides a method to prepare a compound 1-K from a compound 1-Q.

In one embodiment, the method comprises the step of treating a compound 1-Q with a ligand, an additive, and a base in the presence of a catalyst in a suitable solvent, for a time and under conditions effective to form a compound 1-K. In one embodiment, an acid is present. In one embodiment, $R^z$ is Br.

In one embodiment, the method comprises the step of treating a compound 1-Q with an acid and a base in a suitable solvent, for a time and under conditions effective to form a compound 1-K. In one embodiment, an additive is present. In one embodiment, $R^z$ is CN.

In one embodiment, the catalyst is selected from bis(triphenylphosphine)palladium dichloride, diiodobis(3-methyl-2(3H)-benzothiazolylidene)palladium, bis(benzonitrile)dichloropalladium, dichloro(1,5-cyclooctadiene)palladium, dicobalt hexacarbonyl, and palladium acetate. In one embodiment, the catalyst is palladium acetate (Pd(OAc)$_2$).

In one embodiment, the ligand is selected from triphenylphosphine, 2-dicyclohexylphosphino-2',4',6'-triisopropylbiphenyl (XPhos) and 4,5-bis(diphenylphosphino)-9,9-dimethylxanthene (XantPhos). In one embodiment, the ligand is 2-dicyclohexylphosphino-2',4',6'-triisopropylbiphenyl (XPhos).

In one embodiment, the additive is selected from ethyl oxalate, potassium fluoride, carbon monoxide, tetrabutylammonium bromide, propylene oxide, acetic anhydride, and dicyclohexylcarbodiimide (DCC). In one embodiment, the additive is dicyclohexylcarbodiimide (DCC).

In one embodiment, the acid is formic acid.

In one embodiment, the acid is selected from acetic acid, citric acid, pivalic acid, p-toluenesulfonic acid, methanesulfonic acid, hydrochloric acid, and trifluoroacetic acid. In one embodiment, the acid is trifluoroacetic acid.

In one embodiment, the acid is selected from methanesulfonic acid, sulfuric acid, phosphoric acid, and hydrochloric acid. In one embodiment, the acid is hydrochloric acid.

In one embodiment, the base is selected from N,N-dimethylaminopyridine, N,N,N',N'-tetramethylethandiamine, sodium hydroxide, sodium acetate, sodium hydroxide, potassium carbonate, and triethylamine. In one embodiment, the base is triethylamine.

In one embodiment, the base is selected from alkoxide bases (e.g. sodium hydroxide, sodium methoxide, potassium tert-butoxide, lithium hydroxide, cesium hydroxide, barium hydroxide, potassium hydroxide), carbonate bases (e.g. potassium carbonate, cesium carbonate, sodium carbonate, sodium bicarbonate), pyridine, triethylamine, potassium benzoate. In one embodiment, the base is potassium hydroxide.

In one embodiment, the solvent is selected from benzene, toluene, dimethylacetamide, dimethylformide, alcohols (e.g. ethanol, methanol, isopropanol, butanol) dimethylsulfoxide, dichoromethane, tetrahydrofuran, water, and a combination thereof. In one embodiment, the solvent is dimethylformide. In one embodiment, the solvent is a combination of methanol and water.

In one embodiment, the temperature of the reaction is from −30 to 155° C. In one embodiment, the temperature is from 80 to 110° C. In one embodiment, the temperature is from 80 to 100° C.

In one embodiment, the present disclosure provides a method to prepare a compound 9-A from a compound 1-K and a compound 6-L.

In one embodiment, the present disclosure provides a method to prepare a compound 1 from a compound 9-A.

In one embodiment, the present disclosure provides a method of making a compound 1 from a compound selected from 1-L, 5-E, 1-M. 1-N, 1-O, 1-P, 1-Q, 1-K, or 9-A, as shown in Scheme 1.

In one embodiment, the present disclosure provides a method of making a compound 9-A from a compound selected from 1-L, 5-E, 1-M. 1-N, 1-O, 1-P, 1-Q, or 1-K.

In one embodiment, the present disclosure provides a method of making a compound 1-K from a compound selected from 1-L, 5-E, 1-M. 1-N, 1-O, 1-P, or 1-Q.

B. Method of Preparing Compound 1 from Formula 2-F

In one embodiment, the present disclosure provides a method of making a compound selected from 2-G, 2-H, 2-I, 2-J, 2-K, 2-L, 1-J, 1-K, 9-A and compound 1, as shown in Scheme 2, wherein $R^2$ is H, $R^3$ is methyl, $R^x$ and $R^y$ are independently H, $C_{1-6}$alkyl, or $C_{6-10}$aryl, wherein the alkyl is optionally substituted with $C_{6-10}$aryl, $R^a$ is $C_{1-6}$alkyl, PG is selected from a tri-$C_{1-6}$alkyl silyl group, a di-$C_{1-6}$alkyl-phenyl silyl group, a $C_{1-6}$alkyl-di-phenyl silyl group, and a tri-phenyl silyl group, and $R^p$ is selected from —C(=O)—$C_{1-6}$alkyl, —C(=O)-heteroaryl, —C(=O)—O—$C_{1-6}$alkyl, and —C(=O)—O—$C_{1-6}$alkyl-$C_{6-10}$aryl, wherein each aryl or heteroaryl is optionally substituted with one to four groups independently selected from $C_{1-3}$alkyl and —OC$_{1-3}$alkyl, wherein each heteroaryl has one to four heteroatoms; wherein each heteroatom is independently selected from N, O, and S, and wherein each heteroaryl has 5 to 10 ring members. In one embodiment, PG is tert-butyldiphenylsilyl. In one embodiment, $R^a$ is methyl. In one embodiment, $R^x$ is methyl.

Scheme 2
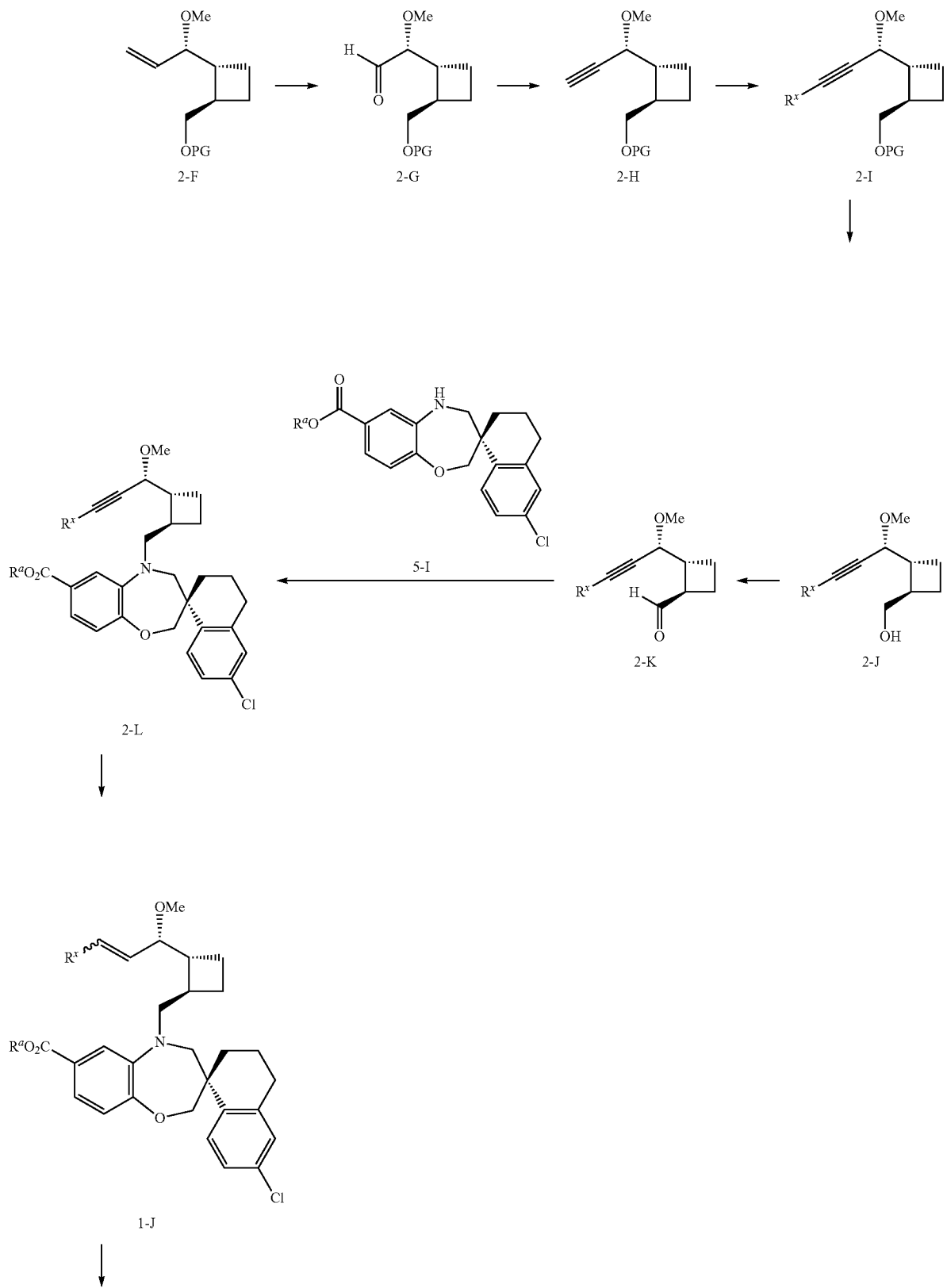

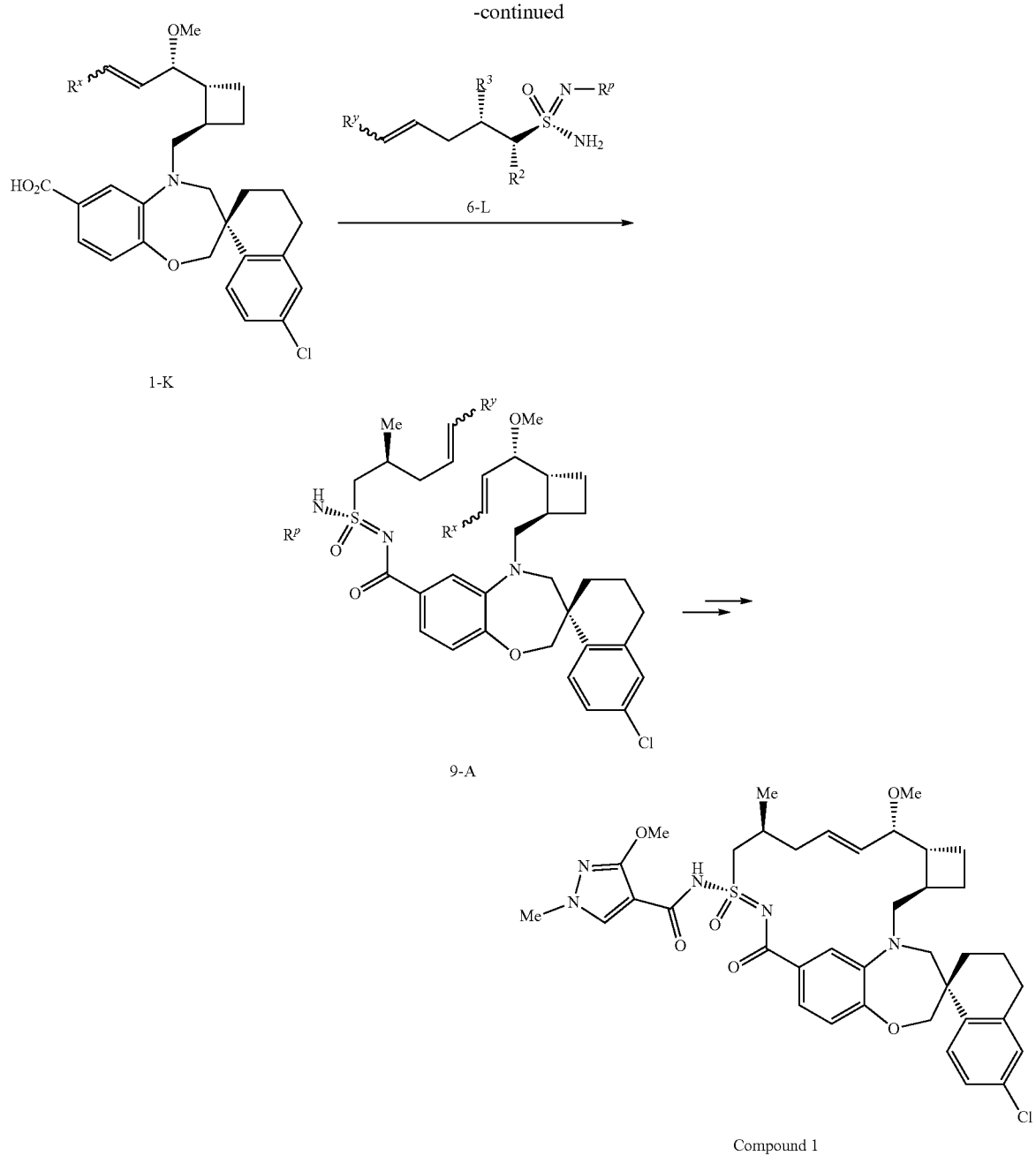

Compound 1

In one embodiment, the present disclosure provides a method to prepare a compound 2-G from a compound 2-F.

In one embodiment, the method comprises the step of reacting a compound 2-F with a catalyst, an oxidant, and an additive in a suitable solvent, for a time and under conditions effective to form a compound 2-G.

In one embodiment, the catalyst is selected from ruthenium chloride, potassium osmate, tungstophosphoric acid, and osmium tetroxide ($OsO_4$). In one embodiment, the catalyst is osmium tetroxide ($OsO_4$).

In one embodiment, the oxidant is selected from oxone, potassium permanganate, potassium periodate, lead tetraacetate, sodium hypochlorite, hydrogen peroxide, N-methylmorpholine N-oxide (NMO), sodium periodate ($NaIO_4$), and a combination thereof.

In one embodiment, the oxidant is a combination of N-methylmorpholine N-oxide (NMO) and sodium periodate ($NaIO_4$).

In one embodiment, the additive is selected from aluminum oxide, cerium trichloride, triethylamine, triphenylphosphine, bis(diphenylphosphanyl)ethane, pyridine, 2,6-lutidine, dimethylsulfide, zinc, acetic acid potassium carbonate, trimethoxy phosphine, and potassium iodide. In one embodiment, the additive is 2,6-lutidine.

In one embodiment, the solvent is selected from methanol, ethanol, dichloromethane, dichloroethane, dioxane, dimethylsulfoxide, acetonitrile, acetone, tert-butanol, tetrahydrofuran (THF), water, and a combination thereof. In one embodiment, the solvent is a combination of tetrahydrofuran (THF) and water.

In one embodiment, the temperature of the reaction is from −80 to 35° C. In one embodiment, the temperature is from 20 to 35° C.

In one embodiment, the present disclosure provides a method to prepare a compound 2-H from a compound 2-G.

In one embodiment, the method comprises the step of reacting a compound 2-G with a promoter and a base in a suitable solvent, for a time and under conditions effective to form a compound 2-H. In one embodiment, an additive is present.

In one embodiment, the promoter is selected from (dichloromethyl)diethoxyphosphine oxide, lithium (trimethylsilyl)diazomethane, (trimethylsilyl)diazomethane, imidazole sulfonyl azide hydrochloride, (2-oxopropyl)phosphonic acid dimethyl ester, p-Toluenesulfonyl azide, azidotris(diethylamino)phosphonium bromide, acetamidobenzenesulfonyl azide, diethyl (1-diazo-2-oxopropyl)phosphonate, carbon tetrabromide, carbon tetrachloride, triiodomethane, triphenylphosphine, dibromomethyl(triphenyl)phosphonium bromide, (iodomethyl)triphenylphosphonium iodide, isopropyl phosphite, chromium chloride, and dimethyl (acetyldiazomethyl)phosphonate. In one embodiment, the promoter is dimethyl (acetyldiazomethyl)phosphonate.

In one embodiment, the base is selected from n-butyllithium, sec-butyllithium, tert-butyllithium, methyl lithium, lithium diisopropylamine, sodium hexamethyldisilazane, diazabicycloundecene, potassium tert-butoxide, potassium methoxide, sodium methoxide, sodium hydroxide, cesium carbonate, and potassium carbonate. In one embodiment, the base is potassium carbonate.

In one embodiment, the additive is tetrabutylammonium fluoride.

In one embodiment, the solvent is selected from diethylether, tetrahydrofuran, acetonitrile, dichloromethane, ethanol and methanol. In one embodiment, the solvent is methanol.

In one embodiment, the temperature of the reaction is from −80 to 40° C. In one embodiment, the temperature is from 20 to 30° C.

In one embodiment, the present disclosure provides a method to prepare a compound 2-I from a compound 2-H.

In one embodiment, the method comprises the step of treating a compound 2-H with a base and an alkylating agent in a suitable solvent, for a time and under conditions effective to form a compound 2-I. In one embodiment, a promoter is present.

In one embodiment, the promoter is selected from dichlorobis(triphenylphosphine)palladium, tris(4-methoxyphenyl) phosphine, and copper iodide.

In one embodiment, the base is selected from lithium diisopropylamine, hexamethyldisilazane, sodium hexamethyldisilazane, sodium amide, lithium amide, diisopropylamine, triethylamine, tert-butyl lithium, sodium hydride, sodium tert-butoxide, potassium tert-butoxide, and n-butyllithium (n-BuLi). In one embodiment, the base is n-butyllithium (n-BuLi).

In one embodiment, the alkylating agent is selected from dimethylsulfate, methyltriflate, methyl tosylate, bromomethane, trimethyl triflouromethansulfonate benzaminium, and methyl iodide. In one embodiment, the alkylating agent is methyl iodide.

In one embodiment, the solvent is selected from dimethylsulfoxide, dioxane, diethylether, DMPU hexamethylphosphoramide, hexanes, heptane, pyridine, and tetrahydrofuran. In one embodiment, the solvent is tetrahydrofuran.

In one embodiment, the temperature of the reaction is from −80 to 100° C. In one embodiment, the temperature is from −80 to 20° C.

In one embodiment, the present disclosure provides a method to prepare a compound 2-J from a compound 2-I.

In one embodiment, the method comprises the step of treating a compound 2-I with a reagent in a suitable solvent, for a time and under conditions effective to form a compound 2-J.

In one embodiment, the reagent is selected from sodium hydroxide, potassium hydroxide, lithium hydroxide, sulfuric acid, trifluoroacetic acid, phosphoric acid, hydrochloric acid, hydrofluoric acid, hydrogen fluoride pyridine, hydrogen fluoride triethylamine, potassium fluoride, sodium fluoride, lithium fluoride, tetramethylammonium fluoride, and tetrabutyl ammonium fluoride (TBAF). In one embodiment, the reagent is tetrabutyl ammonium fluoride (TBAF).

In one embodiment, the solvent is selected from ethers (e.g., 2-methyltetrahydrofuran, tetrahydrofuran, methyl tert-butyl ether, cyclopentyl methyl ether), hydrocarbon solvents (e.g, toluene, n-heptane), halogenated solvents (e.g., dichloromethane, 1,2-dichloroethane, chloroform, chlorobenzene), alcohols (e.g., methanol, ethanol, n-propanol, isopropanol), polar aprotic solvents (e.g., N,N-dimethylacetamide, N,N-dimethylformamide, N-methyl-2-pyrrolidinone, dimethyl sulfoxide), and water. In one embodiment, the solvent is tetrahydrofuran.

In one embodiment, the temperature of the reaction is from −20 to 50° C. In one embodiment, the temperature is from 20 to 30° C.

In one embodiment, the present disclosure provides a method to prepare a compound 2-K from a compound 2-J.

In one embodiment, the method comprises the step of treating a compound 2-J with an oxidant in the presence of a catalyst in a suitable solvent, for a time and under conditions effective to form a compound 2-K. In one embodiment, an additive is present.

In one embodiment, the oxidant is selected from sodium hypochlorite/TEMPO, sulfur trioxide pyridine, dimethyl sulfoxide (DMSO)/oxalyl chloride, DMSO/acetic anhydride, diacetoxyiodobenzene/TEMPO, tetrapropylammonium perruthenate/N-methylmorpholine N-oxide, and diacetoxyiodobenzene (DAIB). In one embodiment, the oxidant is diacetoxyiodobenzene (DAIB).

In one embodiment, the catalyst is selected from 2-azaadamantane N-oxyl, 9-azabicyclo[3.3.1]nonane N-oxyl, 9-azanoradamantane N-oxyl, and (2,2,6,6-tetramethylpiperidin-1-yl)oxyl (TEMPO). In one embodiment, the catalyst is (2,2,6,6-tetramethylpiperidin-1-yl)oxyl (TEMPO).

In one embodiment, the additive is selected from sodium bromide, lithium bromide, and potassium bromide.

In one embodiment, the solvent is selected from ethers (e.g., 2-methyltetrahydrofuran, tetrahydrofuran, methyl tert-butyl ether, cyclopentyl methyl ether), hydrocarbon solvents (e.g., toluene, n-heptane), halogenated solvents (e.g., 1,2-dichloroethane, chloroform, dichloromethane, chlorobenzene), polar aprotic solvents (e.g, N,N-dimethylacetamide, N,N-dimethylformamide, N-methyl-2-pyrrolidinone, dimethyl sulfoxide), and water. In one embodiment, the solvent is tetrahydrofuran.

In one embodiment, the temperature of the reaction is from −80 to 50° C. In one embodiment, the temperature is from 20 to 30° C.

In one embodiment, the present disclosure provides a method to prepare a compound 2-L from a compound 2-K and a compound 5-I.

In one embodiment, the method comprises the setup of treating a compound 2-K with a compound 5-I, a reducing agent and an acid in the presence of a catalyst in a suitable solvent, for a time and under conditions effective to form a compound 2-L. In one embodiment, an additive is present.

In one embodiment, the reducing agent is selected from silanes (e.g., triisopropylsilane, triphenylsilane, diethylsilane, triethylsilane), sodium borohydride, sodium borohydride/acetic acid, sodium triacetoxyborohydride, sodium cyanoborohydride, titanium isopropoxide/sodium cyanoborohydride, zinc/acetic acid, sodium borohydride/magnesium perchlorate, zinc borohydride/zinc chloride, and tetramethylammonium triacetoxyborohydride. In one embodiment, the reducing agent is triethylsilane.

In one embodiment, the acid is selected from acetic acid, citric acid, pivalic acid, p-toluenesulfonic acid, methanesulfonic acid, hydrochloric acid, and trifluoroacetic acid. In one embodiment, the acid is trifluoroacetic acid.

In one embodiment, the solvent is selected from ethers (e.g., 2-methyltetrahydrofuran, tetrahydrofuran, methyl tert-butyl ether, cyclopentyl methyl ether), hydrocarbon solvents (e.g., toluene, n-heptane), halogenated solvents (e.g., 1,2-dichloroethane, chloroform, chlorobenzene), polar aprotic solvents (e.g., N,N-dimethylacetamide, N,N-dimethylformamide, N-methyl-2-pyrrolidinone, dimethyl sulfoxide), and acetonitrile. In one embodiment, the solvent is acetonitrile.

In one embodiment, the temperature of the reaction is from −30 to 50° C. In one embodiment, the temperature is from 10 to 30° C.

In one embodiment, the present disclosure provides a method to prepare a compound 1-J from a compound 2-L.

In one embodiment, the present disclosure provides a method to prepare a compound 1-K from a compound 1-J.

In one embodiment, the present disclosure provides a method to prepare a compound 9-A from a compound 1-K and a compound 6-L.

In one embodiment, the present disclosure provides a method to prepare a compound 1 from a compound 9-A.

In one embodiment, the present disclosure provides a method of making a compound 1 from a compound selected from 2-F, 2-G, 2-H, 2-I, 2-J, 2-K, 2-L, 1-J, 1-K, and 9-A, as shown in Scheme 2.

In one embodiment, the present disclosure provides a method of making a compound 9-A from a compound selected from 2-G, 2-H, 2-I, 2-J, 2-K, 2-L, 1-J and 1-K.

In one embodiment, the present disclosure provides a method of making a compound 1-K from a compound selected from 2-G, 2-H, 2-I, 2-J, 2-K, 2-L and 1-J.

In one embodiment, the present disclosure provides a method of making a compound 1-J from a compound selected from 2-G, 2-H, 2-I, 2-J, 2-K, and 2-L.

C. Method of Preparing Compound 1 from Formula 3-E

In one embodiment, the present disclosure provides a method of making a compound selected from 3-F, 3-G, 2-L, 3-H, 1-K, 9-A and compound 1, as shown in Scheme 3, wherein $R^2$ is H, $R^3$ is methyl, $R^x$ and $R^y$ are independently H, $C_{1-6}$alkyl, or $C_{6-10}$aryl, wherein the $C_{1-6}$alkyl is optionally substituted with $C_{6-10}$aryl, $R^a$ is $C_{1-6}$alkyl, and $R^p$ is selected from —C(=O)—$C_{1-6}$alkyl, —C(=O)-heteroaryl, —C(=O)—O—$C_{1-6}$alkyl, and —C(=O)—O—$C_{1-6}$alkyl-$C_{6-10}$aryl, wherein each $C_{6-10}$aryl or heteroaryl is optionally substituted with one to four groups independently selected from $C_{1-3}$alkyl and —O$C_{1-3}$alkyl, wherein each heteroaryl has one to four heteroatoms; wherein each heteroatom is independently selected from N, O, and S, and wherein each heteroaryl has 5 to 10 ring members. In one embodiment, PG is tert-butyldiphenylsilyl. In one embodiment, $R^a$ is methyl. In one embodiment, $R^x$ is methyl.

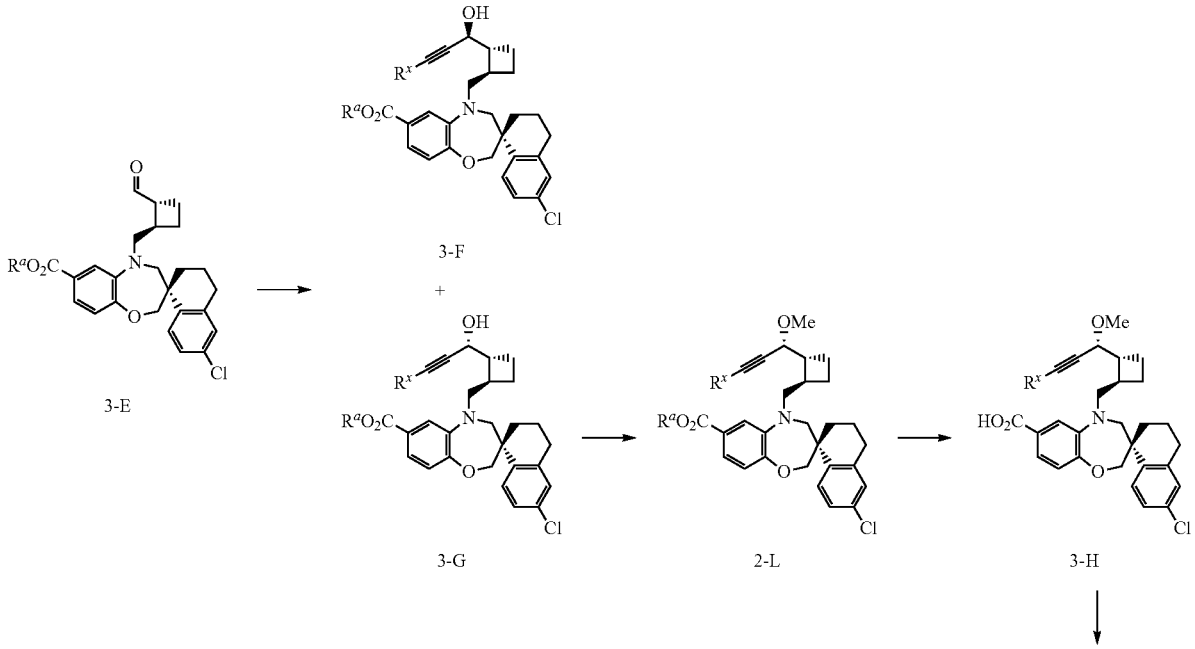

Scheme 3

-continued

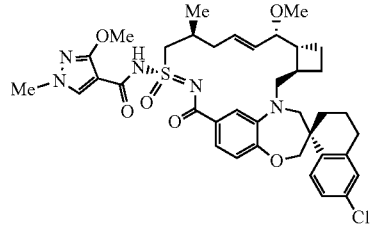

Compound 1

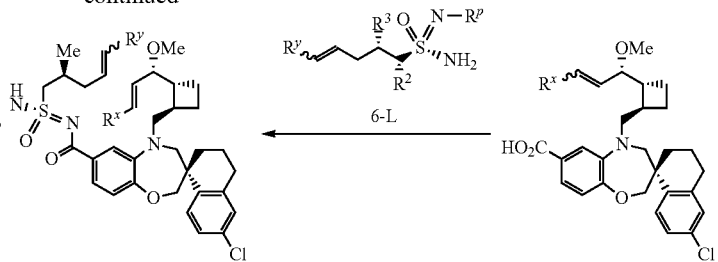

9-A                               1-K

In one embodiment, the present disclosure provides a method to prepare a compound 3-F and 3-G from a compound 3-E.

In one embodiment, the method comprises the step of treating a compound 3-E with a nucleophile in a suitable solvent, for a time and under conditions effective to form a compound 3-F and 3-G. In one embodiment, a promoter is present.

In one embodiment, the nucleophile is selected from propyne, propynyl lithium, propynylmagnesium chloride, dipropynyl zinc, propynylzinc chloride, propynylmagnesium bromide, and 3-bromopropyne. In one embodiment, the nucleophile is propynylmagnesium bromide.

In one embodiment, the promoter is selected alkyl lithiums (e.g. n-butyllithium, s-butyllithium, t-butyllithium, methyl lithium), Grignards (e.g. ethylmagnesium bromide, isopropylmagnesium chloride, butylmagnesium bromide) lithium diisopropylamine, copper iodide, lithium perchlorate, lithium bromide, lanthanum chloride lithium chloride complex, cerium trichloride, boron trifluoride, titanium(IV) isopropoxide, zinc triflate, diethylzine, N-methylephedrine, L-tartaric acid, R-2,2-Binaphthol, triethylamine, tetramethyl ethylenediamine, diisopropylamine, and zinc.

In one embodiment, the solvent is selected from ethereal solvents (e.g. diethylether, 2-methyltetrahydrofuran, tetrahydrofuran), hydrocarbon solvents (e.g. hexanes, heptane, cyclohexane), dimethylsulfide, halogenated solvents (e.g. dichloromethane), and aromatic solvents (e.g. benzene, toluene). In one embodiment, the solvent is tetrahydrofuran.

In one embodiment, the temperature of the reaction is from −80 to 30° C. In one embodiment, the temperature is from −80 to 20° C.

In one embodiment, the present disclosure provides a method to prepare a compound 2-L from a compound 3-G.

In one embodiment, the method comprises the step of treating a compound 3-G with an alkylating reagent and a base in a suitable solvent, for a time and under conditions effective to form a compound 2-L.

In one embodiment, the alkylating reagent is iodomethane.

In one embodiment, the base is sodium tert-butoxide.

In one embodiment, the solvent is tetrahydrofuran.

In one embodiment, the temperature of the reaction is from 0 to 30° C.

In one embodiment, the present disclosure provides a method to prepare a compound 3-H from a compound 2-L.

In one embodiment, the method comprises the step of treating a compound 2-L with an additive in a suitable solvent, for a time and under conditions effective to form a compound 3-H.

In one embodiment, the additive is a base selected from hydroxides (e.g., lithium hydroxide, sodium hydroxide, potassium hydroxide, cesium hydroxide, calcium hydroxide, magnesium hydroxide ammonium hydroxide, tetramethylammonium hydroxide), alkoxides (e.g., lithium, sodium, potassium, magnesium, calcium methoxide, ethoxide, isopropoxide, t-butoxide, or t-pentoxide), trimethyltin hydroxide, sodium trimethylsilanolate, and potassium trimethylsilanolate. In one embodiment, the additive is lithium hydroxide.

In one embodiment, the additive is an acid selected from inorganic acids (e.g., hydrochloric acid, hydrobromic acid, hydroiodic acid, sulfuric acid, phosphoric acid), and organic acids (e.g., acetic acid, trifluoroacetic acid, methanesulfonic acid, benzenesulfonic acid, toluenesulfonic acid).

In one embodiment, the solvent is selected from ethers (e.g., 2-methyltetrahydrofuran, tetrahydrofuran, methyl tert-butyl ether, cyclopentyl methyl ether), alcohols (methanol, ethanol, isopropanol, t-butanol, t-amyl alcohol, etc.), water, halogenated solvents (e.g., 1,2-dichloroethane, chloroform, chlorobenzene), and a combination thereof. In one embodiment, the solvent is a combination of tetrahydrofuran and water.

In one embodiment, the temperature of the reaction is from 20 to 100° C. In one embodiment, the temperature is from 40 to 60° C.

In one embodiment, the present disclosure provides a method to prepare a compound 1-K from a compound 3-H.

In one embodiment, the present disclosure provides a method of making a compound 1 from a compound selected from 3-E, 3-G, 2-L, 3-H, 1-K, and 9-A, as shown in Scheme 3.

D. Method of Preparing Compound 1 from Formula 4-F

In one embodiment, the present disclosure provides a method of making a compound selected from 4-G, 4-H, 4-I, 4-J, 4-L, 4-M, 4-N, and compound 1, as shown in Scheme 4, wherein $R^4$ is halo or boronic ester, $R^b$ is $C_{1-6}$alkyl, $R^c$ is $C_{1-6}$alkyl, X is halogen, boronate, —OS(O)$_2R^2$, or —OP(O)(R$^2$)$_2$, wherein $R^2$ is $C_{1-6}$alkyl or $C_{6-10}$aryl, wherein each alkyl or aryl is optionally substituted with one to four halogen or $C_{1-3}$alky, and $R^p$ is selected from —C(=O)—$C_{1-6}$alkyl, —C(=O)-heteroaryl, —C(=O)—O—$C_{1-6}$alkyl, and —C(=O)—O—$C_{1-6}$alkyl-$C_{6-10}$aryl, wherein each aryl or heteroaryl is optionally substituted with one to four groups independently selected from $C_{1-3}$alkyl and —O$C_{1-3}$alkyl, wherein each heteroaryl has one to four heteroatoms; wherein each heteroatom is independently selected from N, O, and S, and wherein each heteroaryl has 5 to 10 ring members. In one embodiment, $R^b$ is methyl. In one embodiment, $R^c$ is methyl. In one embodiment, $R^p$ is 1-phenylethoxycarbonyl. In one embodiment, X is

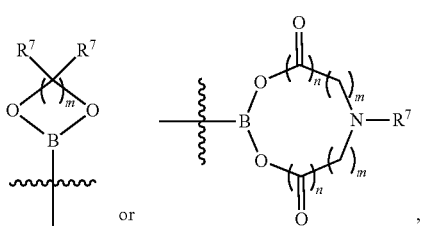
or ,
wherein each $R^7$ is independently H or $C_{1-3}$alkyl, m is 1, 2, or 3, and n is 0 or 1. In one embodiment, X is
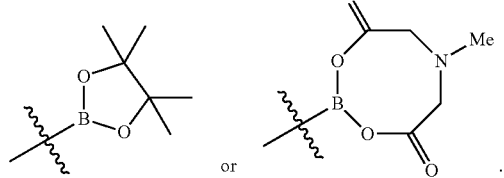
or .
Scheme 4
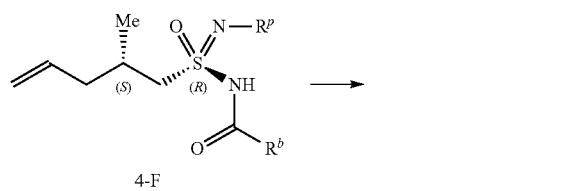
4-F
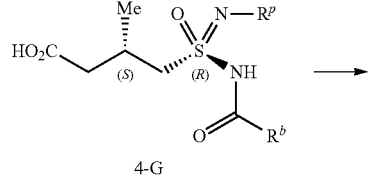
4-G
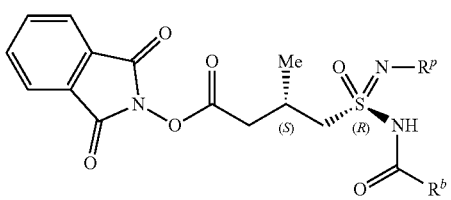
4-H
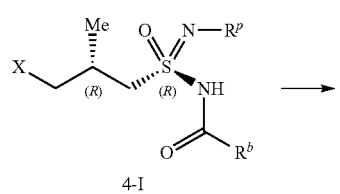
4-I
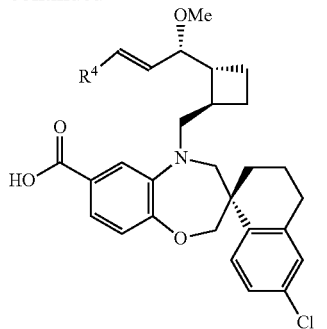
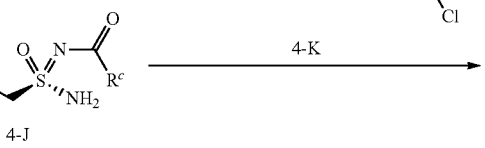
4-J
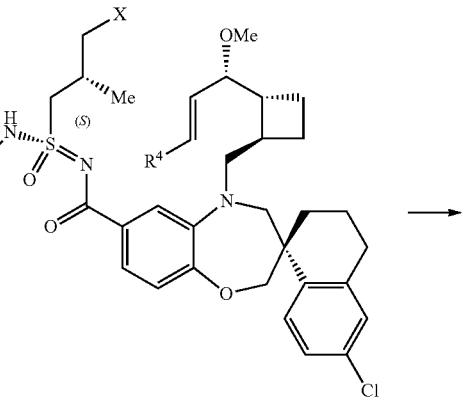
4-L
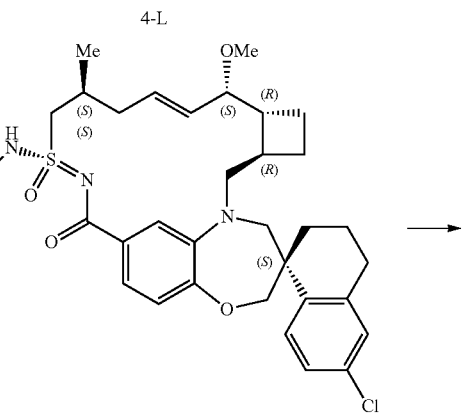
4-M
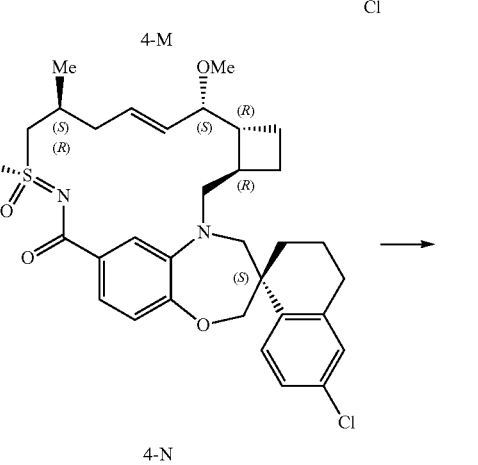
4-N -continued

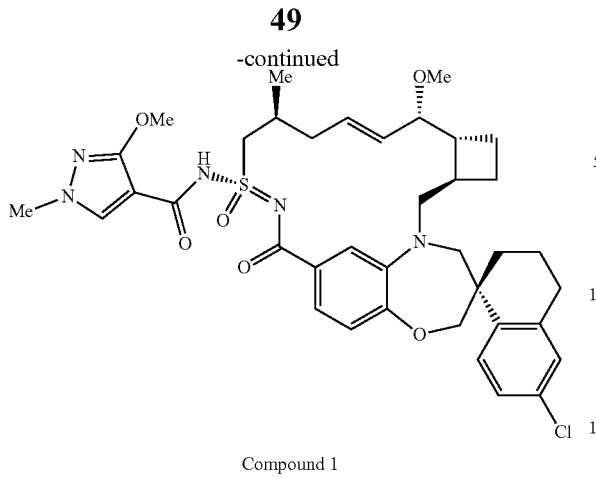

Compound 1

In one embodiment, the present disclosure provides a method to prepare a compound 4-G from a compound 4-F.

In one embodiment, the method comprises the step of treating a compound 4-F with a promoter and an oxidant in a suitable solvent, for a time and under conditions effective to form a compound 4-G.

In one embodiment, the promoter is selected from Ruthenium chloride, potassium osmate, tungstophosphoric acid. In one embodiment, the promoter is Ruthenium chloride.

In one embodiment, the oxidant is selected from oxone, potassium permanganate, potassium periodate, lead tetraacetate, sodium hypochlorite, hydrogen peroxide, and sodium periodate. In one embodiment, the oxidant is sodium periodate.

In one embodiment, the solvent is selected from ethers (e.g., 2-methyltetrahydrofuran, tetrahydrofuran, methyl tert-butyl ether, cyclopentyl methyl ether), hydrocarbon solvents (e.g., toluene, n-heptane), halogenated solvents (e.g., dichloromethane, 1,2-dichloroethane, chloroform, chlorobenzene), alcohols (e.g., methanol, isopropanol, n-propanol), polar aprotic solvents (e.g., N,N-dimethylacetamide, N,N-dimethylformamide, N-methyl-2-pyrrolidinone, dimethyl sulfoxide), acetonitrile, and a combination thereof. In one embodiment, the solvent is a combination of acetonitrile and water.

In one embodiment, the temperature of the reaction is from −80 to 80° C. In one embodiment, the temperature is from 10 to 30° C.

In one embodiment, the present disclosure provides a method to prepare a compound 4-H from a compound 4-G.

In one embodiment, the method comprises the step of treating a compound 4-G with N-hydroxyphthalimide and an acid activator in a suitable solvent, for a time and under conditions effective to form a compound 4-H.

In one embodiment, the acid activator is selected from carbonyldiimidazole (CDI), propylphosphonic anhydride (T3P), 1-[bis(dimethylamino)methylene]-1H-1,2,3-triazolo[4,5-b]pyridinium 3-oxide hexafluorophosphate (HATU), 4-(4,6-dimethoxy-1,3,5-triazin-2-yl)-4-methyl-morpholinium chloride (DMTMM), thionyl chloride, oxalyl chloride, (chloromethylene)-dimethyliminium chloride, isobutyl chloroformate, N,N,N',N'-tetramethylchloroformamidinium hexafluorophosphate (TCFH), N,N'-diisopropylcarbodiimide, N,N'-dicyclohexylcarbodiimide, diphenyl chlorophosphate, 2,4,6-trichlorobenzoyl chloride, 2-chloro-4,6-dimethoxy-1,3,5-triazine (CDMT), and N-(3-dimethylaminopropyl)-N'-ethylcarbodiimide hydrochloride (EDC.HCl). In one embodiment, the acid activator is N-(3-dimethylaminopropyl)-N'-ethylcarbodiimide hydrochloride (EDC.HCl).

In one embodiment, the solvent is selected from ethers (e.g., tetrahydrofuran, 2-methyltetrahydrofuran, methyl tert-butyl ether, cyclopentyl methyl ether), esters (e.g, ethyl acetate, isopropyl acetate), polar aprotic solvents (e.g., N,N-dimethylacetamide, N-methyl-2-pyrrolidinone, dimethyl sulfoxide), nitriles (e.g., acetonitrile), hydrocarbon solvents (e.g., toluene), halogenated solvents (e.g., dichloromethane, 1,2-dichloroethane, chloroform, chlorobenzene). In one embodiment, the solvent is dichloromethane.

In one embodiment, the temperature of the reaction is from −50 to 50° C. In one embodiment, the temperature is from 10 to 30° C.

In one embodiment, the present disclosure provides a method to prepare a compound 4-I from a compound 4-H.

In one embodiment, the method comprises the step of treating a compound 4-H with a diboron reagent, a promoter and an additive in a suitable solvent, for a time and under conditions effective to form a compound 4-I.

In one embodiment, the promoter is selected from visible light (380-700 nm), UV light (10-400 nm), blue LEDs (420 nm). In one embodiment, the promoter is blue LEDs (420 nm).

In one embodiment, the diboron reagent is selected from bis(pinacolato)diboron, bis(neopentyl glycolato)diboron, bis(hexylene glycolato)diboron, 2,2'-bi-1,3,2-dioxaborinane, and bis(catecholato)diboron. In one embodiment, the diboron reagent is bis(catecholato)diboron.

In one embodiment, the additive is selected from pinacol, diethanolamine, methyliminodiacetic acid, and alcohols (e.g., methanol, isopropanol, n-propanol). In one embodiment, the additive is methyliminodiacetic acid.

In one embodiment, the solvent is selected from ethers (e.g., tetrahydrofuran, 2-methyltetrahydrofuran, methyl tert-butyl ether, cyclopentyl methyl ether), esters (e.g, ethyl acetate, isopropyl acetate), polar aprotic solvents (e.g., N,N-dimethylacetamide, N-methyl-2-pyrrolidinone, dimethyl sulfoxide, dimethylacetamide), nitriles (e.g., acetonitrile), hydrocarbon solvents (e.g., toluene), and halogenated solvents (e.g., dichloromethane, 1,2-dichloroethane, chloroform, chlorobenzene). In one embodiment, the solvent is dimethylacetamide.

In one embodiment, the temperature of the reaction is from −80 to 120° C. In one embodiment, the temperature is from 10 to 30° C.

In one embodiment, the present disclosure provides a method to prepare a compound 4-J from a compound 4-I.

In one embodiment, the present disclosure provides a method to prepare a compound 4-L from a compound 4-J and a compound 4-K.

In one embodiment, the present disclosure provides a method to prepare a compound 4-M from a compound 4-L.

In one embodiment, the present disclosure provides a method to prepare a compound 4-N from a compound 4-M.

In one embodiment, the present disclosure provides a method of making a compound 1 from a compound selected from 4-F, 4-G, 4-H, 4-I, 4-J, 4-L, 4-M, and 4-N, as shown in Scheme 4.

E. Method of Preparing Compound 1 from Formula 5-J

In one embodiment, the present disclosure provides a method of making a compound selected from 5-K, 5-L, 5-M, 5-N, 5-P, 5-Q, and compound 1, as shown in Scheme 5, wherein $R^4$ is halo or boronic ester, X is halogen, boronate, —OS(O)$_2$R$^2$, or —OP(O)(R$^2$)$_2$, wherein $R^2$ is $C_{1-6}$alkyl or $C_{6-10}$aryl, wherein each alkyl or aryl is optionally substituted with one to four halogen or $C_{1-3}$alky, each $R''$ is independently $C_{1-6}$alkyl, or the two $R''$ moieties join together to form a $C_{2-4}$alkyl bridge, wherein the bridge is optionally substituted by one to four groups independently selected from $C_{1-3}$alkyl and phenyl, and $R^p$ is selected from —C(=O)—$C_{1-6}$alkyl, —C(=O)-heteroaryl, —C(=O)—O—$C_{1-6}$alkyl, and —C(=O)—O—$C_{1-6}$alkyl-$C_{6-10}$aryl, wherein each aryl or heteroaryl is optionally substituted with one to four groups independently selected from $C_{1-3}$alkyl and —O$C_{1-3}$alkyl, wherein each heteroaryl has one to four heteroatoms; wherein each heteroatom is independently selected from N, O, and S, and wherein each heteroaryl has 5 to 10 ring members. In one embodiment, $R^p$ is 1-phenylethoxycarbonyl. In one embodiment, $R''$ is methyl. In one embodiment, X is

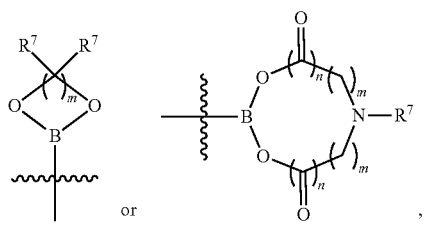

wherein each $R^7$ is independently H or $C_{1-3}$alkyl, m is 1, 2, or 3, and n is 0 or 1. In one embodiment, X is

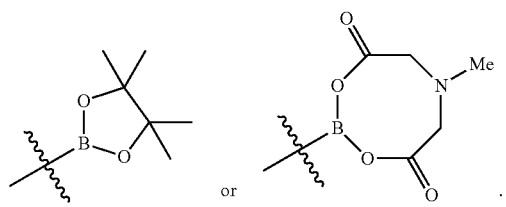

In one embodiment, X is

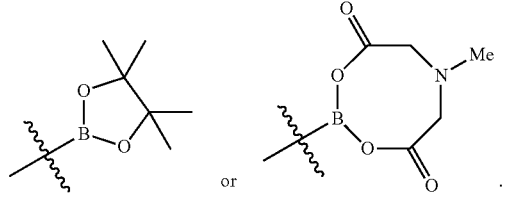

Scheme 5

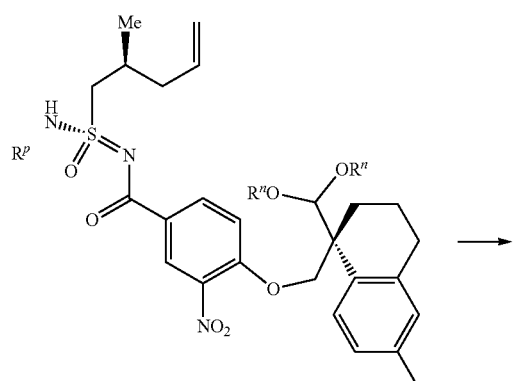

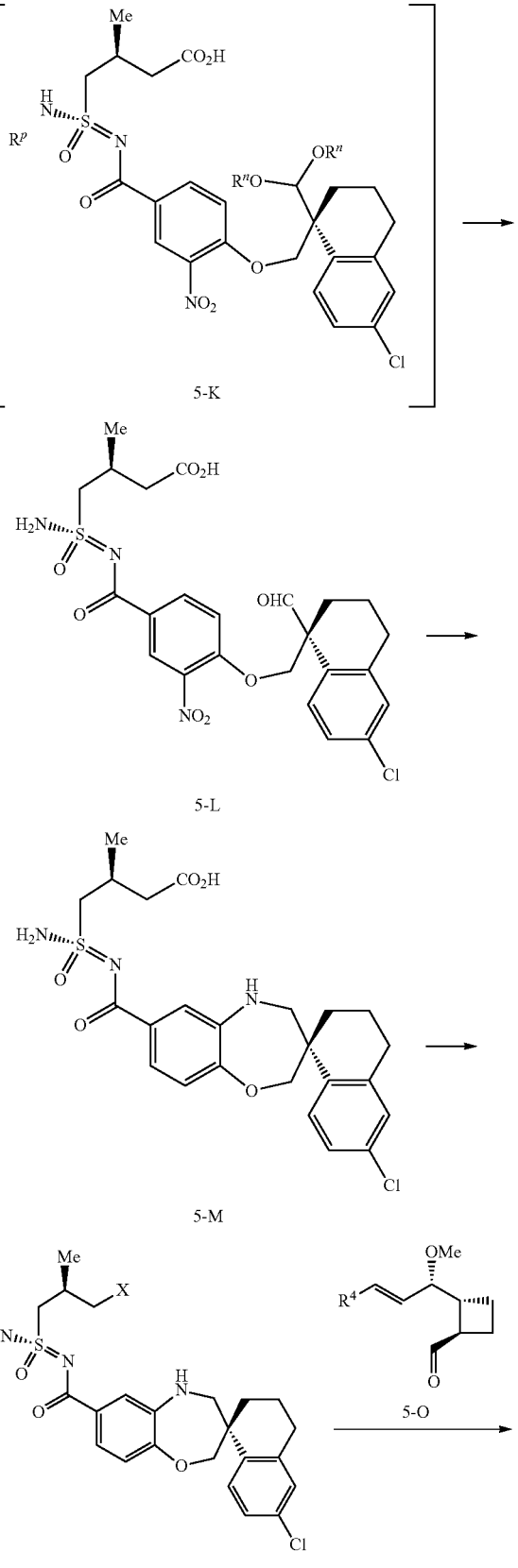

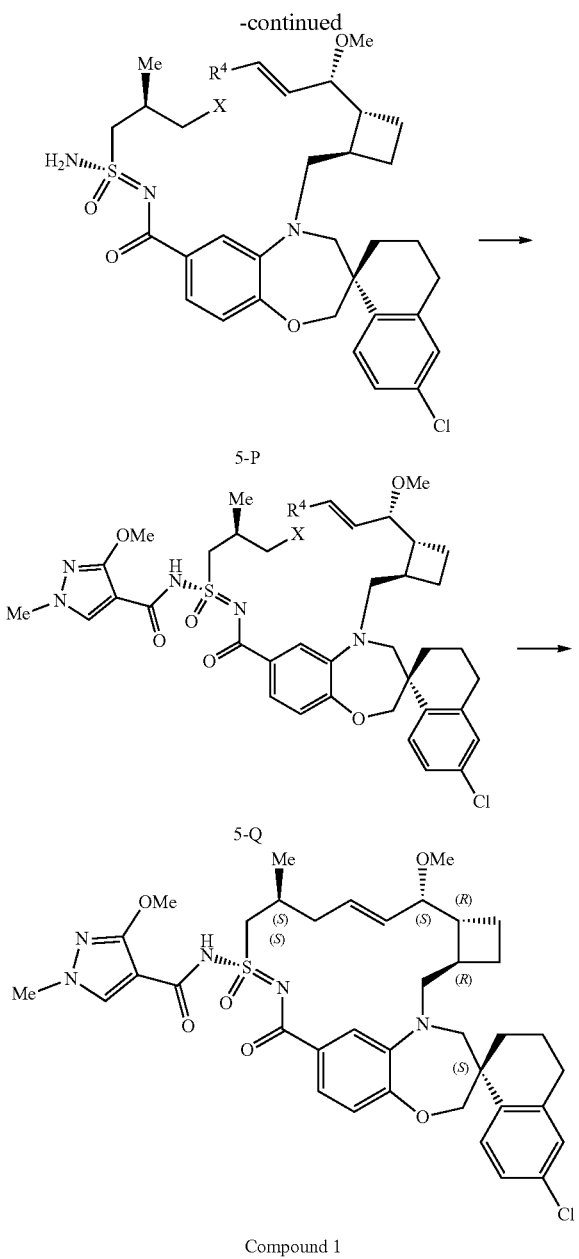

5-P

5-Q

Compound 1

In one embodiment, the present disclosure provides a method to prepare a compound 5-K from a compound 5-J.

In one embodiment, the method comprises the step of treating a compound 5-J with a promoter and an oxidant in a suitable solvent, for a time and under conditions effective to form a compound 5-K.

In one embodiment, the promoter is selected from Ruthenium chloride, potassium osmate, tungstophosphoric acid. In one embodiment, the promoter is Ruthenium chloride.

In one embodiment, the oxidant is selected from oxone, potassium permanganate, potassium periodate, lead tetraacetate, sodium hypochlorite, hydrogen peroxide, and sodium periodate. In one embodiment, the oxidant is sodium periodate.

In one embodiment, the solvent is selected from ethers (e.g., 2-methyltetrahydrofuran, tetrahydrofuran, methyl tert-butyl ether, cyclopentyl methyl ether), hydrocarbon solvents (e.g., toluene, n-heptane), halogenated solvents (e.g., dichloromethane, 1,2-dichloroethane, chloroform, chlorobenzene), alcohols (e.g., methanol, isopropanol, n-propanol), polar aprotic solvents (e.g., N,N-dimethylacetamide, N,N-dimethylformamide, N-methyl-2-pyrrolidinone, dimethyl sulfoxide), acetonitrile, and a combination thereof. In one embodiment, the solvent is a combination of acetonitrile and water.

In one embodiment, the temperature of the reaction is from −80 to 80° C. In one embodiment, the temperature is from −10 to 10° C.

In one embodiment, the present disclosure provides a method to prepare a compound 5-L from a compound 5-K.

In one embodiment, the method comprises the step of treating a compound 5-K with an acid in a suitable solvent, for a time and under conditions effective to form a compound 5-L.

In one embodiment, the acid is selected from acids such as p-toluenesulfonic acid, methanesulfonic acid, HCl, HBr or Lewis acids such as erbium(III) triflate. In one embodiment, the acid is methanesulfonic acid.

In one embodiment, the solvent is selected from ethers (e.g., 2-methyltetrahydrofuran, tert-butyl methyl ether, cyclopentyl methyl ether, polar aprotic solvents (e.g., dimethyl sulfoxide, N,N-dimethylformamide, N,N-dimethylacetamide, N-methyl-2-pyrrolidone), nitriles (e.g., acetonitrile), hydrocarbons (e.g., toluene, n-heptane), halogenated solvents (e.g., dichloromethane, 1,2-dichloroethane, chloroform, chlorobenzene), alcohols (e.g., 2-propanol), esters (e.g., ethyl acetate, isopropyl acetate), ketones (e.g., acetone, 2-butanone, 4-methyl-2-pentanone), water, and a combination thereof. In one embodiment, the solvent is a combination of tetrahydrofuran and water.

In one embodiment, the temperature of the reaction is from 0 to 100° C. In one embodiment, the temperature is from 60 to 70° C.

In one embodiment, the present disclosure provides a method to prepare a compound 5-M from a compound 5-L.

In one embodiment, the method comprises the step of treating a compound 5-L with a reducing agent in a suitable solvent, for a time and under conditions effective to form a compound 5-M.

In one embodiment, the reducing agent is selected from reductants such as tin or zinc in combination with acids such as hydrochloric acid, acetic acid, ammonium chloride, transition metal such as Pd or Rh in combination with $H_2$ or a formate salt, poisoned heterogeneous catalysts such as Pt/S/C, and iron powder. In one embodiment, the reducing agent is iron powder.

In one embodiment, the solvent is selected from acid (e.g., acetic acid, hydrogen chloride) in combination with other solvents including ethers (e.g., tetrahydrofuran, 2-methyltetrahydrofuran, methyl tert-butyl ether, cyclopentyl methyl ether), polar aprotic solvents (e.g., N,N-dimethylacetamide, N,N-dimethylformamide, N-methylpyrrolidinone, dimethyl sulfoxide), nitriles (e.g., acetonitrile), hydrocarbons (e.g., toluene, n-heptane), halogenated solvents (e.g., dichloromethane, 1,2-dichloroethane, chloroform, chlorobenzene), alcohols (e.g., 2-propanol), esters (e.g., ethyl acetate, isopropyl acetate), and a combination thereof. In one embodiment, the solvent is acetic acid.

In one embodiment, the temperature of the reaction is from 0 to 100° C. In one embodiment, the temperature is from 65 to 85° C.

In one embodiment, the present disclosure provides a method to prepare a compound 5-N from a compound 5-M.

In one embodiment, the present disclosure provides a method to prepare a compound 5-P from a compound 5-N and a compound 5-O.

In one embodiment, the present disclosure provides a method to prepare a compound 5-Q from a compound 5-P.

In one embodiment, the present disclosure provides a method of making a compound 1 from a compound selected from 5-K, 5-L, 5-M, 5-N, 5-P, and 5-Q, as shown in Scheme 5.

F. Method of Preparing Compound 1 from Formula 10-E

In one embodiment, the present disclosure provides a method of making a compound selected from 6-M, 6-N, 4-N, and compound 1, as shown in Scheme 6, wherein $R^x$ and $R^y$ are independently H, $C_{1-6}$alkyl, or $C_{6-10}$aryl, wherein the alkyl is optionally substituted with $C_{6-10}$aryl, $R^p$ is selected from —C(=O)—$C_{1-6}$alkyl, —C(=O)-heteroaryl, —C(=O)—O—$C_{1-6}$alkyl, and —C(=O)—O—$C_{1-6}$alkyl-$C_{6-10}$aryl, wherein each aryl or heteroaryl is optionally substituted with one to four groups independently selected from $C_{1-3}$alkyl and —O$C_{1-3}$alkyl, wherein each heteroaryl has one to four heteroatoms; wherein each heteroatom is independently selected from N, O, and S, and wherein each heteroaryl has 5 to 10 ring members.

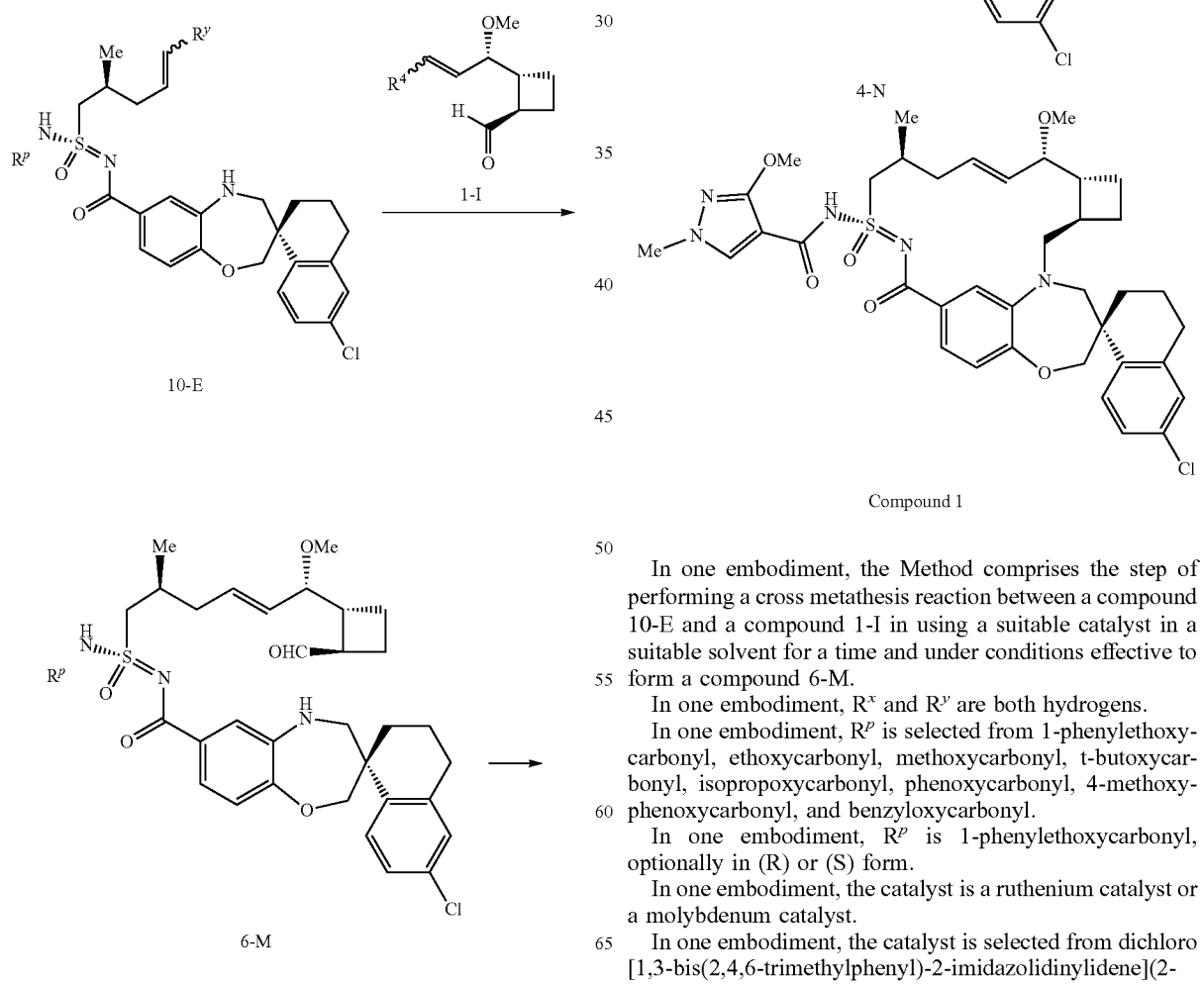

In one embodiment, the Method comprises the step of performing a cross metathesis reaction between a compound 10-E and a compound 1-I in using a suitable catalyst in a suitable solvent for a time and under conditions effective to form a compound 6-M.

In one embodiment, $R^x$ and $R^y$ are both hydrogens.

In one embodiment, $R^p$ is selected from 1-phenylethoxycarbonyl, ethoxycarbonyl, methoxycarbonyl, t-butoxycarbonyl, isopropoxycarbonyl, phenoxycarbonyl, 4-methoxyphenoxycarbonyl, and benzyloxycarbonyl.

In one embodiment, $R^p$ is 1-phenylethoxycarbonyl, optionally in (R) or (S) form.

In one embodiment, the catalyst is a ruthenium catalyst or a molybdenum catalyst.

In one embodiment, the catalyst is selected from dichloro [1,3-bis(2,4,6-trimethylphenyl)-2-imidazolidinylidene](2-isopropoxyphenylmethylene) ruthenium(II), dichloro(benzylidene)bis(tricyclohexylphosphine) ruthenium(II), dichloro[1,3-bis(2,4,6-trimethylphenyl)-2-imidazolidinylidene] (benzylidene) (tricyclohexylphosphine) ruthenium(II), dichloro(o-isopropoxyphenylmethylene)(tricyclohexylphosphine) ruthenium(II), dichloro[1,3-bis(2,4,6-trimethylphenyl)-2-imidazolidinylidene](2-isopropoxyphenylmethylene) ruthenium(II), dichloro[1,3-bis(2-methylphenyl)-2-imidazolidinylidene] (benzylidene) (tricyclohexylphosphine)ruthenium(II), dichloro[1,3-bis(2,4,6-trimethylphenyl)-2-imidazolidinylidene][3-(2-pyridinyl)propylidene]ruthenium(II), [1,3-dimesityl-2-imidazolidinylidene]dichloro(phenylmethylene)bis(3-bromopyridine)ruthenium(II), dichloro[1,3-bis(2,4,6-trimethylphenyl)-2-imidazolidinylidene](3-methyl-2-butenylidene) (tricyclohexylphosphine) ruthenium(II), dichloro[1,3-bis(2-methylphenyl)-2-imidazolidinylidene] (2-isopropoxyphenylmethylene)ruthenium(II), [1,3-dimesityl-2-imidazolidinylidene]dichloro[3-(2-pyridinyl)propylidene]-ruthenium(II), (1,3-dimesitylimidazolidin-2-ylidene)dichloro(2-isopropoxy-5-nitrobenzylidene) ruthenium(II), tricyclohexylphosphine[4,5-dimethyl-1,3-bis(2,4,6-trimethylphenyl) imidazol-2-ylidene][2-thienylmethylene] ruthenium(II) dichloride, tricyclohexylphosphine[1,3-bis(2,4,6-trimethylphenyl)imidazol-2-ylidene][2-thienylmethylene]ruthenium(II) dichloride, tricyclohexylphosphine[2,4-dihydro-2,4,5-triphenyl-3H-1,2,4-triazol-3-ylidene][2-thienylmethylene]ruthenium(II) dichloride, tricyclohexylphosphine[1,3-bis(2,4,6-trimethylphenyl)imidazol-2-ylidene][3-phenyl-1H-inden-1-ylidene]ruthenium(II) dichloride, and bis(tricyclohexylphosphine)-3-phenyl-1H-inden-1-ylideneruthenium(II) dichloride.

In one embodiment, the catalyst is selected from 2,6-diisopropyl-phenylimido-neophylidene[(S)-(–)-BIPHEN] molybdenum(VI), dichlorobis[(2,6-diisopropylphenyl)imido](1,2-dimethoxyethane)molybdenum(VI), and (T-4)-chloro(2,2-dimethylpropylidene)[2,2'',4,4',6,6'-hexakis(1-methylethyl)[1,1':3',1-terphenyl]-2'-olato][2-methyl-2-propanaminoato(2-)]molybdenum(VI).

In one embodiment, the suitable catalyst is the Hoveyda-Grubbs II catalyst (dichloro[1,3-bis(2,4,6-trimethylphenyl)-2-imidazolidinylidene](2-isopropoxyphenylmethylene)ruthenium(II)).

In one embodiment, the solvent is a nonpolar solvent or polar aprotic solvent.

In one embodiment, the solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane, anisole, trifluorotoluene, hexafluorobenzene, fluorobenzene, xylenes), and halogenated solvents (e.g., dichloromethane, 1,2-dichloroethane, chloroform, chlorobenzene).

In one embodiment, the polar aprotic solvent is selected from esters (e.g., ethyl acetate, methyl acetate, isopropyl acetate, butyl acetate, isobutyl acetate), ketones (e.g., acetone, methyl ethyl ketone, methyl isobutyl ketone, 2-pentanone), and carbonates (e.g., dimethyl carbonate, diethyl carbonate, diisopropyl carbonate).

In one embodiment, the temperature of the reaction is from 0 to 150° C.

In one embodiment, the temperature of the reaction is from 20 to 90° C.

In one embodiment, the temperature of the reaction is from 40 to 90° C.

In one embodiment, the temperature of the reaction is from 20 to 60° C.

In one embodiment, the temperature of the reaction is from 40 to 80° C.

In one embodiment, the temperature of the reaction is about 80° C.

In one embodiment, the method comprises the step of treating the compound 6-M in a suitable solvent with a reducing agent for a time and under conditions effective to form the tertiary amine compound 6-N.

In one embodiment, the reducing agent is selected from a hydride reducing agent, a silane reducing agent, or hydrogenation.

In one embodiment, the reducing agent is a hydride reducing agent.

In one embodiment, the hydride reducing agent is selected from sodium borohydride, lithium borohydride, sodium cyanoborohydride, zinc borohydride, sodium triacetoxyborohydride, and tetramethylammonium triacetoxyborohydride.

In one embodiment, the hydride reducing agent is sodium triacetoxyborohydride or sodium cyanoborohydride.

In one embodiment, the hydride reducing agent is combined with a reagent to modulate the hydride reducing activity (e.g., titanium isopropoxide, titanium ethoxide, borate salts, magnesium perchlorate, or zinc chloride).

In one embodiment, the silane reducing agent is triethylsilane.

In one embodiment, the reaction further comprises an acid (e.g., selected from acetic acid, trifluoracetic acid, citric acid, pivalic acid, p-toluenesulfonic acid, methanesulfonic acid, and hydrochloric acid).

In one embodiment, the suitable solvent is a nonpolar solvent, a polar protic solvent, or polar aprotic solvent.

In one embodiment, the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene).

In one embodiment, the polar protic solvent is selected from alcohols (e.g., methanol, ethanol, propanol, isopropanol) and acids (e.g., acetic acid, formic acid, trifluoroacetic acid).

In one embodiment, the polar aprotic solvent is selected from N,N-dimethylacetamide, N,N-dimethylformamide, N-methyl-2-pyrrolidinone, dimethyl sulfoxide, esters (e.g., methyl acetate, ethyl acetate, isopropyl acetate), and nitriles (e.g., acetonitrile).

In one embodiment, the suitable solvent is dichloromethane.

In one embodiment, the temperature of the reaction is from −30 to 80° C., e.g., from 0 to 80° C., or 10 to 30° C.

In one embodiment, the present disclosure provides a method to prepare a compound 4-N from a compound 6-N.

In one embodiment, the present disclosure provides a method of making a compound 1 from a compound selected from 10-E, 6-M, 6-N, and 4-N, as shown in Scheme 6.

G. Method of Preparing Compound 1 from Formula 7-A

In one embodiment, the present disclosure provides a method of making a compound selected from 7-C, 7-D, 7-E, 7-F, 4-N, and compound 1, as shown in Scheme 7, wherein $R^x$ and R are independently H, $C_{1-6}$alkyl, or $C_{6-10}$aryl, wherein the alkyl is optionally substituted with $C_{6-10}$aryl, $R^v$ is independently selected from H, $C_{1-6}$alkyl, $C_{1-6}$alkoxyn, halo, wherein said $C_{1-6}$ alkyl and $C_{1-6}$alkoxy is optionally substituted by 1-3 substituents selected from aryl, $C_{1-6}$alkyl, $C_{1-6}$alkoxy, and halo, $R^q$ is selected from a silyl group, an alkylcarbonyl group (e.g., —C(=O)—$C_{1-6}$ alkyl, such as acetyl, isobutyryl, pivaloyl, or —C(=O)—$C_{1-6}$alkyl(aryl), such as 2-phenylethylcarbonyl or 1-phenylethylcarbonyl), an arylcarbonyl group (e.g. benzoyl), an alkoxycarbonyl group (e.g., —C(=O)—O—$C_{1-6}$alkyl, such as methoxycarbonyl, ethoxycarbonyl, t-butoxycarbonyl, or benzyloxycarbonyl, or —C(=O)—O—$C_{1-6}$alkyl(aryl), such as 2-phenylethoxycarbonyl or 1-phenylethoxycarbonyl), an aryloxycarbonyl group (e.g., phenoxycarbonyl), a tertiary alkyl group (e.g., t-butyl or trityl), an $C_{1-6}$alkoxy$C_{1-6}$alkyl group (e.g., $C_{1-6}$alkoxymethyl, such as methoxymethyl or ethoxymethyl), a $C_{1-6}$alkylaryl group (e.g., benzyl, 3,5-dimethoxybenzyl, 1-methylbenzyl), a diarylalkyl group (e.g., $C_{1-6}$alkyl(aryl)(aryl), such as diphenylmethyl), an alkylsulfonyl group (e.g., $SO_2C_{1-6}$alkyl, such as methanesulfonyl or isopropylsulfonyl), and an arylsulfonyl group (e.g., $SO_2$-aryl, such as benzenesulfonyl, toluenesulfonyl), wherein each phenyl or heteroaryl is optionally substituted with one to four groups independently selected from $C_{1-3}$alkyl and —$OC_{1-3}$alkyl, wherein each heteroaryl has one to four heteroatoms, wherein each heteroatom is independently selected from N, O, and S, and wherein each heteroaryl has 5 to 10 ring members.

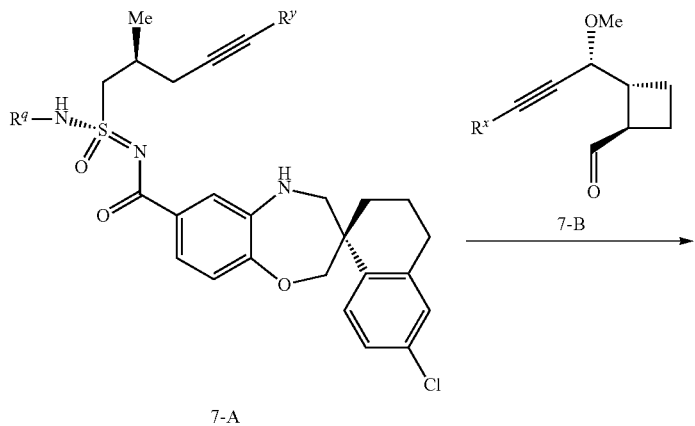

Scheme 7

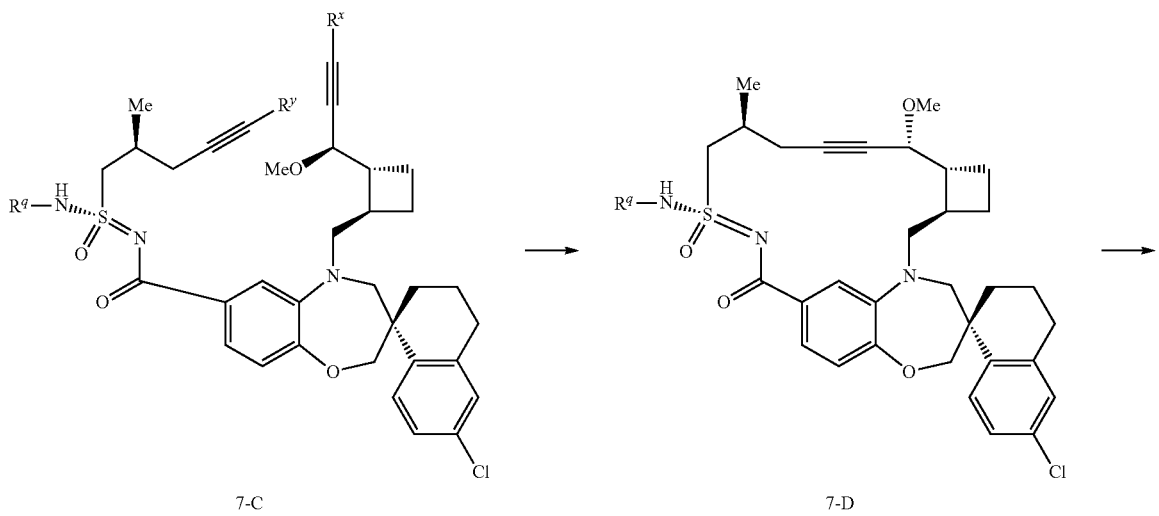

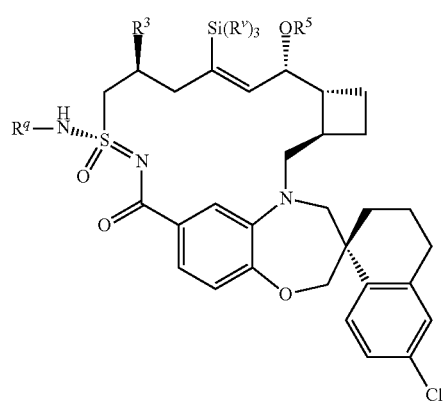

7-E

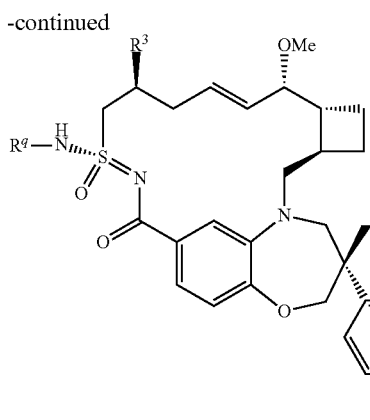

7-F

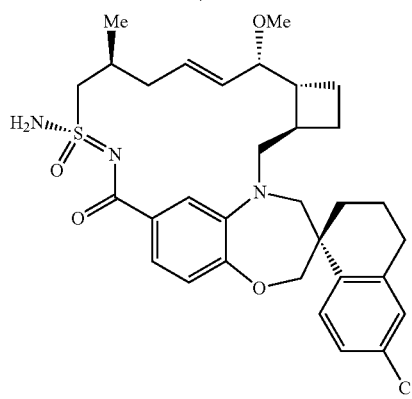

4-N

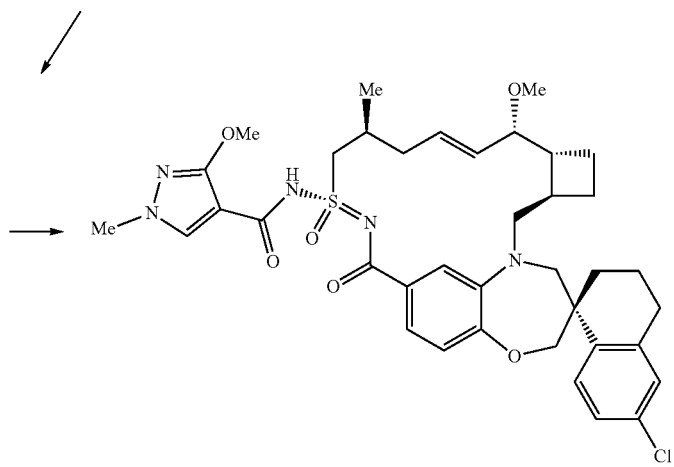

Compound 1

In one embodiment, the method comprises the step of treating a secondary amine compound 7-A with an aldehyde compound 7-B for a time and under conditions effective to form a tertiary amine compound 7-C, using a reducing agent in a suitable solvent.

In one embodiment, $R^x$ and $R^y$ are each H.

In one embodiment, $R^q$ is selected from —C(=O)—$C_{1-6}$alkyl (e.g., acetyl, isobutyryl, pivaloyl), —C(=O)-aryl (e.g. benzoyl), —C(=O)—O—$C_{1-6}$alkyl (e.g., methoxycarbonyl, ethoxycarbonyl, t-butoxycarbonyl, or benzyloxycarbonyl), —C(=O)—O—$C_{1-6}$alkyl(aryl) (e.g., 2-phenylethoxycarbonyl or 1-phenylethoxycarbonyl), and —C(=O)—O-aryl (e.g., phenoxycarbonyl).

In one embodiment, $R^q$ is selected from 1-phenylethoxycarbonyl, ethoxycarbonyl, methoxycarbonyl, t-butoxycarbonyl, isopropoxycarbonyl, phenoxycarbonyl, 4-methoxyphenoxycarbonyl, and benzyloxycarbonyl.

In one embodiment, $R^q$ is 1-phenylethoxycarbonyl, optionally in (R) or (S) form.

In one embodiment, $R^q$ is selected from a trialkyl silyl group (e.g., trimethylsilyl, triethylsilyl, tripropylsilyl, triisopropylsilyl, t-butyldimethylsilyl), a dialkylaryl silyl group (e.g., dimethylphenylsilyl), an alkyldiaryl silyl group (e.g., t-butyldiphenylsilyl), and a triarylsilyl group (e.g., triphenylsilyl).

In one embodiment, $R^q$ is selected from a tert-butyldiphenylsilyl group and a tert-butyldimethylsilyl group.

In one embodiment, the reducing agent is selected from a hydride reducing agent, a silane reducing agent, or a hydrogenation agent.

In one embodiment, the reducing agent is a hydride reducing agent.

In one embodiment, the hydride reducing agent is selected from sodium borohydride, lithium borohydride, sodium cyanoborohydride, zinc borohydride, sodium triacetoxyborohydride, and tetramethylammonium triacetoxyborohydride.

In one embodiment, the hydride reducing agent is sodium triacetoxyborohydride or sodium cyanoborohydride.

In one embodiment, the hydride reducing agent is combined with a reagent to modulate the hydride reducing activity (e.g., titanium isopropoxide, titanium ethoxide, borate salts, magnesium perchlorate, or zinc chloride).

In one embodiment, the silane reducing agent is triethylsilane.

In one embodiment, the reaction further comprises an acid. The acid is selected from acetic acid, trifluoroacetic acid, citric acid, pivalic acid, p-toluenesulfonic acid, methanesulfonic acid, and hydrochloric acid.

In one embodiment, the suitable solvent is a nonpolar solvent, a polar protic solvent, or polar aprotic solvent.

In one embodiment, the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene).

In one embodiment, the polar protic solvent is selected from alcohols (e.g., methanol, ethanol, propanol, isopropanol) and acids (e.g., acetic acid, formic acid, trifluoroacetic acid).

In one embodiment, the polar aprotic solvent is selected from N,N-dimethylacetamide, N,N-dimethylformamide, N-methyl-2-pyrrolidinone, dimethyl sulfoxide, esters (e.g., methyl acetate, ethyl acetate, isopropyl acetate), and nitriles (e.g., acetonitrile).

In one embodiment, the suitable solvent is tetrahydrofuran, dichloromethane or acetonitrile.

In one embodiment, the temperature of the reaction is from −30 to 80° C., e.g., from 0 to 80° C., or 10 to 30° C.

In one embodiment, the method comprises the step of performing a ring-closing alkyne metathesis on a compound 7-C for a time and under conditions effective to form a compound 7-D, using a suitable catalyst in a suitable solvent.

In one embodiment, the catalyst is a ruthenium catalyst or a molybdenum catalyst.

In one embodiment, the catalyst is selected from (SP-5-32)-nitrido(pyridine)tris(1,1,1-triphenylsilanolato)molybdenum(VI), [amidotris(2,3,4,5,6-pentafluorophenyl)borato(3-)-κN]bis(1,1,1-trimethylsilanolato)[1,1,1-trimethylsilyl)silanaminato]molybdenum(VI), (T-4)-tris(2-methyl-2-propanolato)nitridomolybdenum(VI), (T-4)-nitridobis(1,1,1-trimethylsilanolato)[1,1,1-trimethyl-N-(trimethylsilyl)silanaminato]molybdenum(VI), [amidotris(2,3,4,5,6-pentafluorophenyl)borato(3-)-κN]tris(1,1,1-triphenylsilanolato)molybdenum(IV), and molybdenum hexacarbonyl.

In one embodiment, the reaction further comprises an additive, e.g., 5 Å molecular sieves or 4-(trifluoromethyl)phenol.

In one embodiment, the solvent is a nonpolar solvent or polar aprotic solvent, or any combination thereof.

In one embodiment, the solvent is selected from ethers (e.g., tetrahydrofuran, 2-methyltetrahydrofuran, methyl tert-butyl ether, cyclopentyl methyl ether, dioxane), hydrocarbon solvents (e.g., benzene, toluene, n-hexane, n-heptane, anisole, trifluorotoluene, hexafluorobenzene, fluorobenzene, xylenes), and halogenated solvents (e.g., dichloromethane, 1,2-dichloroethane, chloroform, chlorobenzene, bromobenzene).

In one embodiment, the polar aprotic solvent is selected from esters (e.g., ethyl acetate, methyl acetate, isopropyl acetate, butyl acetate, isobutyl acetate), ketones (e.g., acetone, methyl ethyl ketone, methyl isobutyl ketone, 2-pentanone), and carbonates (e.g., dimethyl carbonate, diethyl carbonate, diisopropyl carbonate).

In one embodiment, the temperature of the reaction is from 0 to 150° C.

In one embodiment, the temperature of the reaction is from 20 to 90° C.

In one embodiment, the temperature of the reaction is from 40° C. to 90° C.

In one embodiment, the temperature of the reaction is from 20° C. to 60° C.

In one embodiment, the temperature of the reaction is from 40° C. to 80° C.

In one embodiment, the temperature of the reaction is about 80° C.

In one embodiment, the method comprises the step of hydrosilating a compound 7-D with a silane reagent and a catalyst in a suitable solvent for a time and under conditions effective to form a vinyl silane compound 7-E.

In one embodiment, each $R^v$ is independently selected from H, $C_{1-6}$alkyl (e.g., methyl, ethyl, isopropyl, propyl), $C_{1-6}$alkoxy (e.g., methoxy, ethoxy), halo (e.g., chloro, bromo); wherein said $C_{1-6}$alkyl and $C_{1-6}$alkoxy is optionally substituted by 1-3 substituents selected from aryl (e.g., phenyl), $C_{1-6}$alkyl, $C_{1-6}$alkoxy, and halo.

In one embodiment, $R^v$ is independently selected from methyl, ethyl, methoxy, ethoxy, benzyl, and chloro.

In one embodiment, the group $Si(R^v)_3$ is selected from trimethylsilyl, triethylsilyl, trimethoxysilyl, triethoxysilyl, benzyldimethylsilyl, chlorodimethylsilyl, and ethoxydimethylsilyl.

In one embodiment, the silane reagent is a reagent having the formula H—Si(R$^v$)$_3$.

In one embodiment, the silane reagent is selected from 1,1,3,3-tetramethyldisiloxane, trimethoxyhydrosilane, triethoxysilane, trimethylhydrosilane, benzyldimethylsilane, dimethylchlorosilane, ethoxy(dimethyl)silane, and triethylsilane.

In one embodiment, the catalyst is a ruthenium, rhodium, or platinum catalyst.

In one embodiment, the catalyst is selected from (tris(acetonitrile)(f-pentamethylcyclopentadienyl)ruthenium(II) hexafluorophosphate, benzenedichlororuthenium(II) dimer, dichloro(para-cymene)ruthenium(II) dimer, (bis(1,5-cyclooctadiene)rhodium(II) tetrafluoroborate hydrate, (biscyclo[2.2.21]hepta-2,5-diene)rhodium(I) chloride dimer, tris(triphenylphosphine)rhodium(I) chloride, chloroplatinic acid hydrate, and platinum(0)-1,3-divinyl-1,1,3,3-tetramethyldisiloxane complex.

In one embodiment, the solvent is a nonpolar solvent, polar protic, or polar aprotic solvent, or any combination thereof, or wherein the solvent is the neat silane reagent.

In one embodiment, the solvent is selected from ethers (e.g., tetrahydrofuran, 2-methyltetrahydrofuran, methyl tert-butyl ether, cyclopentyl methyl ether, or dioxane), hydrocarbon solvents (e.g., toluene, n-hexane, n-heptane, anisole, trifluorotoluene, hexafluorobenzene, fluorobenzene, or xylenes), and halogenated solvents (e.g., dichloromethane, 1,2-dichloroethane, chloroform, or chlorobenzene).

In one embodiment, the polar aprotic solvent is selected from N,N-dimethylformamide, N,N-dimethylacetamide, dimethylsulfoxide, N-methyl-2-pyrrolidone, sulfolane, esters (e.g., ethyl acetate, methyl acetate, isopropyl acetate, butyl acetate, or isobutyl acetate), ketones (e.g., acetone, methyl ethyl ketone, methyl isobutyl ketone, or 2-pentanone), and carbonates (e.g., dimethyl carbonate, diethyl carbonate, or diisopropyl carbonate).

In one embodiment, the polar protic solvent is an alcohol (e.g., methanol, ethanol, propanol, or isopropanol).

In one embodiment, the temperature of the reaction is from 0 to 100° C., e.g., from 20 to 80° C., or 40° C. to 80° C., or 20° C. to 60° C., or 50° C. to 90° C.

In one embodiment, the method comprises the step of deprotecting a compound 7-E with a suitable deprotection agent in a suitable solvent to provide either a compound 7-F or a compound 4-N.

In one embodiment, the deprotection agent is a fluoride agent.

In one embodiment, the fluoride agent is selected from sodium fluoride, potassium fluoride, potassium bifluoride, tetra-n-butylammonium fluoride, trietylamine trihydrofluoride, and hydrofluoric acid.

In one embodiment, the protecting group $R^q$ is a silyl protecting group and the product of the deprotection is a compound 4-N.

In one embodiment, the deprotection agent is an organic acid.

In one embodiment, the organic acid is selected from formic acid, trifluoroacetic acid, methanesulfonic acid, acetic acid, 4-toluenesulfonic acid, and trifluoromethanesulfonic acid.

In one embodiment, the protecting group $R^q$ is a silyl protecting group or a carbamate protecting group and the product of the deprotection is a compound 4-N.

In one embodiment, the solvent is a nonpolar solvent, polar protic, or polar aprotic solvent, or any combination thereof, or wherein the solvent is the neat deprotection reagent (e.g., an organic acid).

In one embodiment, the solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane, anisole, trifluorotoluene, hexafluorobenzene, fluorobenzene, xylenes), and halogenated solvents (e.g., dichloromethane, 1,2-dichloroethane, chloroform, chlorobenzene).

In one embodiment, the polar aprotic solvent is selected from N,N-dimethylformamide, N,N-dimethylacetamide, dimethylsulfoxide, N-methyl-2-pyrrolidone, sulfolane, esters (e.g., ethyl acetate, methyl acetate, isopropyl acetate, butyl acetate, isobutyl acetate), ketones (e.g., acetone, methyl ethyl ketone, methyl isobutyl ketone, 2-pentanone), and nitriles (e.g., acetonitrile).

In one embodiment, the polar protic solvent is an alcohol (e.g., methanol, ethanol, propanol, isopropanol), water, or a combination thereof.

In one embodiment, the temperature of the reaction is from 0 to 100° C., e.g., from 20 to 80° C., or 40° C. to 80° C., or 20° C. to 60° C., or 50° C. to 90° C.

In one embodiment, the method comprises the step of converting a compound 7-F to a compound 4-N.

In one embodiment, the method comprises the step of converting a compound 4-N to a Compound 1.

In one embodiment, the present disclosure provides a method of making a compound 1 from a compound selected from 7-A, 7-B, 7-C, 7-D, 7-E, 7-F, and 4-N, as shown in Scheme 7.

H. Method of Preparing Compound 1 from Formula 8-A

In one embodiment, the present disclosure provides a method of making a compound selected from 8-B, 8-C, 8-D, 8-E, 8-F, 6-N, and compound 1, as shown in Scheme 8, wherein $R^x$ and $R^y$ are independently H, $C_{1-6}$alkyl, or $C_{6-10}$aryl, wherein the alkyl is optionally substituted with $C_{6-10}$aryl, PG is selected from a silyl group, an alkylcarbonyl, arylcarbonyl group, an alkoxycarbonyl group, a silylalkoxycarbonyl group, an aryloxycarbonyl, or a $C_{1-6}$alkylaryl group, $R^p$ is selected from —C(=O)—$C_{1-6}$alkyl, —C(=O)-heteroaryl, —C(=O)—O—$C_{1-6}$alkyl, and —C(=O)—O—$C_{1-6}$alkyl-$C_{6-10}$aryl, wherein each aryl or heteroaryl is optionally substituted with one to four groups independently selected from $C_{1-3}$alkyl and —O$C_{1-3}$alkyl, wherein each heteroaryl has one to four heteroatoms; wherein each heteroatom is independently selected from N, O, and S, and wherein each heteroaryl has 5 to 10 ring members.

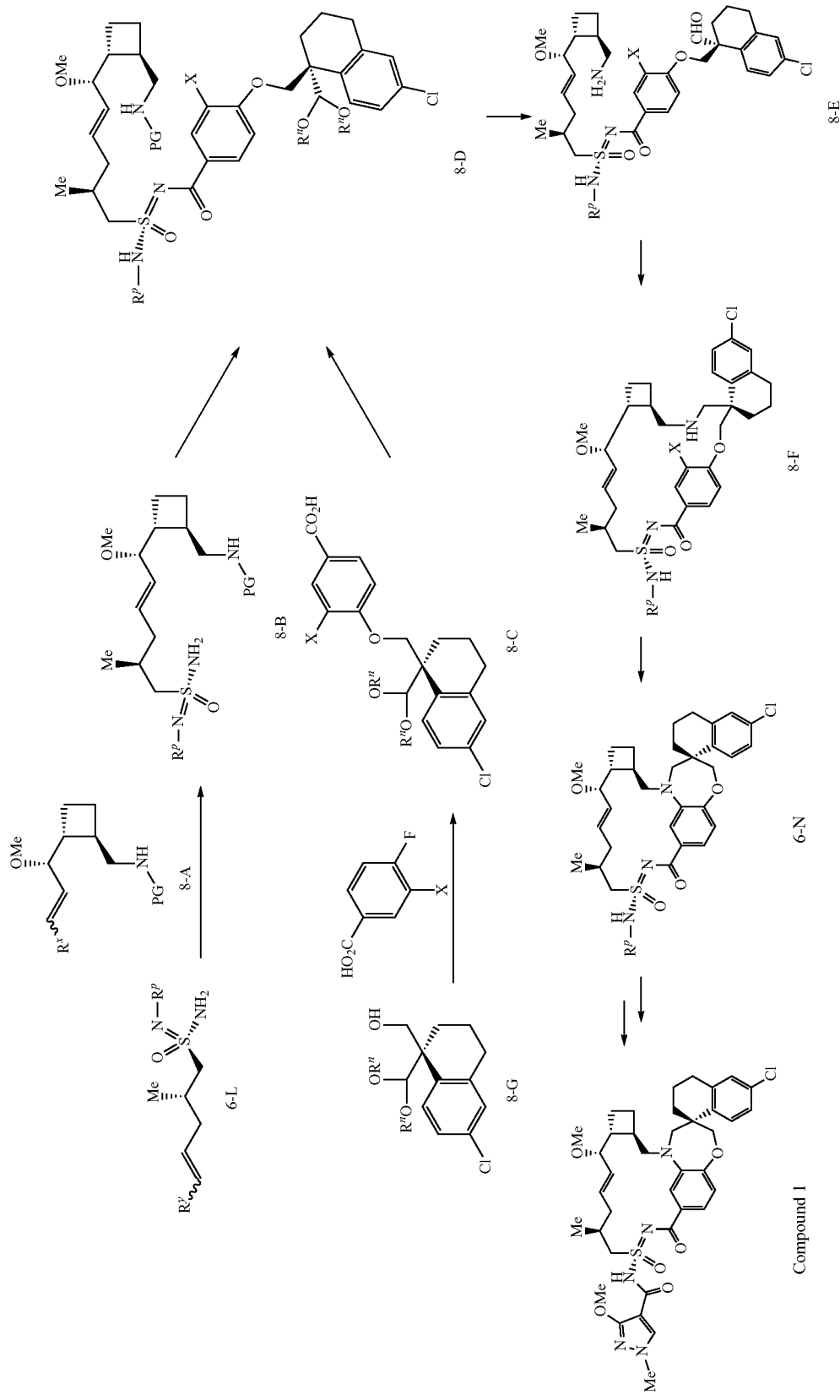

In one embodiment, the method comprises the step of reacting a compound 6-L with a compound 8-A in a cross-metathesis reaction, using a suitable catalyst in a suitable solvent, for a time and under conditions effective to form a compound 8-B3.

In one embodiment, PG is selected from a silyl group, an alkylcarbonyl group (e.g., —C(=O)—$C_{1-6}$alkyl, such as acetyl, isobutyryl, pivaloyl), arylcarbonyl group (e.g. benzoyl), an alkoxycarbonyl group (e.g., —C(=O)—O—$C_{1-6}$alkyl, such as methoxycarbonyl, ethoxycarbonyl, t-butoxycarbonyl, or benzyloxycarbonyl), a silylalkoxycarbonyl group (e.g., —C(=O)—O—$C_{1-6}$alkyl-Si($C_{1-6}$alkyl)$_3$, such as a 2-(trimethylsilyl)ethoxycarbonyl), an aryloxycarbonyl group (e.g., phenoxycarbonyl), or a $C_{1-6}$alkylaryl group (e.g., benzyl, 4-methoxybenzyl, 3,5-dimethoxybenzyl).

In one embodiment, PG is selected from a silyl group, an alkoxycarbonyl group (e.g., —C(=O)—O—$C_{1-6}$alkyl, such as methoxycarbonyl, ethoxycarbonyl, t-butoxycarbonyl, or benzyloxycarbonyl), a silylalkoxycarbonyl group (e.g., —C(=O)—O—$C_{1-6}$alkyl-Si($C_{1-6}$alkyl)$_3$, such as a 2-(trimethylsilyl)ethoxycarbonyl), or a $C_{1-6}$alkylaryl group (e.g., benzyl, 4-methoxybenzyl, 3,5-dimethoxybenzyl).

In one embodiment, the substituent PG is selected from a trialkyl silyl group (e.g., trimethylsilyl, triethylsilyl, tripropylsilyl, triisopropylsilyl, t-butyldimethylsilyl), a dialkylaryl silyl group (e.g., dimethylphenylsilyl), an alkyldiaryl silyl group (e.g., t-butyldiphenylsilyl), and a triarylsilyl group (e.g., triphenylsilyl).

In one embodiment, $R^x$ and $R^y$ are both hydrogens.

In one embodiment, $R^p$ is selected from 1-phenylethoxycarbonyl, ethoxycarbonyl, methoxycarbonyl, t-butoxycarbonyl, isopropoxycarbonyl, phenoxycarbonyl, 4-methoxyphenoxycarbonyl, and benzyloxycarbonyl.

In one embodiment, $R^p$ is 1-phenylethoxycarbonyl, optionally in (R) or (S) form.

In one embodiment, the suitable catalyst is a ruthenium catalyst or a molybdenum catalyst.

In one embodiment, the suitable catalyst is selected from dichloro[1,3-bis(2,4,6-trimethylphenyl)-2-imidazolidinylidene](2-isopropoxyphenylmethylene) ruthenium(II), dichloro(benzylidene)bis(tricyclohexylphosphine) ruthenium(II), dichloro[1,3-bis(2,4,6-trimethylphenyl)-2-imidazolidinylidene] (benzylidene) (tricyclohexylphosphine) ruthenium(II), dichloro(o-isopropoxyphenylmethylene) (tricyclohexylphosphine) ruthenium(II), dichloro[1,3-bis(2,4,6-trimethylphenyl)-2-imidazolidinylidene](2-isopropoxyphenylmethylene) ruthenium(II), dichloro[1,3-bis(2-methylphenyl)-2-imidazolidinylidene] (benzylidene) (tricyclohexylphosphine)ruthenium(II), dichloro[1,3-bis(2,4,6-trimethylphenyl)-2-imidazolidinylidene][3-(2-pyridinyl)propylidene]ruthenium(II), [1,3-dimesityl-2-imidazolidinylidene]dichloro(phenylmethylene)bis(3-bromopyridine)ruthenium(II), dichloro[1,3-bis(2,4,6-trimethylphenyl)-2-imidazolidinylidene](3-methyl-2-butenylidene) (tricyclohexylphosphine) ruthenium(II), dichloro[1,3-bis(2-methylphenyl)-2-imidazolidinylidene](2-isopropoxyphenylmethylene)ruthenium(II), [1,3-dimesityl-2-imidazolidinylidene]dichloro[3-(2-pyridinyl)propylidene]-ruthenium(II), (1,3-dimesitylimidazolidin-2-ylidene)dichloro(2-isopropoxy-5-nitrobenzylidene) ruthenium(II), tricyclohexylphosphine[4,5-dimethyl-1,3-bis(2,4,6-trimethylphenyl) imidazol-2-ylidene][2-thienylmethylene] ruthenium(II) dichloride, tricyclohexylphosphine[1,3-bis(2,4,6-trimethylphenyl)imidazol-2-ylidene][2-thienylmethylene]ruthenium(II) dichloride, tricyclohexylphosphine[2,4-dihydro-2,4,5-triphenyl-3H-1,2,4-triazol-3-ylidene][2-thienylmethylene]ruthenium(II) dichloride, tricyclohexylphosphine[1,3-bis(2,4,6-trimethylphenyl)imidazol-2-ylidene][3-phenyl-1H-inden-1-ylidene]ruthenium(II) dichloride, and bis(tricyclohexylphosphine)-3-phenyl-1H-inden-1-ylideneruthenium(II) dichloride.

In one embodiment, the catalyst is selected from 2,6-diisopropyl-phenylimido-neophylidene[(S)-(−)-BIPHEN] molybdenum(VI), dichlorobis[(2,6-diisopropylphenyl)imido](1,2-dimethoxyethane)molybdenum(VI), and (T-4)-chloro(2,2-dimethylpropylidene)[2,2″,4,4′,6,6′-hexakis(1-methylethyl)[1,1′:3′,1-terphenyl]-2′-olato][2-methyl-2-propanaminoato(2-)]molybdenum(VI).

In one embodiment, the suitable catalyst is the Hoveyda-Grubbs II catalyst (dichloro[1,3-bis(2,4,6-trimethylphenyl)-2-imidazolidinylidene](2-isopropoxyphenylmethylene)ruthenium(II)).

In one embodiment, the suitable solvent is a nonpolar solvent or polar aprotic solvent.

In one embodiment, the solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane, anisole, trifluorotoluene, hexafluorobenzene, fluorobenzene, xylenes), and halogenated solvents (e.g., dichloromethane, 1,2-dichloroethane, chloroform, chlorobenzene).

In one embodiment, the polar aprotic solvent is selected from esters (e.g., ethyl acetate, methyl acetate, isopropyl acetate, butyl acetate, isobutyl acetate), ketones (e.g., acetone, methyl ethyl ketone, methyl isobutyl ketone, 2-pentanone), and carbonates (e.g., dimethyl carbonate, diethyl carbonate, diisopropyl carbonate).

In one embodiment, the temperature of the reaction is from 0 to 150° C., e.g., from 0 to 120° C. e.g., from 20 to 90° C., or from 40 to 90° C., or from 20 to 60° C., or from 40 to 80° C., or about 80° C.

In one embodiment, the method comprises the step of treating a compound 8-G with a 4-fluoro-5-X-benzoic acid, wherein X is selected from bromo, chloro, iodo, sulfonate (e.g., trifluoromethanesulfonate, methylsulfonate, p-toluenesulfonate, imidazolylsulfonate) and phosphinate (e.g., diphenyl phosphinate), for a time and under conditions effective to form an ether adduct compound 8-C, wherein each $R''$ is independently $C_{1-6}$alkyl (e.g., methyl, ethyl or isopropyl), or wherein the two $R''$ moieties join together to form a $C_{2-10}$ alkyl or $C_{2-10}$ alkenyl bridge (i.e., a cyclic acetal), wherein said bridge is optionally substituted by one to four $C_{1-6}$ alkyl, halo or aryl; or wherein the two $R''$ moieties join together to form an optionally substituted 1,2-hydroxyaryl bridge (e.g., a catechol bridge).

In one embodiment, $R''$ moieties of the compound 8-G are methyl or ethyl, or the two $R''$ moieties of the compound 8-G join together to form a bridge selected from —CH$_2$CH$_2$—, —CH(CH$_3$)CH(CH$_3$)—, —CH$_2$CH(CH$_3$)—, —CH$_2$CH(C$_6$H$_5$)—, —C(CH$_3$)$_2$C(CH$_3$)$_2$—, —CH$_2$CH$_2$CH$_2$—, —CH$_2$CBr$_2$CH$_2$—, —CH$_2$(C=CH)CH$_2$—, —CH$_2$CH(C$_6$H$_5$)CH$_2$—, —CH(CH$_3$)CH$_2$CH(CH$_3$)—, —CH$_2$CH(CH$_3$)CH$_2$—, —CH$_2$C(CH$_3$)$_2$CH$_2$—, —CH$_2$C(CH$_2$CH$_3$)$_2$CH$_2$—, —CH$_2$CH$_2$CH$_2$CH$_2$—, —CH$_2$CH$_2$CH$_2$CH$_2$CH$_2$—, —CH(C$_6$H$_5$)CH(C$_6$H$_5$), —CH$_2$CH(C$_6$H$_5$)CH$_2$—, and -(o-C$_6$H$_4$)—.

In one embodiment, the compound 8-G is dissolved or suspended in the suitable solvent and treated with a strong base, and optionally with a promoter (e.g., sodium iodide, tetrabutylammonium iodide).

In one embodiment, the base is selected from inorganic hydrides (e.g., sodium hydride, potassium hydride), alkoxides (e.g., sodium methoxide, sodium ethoxide, sodium t-butoxide, potassium methoxide, potassium ethoxide, potassium t-butoxide, lithium t-butoxide, potassium t-pentoxide, sodium t-pentoxide, lithium t-pentoxide), inorganic hydroxides (e.g., sodium hydroxide, potassium hydroxide, lithium hydroxide), amide bases (sodium hexamethyldisilazide, lithium hexamethyldisilazide, potassium hexamethyldisilazide, lithium diisopropylamide, sodium diisopropylamide, potassium diisopropylamide), organolithium bases (e.g., methyllithium, ethyllithium, butyllithium, s-butyl lithium t-butyllithium), Grignard agents (e.g., methyl, ethyl, propyl, isopropyl or butyl magnesium chlorides or bromides), and inorganic bases (e.g., lithium carbonate, sodium carbonate, potassium carbonate, cesium carbonate, potassium phosphate (mono-, di- or tri-basic), sodium phosphate (mono-, di- or tri-basic)).

In one embodiment, the suitable solvent is a nonpolar solvent or polar aprotic solvent.

In one embodiment, the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane, benzene, trifluorotoluene, benzonitrile, xylenes), and halogenated solvents (e.g., dichloromethane, 1,2-dichloroethane, chloroform, chlorobenzene).

In one embodiment, the polar aprotic solvent is selected from formamide, N,N-dimethylformamide, N,N-dimethylacetamide, dimethylsulfoxide, N-methyl-2-pyrrolidone, sulfolane, esters (e.g., methyl acetate, ethyl acetate, n-butyl acetate, isopropyl acetate, isobutyl acetate), ketones (e.g., acetone, methyl ethyl ketone, methyl butyl ketone, 2-propanone, 3-pentanone), and nitriles (e.g., acetonitrile, propionitrile, benzonitrile).

In one embodiment, the temperature of the reaction is from −80 to 120° C., e.g., from −45 to 10° C., or from −30 to 10° C., or from −10 to 5° C., or about 0° C., or from −10 to 50° C., or from −10 to 30° C., or from 10 to 30° C., or from 25 to 120° C., or from 50 to 80° C.

In one embodiment, the method comprises the step of acylating a compound 8-B with a benzoic acid compound 8-C, using an acid activator and a base in a suitable solvent, for a time and under conditions effective to form a compound 8-D.

In one embodiment, the acid activator is selected from N-(3-dimethylaminopropyl)-N'-ethylcarbodiimide hydrochloride (EDC-HCl), (PhO)$_2$POCl, carbonyldiimidazole (CDI), propylphosphonic anhydride (T3P), 1-[bis(dimethylamino)methylene]-1H-1,2,3-triazolo[4,5-b]pyridinium 3-oxide hexafluorophosphate (HATU), 4-(4,6-dimethoxy-1,3,5-triazin-2-yl)-4-methyl-morpholinium chloride (DMTMM), thionyl chloride, oxalyl chloride, sulfuryl chloride, isobutyl chloroformate, N,N,N'N'-tetramethylchloroformamidinium hexafluorophosphate, 2,4,6-trichlorobenzoyl chloride, N,N'-diisopropylcarbodiimide, and N,N'-dicyclohexylcarbodiimide.

In one embodiment, the acid activator is N-(3-dimethylaminopropyl)-N'-ethylcarbodiimide hydrochloride (EDC-HCl).

In one embodiment, the base is selected from tertiary amines (e.g., trimethylamine, triethylamine, N-methylmorpholine, N-ethylmorpholine, tripropylamine, N,N-diisopropylethylamine, tributylamine, 1,8-diazabicyclo[5.4.0]undec-7-ene, 1,4-diazabicyclo[2.2.2]octane, N-methylpyrrolidine), aromatic amines (e.g., pyridine, 2,6-lutidine, picoline, collidine, imidazole, 1-methylimidazole, indole, isoindole, quinoline, isoquinoline, 4-dimethylaminopyridine), hydroxides (e.g., sodium hydroxide, potassium hydroxide, tetrabutylammonium hydroxide), and inorganic bases (e.g., lithium carbonate, sodium carbonate, potassium carbonate, cesium carbonate, sodium bicarbonate, potassium phosphate (monobasic, dibasic or tribasic), and sodium phosphate (monobasic, dibasic or tribasic)).

In one embodiment, the reaction further comprises a promoter selected from dichloromethylene-dimethyliminium chloride, 4-dimethylaminopyridine (DMAP), N-methylimidazole, 1-hydroxy-7-azabenzotriazole (HOAt), and 1-hydroxybenzotriazole (HOBt).

In one embodiment, the acid activator is EDC-HCl, the base is 1-methylimidazole and the promoter is DMAP.

In one embodiment, the suitable solvent is a nonpolar solvent or polar aprotic solvent, or a combination thereof, optionally comprising water or a biphasic reaction.

In one embodiment, the nonpolar solvent is selected from ethers (e.g., diethyl ether, tetrahydrofuran, 2-methyltetrahydrofuran, methyl tert-butyl ether, cyclopentyl methyl ether, dioxane), hydrocarbon solvents (e.g., toluene, n-hexane, n-heptane, benzene, xylenes), and halogenated solvents (e.g., dichloromethane, 1,2-dichloroethane, chloroform, chlorobenzene).

In one embodiment, the polar aprotic solvent is selected from N,N-dimethylformamide, N,N-dimethylacetamide, N-methyl-2-pyrrolidinone, dimethyl sulfoxide, sulfolane, esters (e.g., ethyl acetate, methyl acetate, isopropyl acetate, butyl acetate, isobutyl acetate), carbonates (e.g., dimethyl carbonate, diethyl carbonate), and nitriles (e.g., acetonitrile).

In one embodiment, the temperature of the reaction is from −50 to 60° C., e.g., from 0 to 60° C., or from 10 to 40° C., or from 20 to 40° C.

In one embodiment, the method comprises the step of treating a compound 8-D with a deprotection agent in a suitable solvent for a time and under conditions effective to form a compound 8-E.

In one embodiment, PG is selected from a silyl group, an alkoxycarbonyl group (e.g., —C(=O)—O—C$_{1-6}$alkyl, such as methoxycarbonyl, ethoxycarbonyl, t-butoxycarbonyl, or benzyloxycarbonyl), a silylalkoxycarbonyl group (e.g., —C(=O)—O—C$_{1-6}$alkyl-Si(C$_{1-6}$alkyl)$_3$, such as a 2-(trimethylsilyl)ethoxycarbonyl), or a C$_{1-6}$alkylaryl group (e.g., benzyl, 4-methoxybenzyl, 3,5-dimethoxybenzyl).

In one embodiment, the substituent PG is selected from a trialkyl silyl group (e.g., trimethylsilyl, triethylsilyl, tripropylsilyl, triisopropylsilyl, t-butyldimethylsilyl), a dialkylaryl silyl group (e.g., dimethylphenylsilyl), an alkyldiaryl silyl group (e.g., t-butyldiphenylsilyl), and a triarylsilyl group (e.g., triphenylsilyl).

In one embodiment, R$^p$ is selected from 1-phenylethoxycarbonyl, ethoxycarbonyl, methoxycarbonyl, t-butoxycarbonyl, isopropoxycarbonyl, phenoxycarbonyl, 4-methoxyphenoxycarbonyl, and benzyloxycarbonyl.

In one embodiment, R$^p$ is 1-phenylethoxycarbonyl, optionally in (R) or (S) form.

In one embodiment, the deprotection reagent is selected from an inorganic base (e.g., an aqueous solution thereof), an acid (e.g., an aqueous solution thereof or a solution in an organic solvent), a fluoride agent (e.g., in an organic solvent), a hydrogenation agent (e.g., hydrogen in combination with a heterogenous catalyst (e.g., a transition metal catalyst) or a homogeneous catalyst (e.g., a soluble transition metal complex), or a phase transfer hydrogenation system), optionally further comprising a phase transfer agent.

In one embodiment, the deprotection agent is a fluoride agent or an acid.

In one embodiment, the deprotection reagent is selected from hydrochloric acid (e.g., aqueous HCl, HCl in ether, HCl in methanol, HCl in isopropanol), hydrobromic acid (e.g., aqueous HBr), sulfuric acid, formic acid, acetic acid, trifluoroacetic acid, phosphoric acid, methanesulfonic acid, 4-toluenesulfonic acid, hydrofluoric acid, hydrogen fluoride pyridine, hydrogen fluoride triethylamine, potassium fluoride, sodium fluoride, lithium fluoride, cesium fluoride, potassium bifluoride, tetramethylammonium fluoride, tetraethylammonium fluoride, and tetrabutylammonium fluoride.

In one embodiment, the suitable solvent is a nonpolar solvent, polar protic solvent, or polar aprotic solvent, or a mixture thereof, optionally comprising water as a biphasic reaction.

In one embodiment, the nonpolar solvent is selected from ethers (e.g., diethyl ether, tetrahydrofuran, 2-methyltetrahydrofuran, methyl tert-butyl ether, cyclopentyl methyl ether, dioxane), hydrocarbon solvents (e.g., toluene, n-hexane, n-heptane, benzene, xylenes), and halogenated solvents (e.g., dichloromethane, 1,2-dichloroethane, chloroform, chlorobenzene).

In one embodiment, the polar protic solvent is an alcoholic solvent (e.g., methanol, ethanol, propanol, isopropanol, tert-butanol, tert-amyl alcohol), optionally in combination with water, or wherein the polar protic solvent is water.

In one embodiment, the polar aprotic solvent is selected from N,N-dimethylacetamide, N,N-dimethylformamide, N-methyl-2-pyrrolidinone, and dimethyl sulfoxide, sulfolane, nitriles (e.g., acetonitrile, propionitrile), and esters (methyl acetate, ethyl acetate, isopropyl acetate, butyl acetate, isobutyl acetate, dimethylcarbonate).

In one embodiment, the temperature of the reaction is from −15 to 60° C., e.g., from 0° C. to 60° C., or from −5 to 40° C., or from 0° C. to 30° C., or from 10° C. to 30° C.

In one embodiment, the method comprises the step of treating a compound 8-E with a reducing agent in a suitable solvent, for a time and under conditions effective to form a compound 8-F.

In one embodiment, the reducing agent is selected from a hydride reducing agent, a silane reducing agent, or hydrogenation.

In one embodiment, the reducing agent is a hydride reducing agent.

In one embodiment, the hydride reducing agent is selected from sodium borohydride, lithium borohydride, sodium cyanoborohydride, zinc borohydride, sodium triacetoxyborohydride, and tetramethylammonium triacetoxyborohydride.

In one embodiment, the hydride reducing agent is sodium triacetoxyborohydride or sodium cyanoborohydride.

In one embodiment, the hydride reducing agent is combined with a reagent to modulate the hydride reducing activity (e.g., titanium isopropoxide, titanium ethoxide, borate salts, magnesium perchlorate, or zinc chloride).

In one embodiment, the silane reducing agent is triethylsilane.

In one embodiment, the reaction further comprises an acid (e.g., selected from acetic acid, trifluoracetic acid, citric acid, pivalic acid, p-toluenesulfonic acid, methanesulfonic acid, and hydrochloric acid).

In one embodiment, the suitable solvent is a nonpolar solvent, a polar protic solvent, or polar aprotic solvent.

In one embodiment, the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene).

In one embodiment, the polar protic solvent is selected from alcohols (e.g., methanol, ethanol, propanol, isopropanol) and acids (e.g., acetic acid, formic acid, trifluoracetic acid).

In one embodiment, the polar aprotic solvent is selected from N,N-dimethylacetamide, N,N-dimethylformamide, N-methyl-2-pyrrolidinone, dimethyl sulfoxide, esters (e.g., methyl acetate, ethyl acetate, isopropyl acetate), and nitriles (e.g., acetonitrile).

In one embodiment, the suitable solvent is tetrahydrofuran, dichloromethane or acetonitrile.

In one embodiment, the temperature of the reaction is from −30 to 80° C., e.g., from −30 to 50° C., or from 0 to 50° C., or from 10 to 30° C.

In one embodiment, the method comprises the step of treating a compound 8-F with a base and optionally a catalyst, and optionally a ligand, in a suitable solvent, for a time and under conditions effective to form a compound 6-N.

In one embodiment, the base is selected from inorganic bases (e.g., lithium carbonate, sodium carbonate, potassium carbonate, and cesium carbonate, sodium or potassium phosphate (each in mono-basic, di-basic or tri-basic form)), organic bases (e.g., alkali metal carboxylates, such as sodium or potassium acetates, pivalates, or propionates), hydroxides, (e.g., lithium hydroxide, sodium hydroxide, tertrabutylammonium hydroxide), and alkoxides (e.g., sodium tert-butoxide, potassium tert-butoxide, sodium t-pentoxide).

In one embodiment, the reaction further comprises a catalyst, e.g., selected from palladium(II) acetate, palladium (II) pivalate, palladium (II) propionate, palladium (II) trifluoroacetate, palladium (II) bromide, palladium (II) chloride, tris(dibenzylideneacetone)dipalladium(0), (SP-4-3)-[(2R)-1-[(1R)-1-[bis(1,1-dimethylethyl)phosphino-κP] ethyl]-2-(dicyclohexylphosphino-κP)ferrocene] dichloropalladium(II), (2-dicyclohexylphosphino-2',4',6'-triisopropyl-1,1'-biphenyl)[2-(2'-amino-1,1'-biphenyl)] palladium(II) methanesulfonate, [(2-di-tert-butylphosphino-3,6-dimethoxy-2',4',6'-triisopropyl-1,1'-biphenyl)-2-(2'-amino-1,1'-biphenyl)]palladium(II) methanesulfonate, (2-dicyclohexylphosphino-2',6'-dimethoxybiphenyl) [2-(2'-amino-1,1'-biphenyl)]palladium(II) methanesulfonate, [(di (1-adamantyl)-butylphosphine)-2-(2'-amino-1,1'-biphenyl)] palladium(II) methanesulfonate, [(2-di-cyclohexylphosphino-3,6-dimethoxy-2',4',6'-triisopropyl-1,1'-biphenyl)-2-(2'-amino-1,1'-biphenyl)]palladium(II) methanesulfonate, [(2-di-tert-butylphosphino-2',4',6'-triisopropyl-1,1'-biphenyl)-2-(2'-amino-1,1'-biphenyl)] palladium(II) methanesulfonate, [(1,3,5,7-tetramethyl-6-phenyl-2,4,6-trioxa-6-phosphaadamantane)-2-(2'-amino-1,1'-biphenyl)]palladium(II) methanesulfonate, [(2-{bis[3,5-bis (trifluoromethyl)phenyl]phosphine}-3,6-dimethoxy-2',4',6'-triisopropyl-1,1'-biphenyl)-2-(2'-amino-1,1'-biphenyl)] palladium(II) methanesulfonate, [(2-dicyclohexylphosphino-2',6'-bis(N,N-dimethylamino)-1,1'-biphenyl)-2-(2'-amino-1,1'-biphenyl)] palladium(II) methanesulfonate, (2-dicyclohexylphosphino-2',6'-diisopropoxy-1,1'-biphenyl)[2-(2'-amino-1,1'-biphenyl)]palladium(II) methanesulfonate, [(2-di-tert-butylphosphino-3-methoxy-6-methyl-2',4',6'-triisopropyl-1,1'-biphenyl)-2-(2-aminobiphenyl)]palladium(II) methanesulfonate, [2-(di-1-adamantylphosphino)-2',4',6'-triisopropyl-3,6-dimethoxybiphenyl][2-(2'-amino-1,1'-biphenyl)]palladium (II) methanesulfonate, [(di-tert-butylneopentylphosphine)-2-(2-aminobiphenyl)]palladium(II) methanesulfonate, mesyl(2-(di-tert-butylphosphino)-1,1'-binaphthyl)[2-(2'-amino-1,1'-biphenyl)]palladium(II), methanesulfonato (di-tert-butyl) methylphosphino (2'-amino-1,1'-biphenyl-2-yl) palladium(II), and methanesulfonato 2-dicyclohexylphosphino-2-(N,N-dimethylamino)biphenyl(2'-amino-1,1'-biphenyl-2-yl) palladium(II).

In one embodiment, the reaction further comprises a ligand, e.g., selected from triphenylphosphine, tri-orthotolylphosphine, tri-tert-butylphosphine, di-tert-butyl-(methyl)phosphine, di-tert-butyl(phenyl)phosphine, tricyclohexylphosphine, tri-isopropylphosphine, n-butyldiadamantylphosphine, 2,2'-bis(diphenylphosphino)-

1,1'-binaphthyl, 4,5-bis(diphenylphosphino)-9,9-dimethyl-xanthene, bis[(2-diphenylphosphino)phenyl] ether, 1,1'-bis (diphenlphosphino)ferrocene, (2R)-1-[(1R)-1-[bis(1,1-dimethylethyl)phosphino]ethyl]-2-(dicyclohexylphosphino) ferrocene, 1,3-bis(diphenylphosphino)propane, 5-(di-tert-butylphosphino)-1',3',5'-triphenyl-1'H-[1,4']bipyrazole, di(1-adamantyl)-2-morpholinophenylphosphine, N,N'-(2,6-diisopropylphenyl)dihydroimidazolium chloride, (2-biphenyl)di-tert-butylphosphine, (2-biphenylyl)di-tert-butylphosphine, 2-(di-tert-butylphosphino)biphenyl, (2-biphenyl) dicyclohexylphosphine, 2-dicyclohexylphosphino-2'-(N,N-dimethylamino)biphenyl, 2-dicyclohexylphosphino-2',6'-diisopropoxybiphenyl, 2-dicyclohexylphosphino-2',6'-dimethoxybiphenyl, 2-dicyclohexylphosphino-2',4',6'-triisopropylbiphenyl, 2-(dicyclohexylphosphino)3,6-dimethoxy-2',4',6'-triisopropyl-1,1'-biphenyl, 2-di-tert-butylphosphino-2',4',6'-triisopropylbiphenyl, 2-(di-tert-butylphosphino)-2',4',6'-triisopropyl-3,6-dimethoxy-1,1'-biphenyl, and 2-di-tert-butylphosphino-3,4,5,6-tetramethyl-2',4',6'-triisopropyl-1,1'-biphenyl.

In one embodiment, the suitable solvent is a nonpolar solvent, a polar protic solvent, or polar aprotic solvent.

In one embodiment, the nonpolar solvent is selected from ethers (e.g., tetrahydrofuran, 2-methyltetrahydrofuran, methyl tert-butyl ether, cyclopentyl methyl ether, dioxane, dimethoxyethane), hydrocarbon solvents (e.g., toluene, n-hexane, n-heptane, benzene, trifluorotoluene, xylenes), and halogenated solvents (e.g., dichloromethane, 1,2-dichloroethane, chloroform, chlorobenzene).

In one embodiment, the polar protic solvent is an alcohol (e.g., methanol, ethanol, propanol, isopropanol, butanol, tert-butanol, 2-methyl-2-butanol).

In one embodiment, the polar aprotic solvent is selected from N,N-dimethylacetamide, N,N-dimethylformamide, N-methyl-2-pyrrolidinone, dimethyl sulfoxide, sulfolane, and nitriles (e.g., acetonitrile, propionitrile, benzonitrile).

In one embodiment, the suitable solvent is tetrahydrofuran, dichloromethane or acetonitrile.

In one embodiment, the temperature of the reaction is from 25 to 120° C., e.g., from 40 to 100° C., or from 60 to 80° C.

In one embodiment, the method produces a compound according to one or more of Compounds 8-B, 8-C, 8-D, 8-E, 8-F, or 6-N.

In one embodiment, wherein the product compound 6-N is further elaborated to a compound 4-N or Compound 1.

In one embodiment, the present disclosure provides a method of making a Compound 1 from a compound selected from 8-A, 6-L, 8-B, 8-C, 8-D, 8-E, 8-F, 8-G, and 6-N, as shown in Scheme 8.

I. Method of Preparing Compound 1 from Formula 9-G

In one embodiment, the present disclosure provides a method of making a compound selected from 9-H, 9-I, 9-J, and compound 1, as shown in Scheme 9, wherein $R^2$ is H, $R^3$ and $R^5$ are each independently $CH_3$, $R^{12}$ is

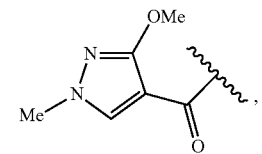 [SMILES: *C(=O)c1cn(C)nc1OC]

$R^u$ and $R^w$ are each independently H, $C_{1-6}$alkyl, or $C_{6-10}$aryl, wherein the alkyl is optionally substituted with $C_{6-10}$aryl, $R^p$ is selected from —C(=O)—$C_{1-6}$alkyl, —C(=O)-heteroaryl, —C(=O)—O—$C_{1-6}$alkyl, and —C(=O)—O—$C_{1-6}$alkyl-$C_{6-10}$aryl, wherein each aryl or heteroaryl is optionally substituted with one to four groups independently selected from $C_{1-3}$alkyl and —$OC_{1-3}$alkyl, wherein each heteroaryl has one to four heteroatoms, wherein each heteroatom is independently selected from N, O, and S, and wherein each heteroaryl has 5 to 10 ring members. In one embodiment, $R^u$ is H. In one embodiment, $R^w$ is H. In one embodiment, $R^p$ is 1-phenylethoxycarbonyl. In one embodiment, $R^p$ is

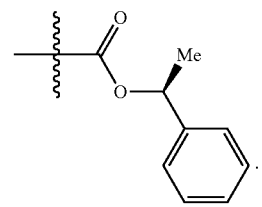 [SMILES: *C(=O)O[C@@H](C)c1ccccc1]

Scheme 9

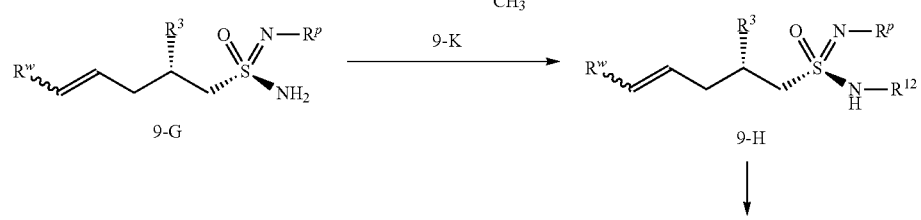

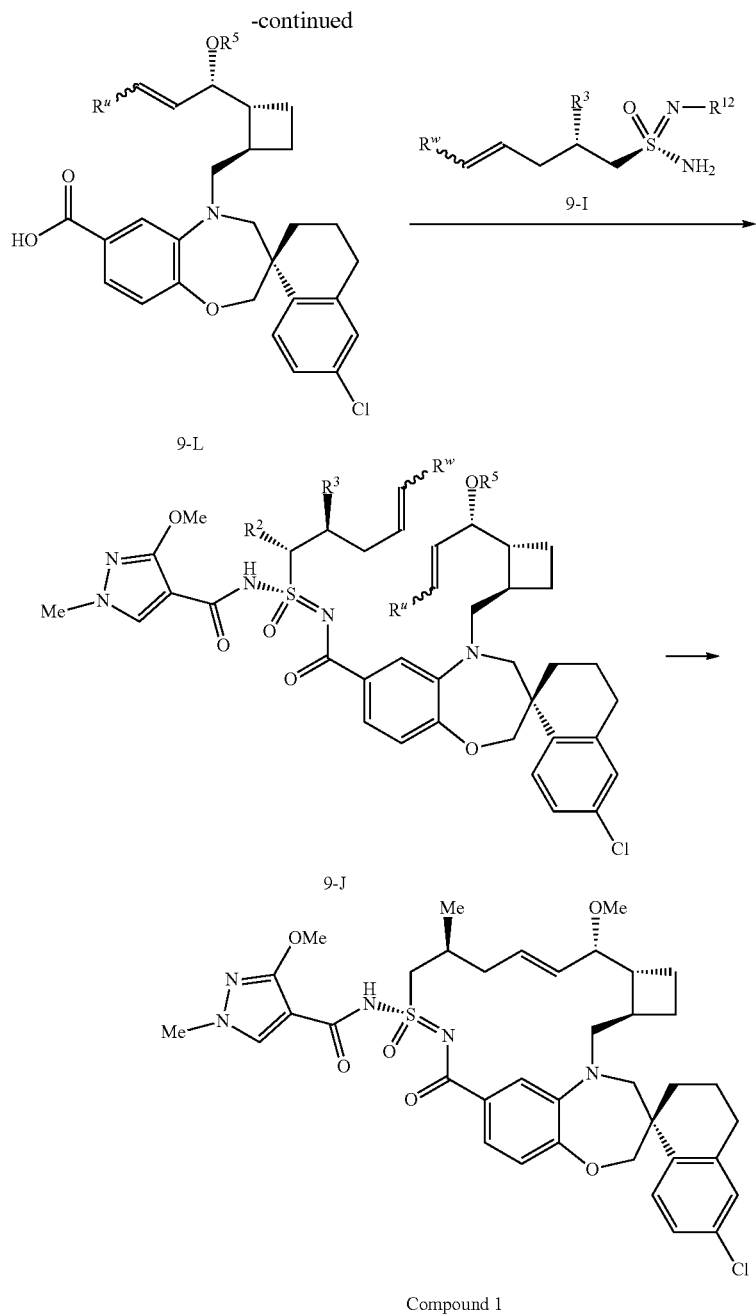

Compound 1

In one embodiment, the present disclosure provides a method to prepare a compound 9-H from a compound 9-G and a compound 9-K.

In one embodiment, the method comprises the step of reacting a compound 9-G with a compound 9-K, an acid activator, a promoter, and a base in a suitable solvent, for a time and under conditions effective to form a compound 9-H.

In one embodiment, the acid activator is selected from N-(3-dimethylaminopropyl)-N'-ethylcarbondiimide hydrochloride, carbonyldiimidazole (CDI), propylphosphonic anhydride (T3P), 1-[bis(dimethylamino)methylene]-1H-1,2,3-triazolo[4,5-b]pyridinium 3-oxide hexafluorophosphate (HATU), 4-(4,6-dimethoxy-1,3,5-triazin-2-yl)-4-methylmorpholinium chloride (DMTMM), thionyl chloride, oxalyl chloride, (chloromethylene)-dimethyliminium chloride, isobutyl chloroformate, N,N,N,N',N'-tetramethylchloroformamidinium hexafluorophosphate (TCFH), N,N'-diisopropylcarbodiimide, N,N' dicyclohexylcarbodiimide, diphenyl chlorophosphate, 2,4,6-trichlorobenzoyl chloride, and 2 chloro 4,6 dimethoxy 1,3,5 triazine (CDMT). In one embodiment, the acid activator is N-(3-dimethylaminopropyl)-N'-ethylcarbondiimide hydrochloride.

In one embodiment, the promoter is selected from 4-dimethylaminopyridine, N-methylimidazole, 1-hydroxy-7-azabenzotriazole (HOAt), 1-hydroxybenzotriazole (HOBt), N,N-dimethylacetamide, and N-methylimidazole. In one embodiment, the promoter is 4-dimethylaminopyridine.

In one embodiment, the base is selected from tertiary amines (e.g., N-methylmorpholine, triethyl amine, tripropylamine, N,N-diisopropylethylamine, tributylamine, 1,8-diazabicyclo[5.4.0]undec-7-ene, 1,4-diazabicyclo[2.2.2]octane, DABCO), aromatic amines (e.g., pyridine, 2,6-lutidine, collidine, 1-methylimidazole), inorganic bases (e.g., lithium carbonate, sodium carbonate, potassium carbonate, calcium carbonate and bicarbonate derivatives, mono, di and tri basic potassium and sodium phosphate. In one embodiment, the base is 1-methylimidazole.

In one embodiment, the solvent is selected from ethers (e.g., tetrahydrofuran, 2-methyltetrahydrofuran, methyl tert-butyl ether, cyclopentyl methyl ether), esters (e.g, ethyl acetate, isopropyl acetate), polar aprotic solvents (e.g., N,N-dimethylacetamide, N-methyl-2-pyrrolidinone, dimethyl sulfoxide), nitriles (e.g., acetonitrile), hydrocarbon solvents (e.g., toluene), halogenated solvents (e.g., dichloromethane, 1,2-dichloroethane, chloroform, chlorobenzene), and a combination thereof. In one embodiment, the solvent is acetonitrile.

In one embodiment, the temperature of the reaction is from −50 to 50° C. In one embodiment, the temperature is from 10 to 30° C.

In one embodiment, the present disclosure provides a method to prepare a compound 9-I from a compound 9-H.

In one embodiment, the method comprises the step of reacting a compound 9-H with an acid in a suitable solvent, for a time and under conditions effective to form a compound 9-I.

In one embodiment, the acid is selected from citric acid, trifluoracetic acid, methanesulfonic acid, trifluoromethanesulfonic acid, benzenesulfonic acid, p-toluenesulfonic acid, camphorsulfonic acid, pyridinium p-toluenesulfonate, sulfuric acid, hydrochloric acid, hydrobromic acid, acetic acid, formic acid, phosphoric acid, oxalic acid. In one embodiment, the acid is citric acid.

In one embodiment, the solvent is selected from ethers (e.g., tetrahydrofuran, methyl tert-butyl ether, cyclopentyl methyl ether), esters (e.g., ethyl acetate, isopropyl acetate), polar aprotic solvents (e.g., N,N-dimethylformamide, N,N-dimethylacetamide, N-methyl-2-pyrrolidinone, dimethyl sulfoxide), nitriles (e.g., acetonitrile), hydrocarbon solvents (e.g., toluene), halogenated solvents (e.g., dichloromethane, 1,2-dichloroethane, chloroform, chlorobenzene), 2-methyltetrahydrofuran, water, and a combination thereof. In one embodiment, the solvent is a combination of 2-methyltetrahydrofuran and water.

In one embodiment, the temperature of the reaction is from −50 to 70° C. In one embodiment, the temperature is from 50 to 70° C.

In one embodiment, the present disclosure provides a method to prepare a compound 9-J from a compound 9-I and a compound 9-L.

In one embodiment, the method comprises the step of reacting a compound 9-I with a compound 9-L, an acid activator, a promoter, and a base in a suitable solvent, for a time and under conditions effective to form a compound 9-J.

In one embodiment, the acid activator is selected from N-(3-dimethylaminopropyl)-N'-ethylcarbodiimide hydrochloride, carbonyldiimidazole (CDI), propylphosphonic anhydride (T3P), 1-[bis(dimethylamino)methylene]-1H-1,2,3-triazolo[4,5-b]pyridinium 3-oxide hexafluorophosphate (HATU), 4-(4,6-dimethoxy-1,3,5-triazin-2-yl)-4-methylmorpholinium chloride (DMTMM), thionyl chloride, oxalyl chloride, (chloromethylene)-dimethyliminium chloride, isobutyl chloroformate, N,N,N,N',N'-tetramethylchloroformamidinium hexafluorophosphate (TCFH), N,N'-diisopropylcarbodiimide, N,N' dicyclohexylcarbodiimide, diphenyl chlorophosphate, 2,4,6-trichlorobenzoyl chloride, 2 chloro 4,6 dimethoxy 1,3,5 triazine (CDMT). In one embodiment, the acid activator is N-(3-dimethylaminopropyl)-N'-ethylcarbondiimide hydrochloride.

In one embodiment, the promoter is selected from 4-dimethylaminopyridine, N-methylimidazole, 1-hydroxy-7-azabenzotriazole (HOAt), 1-hydroxybenzotriazole (HOBt), N,N-dimethylacetamide, N-methylimidazole. In one embodiment, the promoter is 4-dimethylaminopyridine.

In one embodiment, the base is selected from tertiary amines (e.g., N-methylmorpholine, triethyl amine, tripropylamine, N,N-diisopropylethylamine, tributylamine, 1,8-diazabicyclo[5.4.0]undec-7-ene, 1,4-diazabicyclo[2.2.2]octane, DABCO), aromatic amines (e.g., pyridine, 2,6-lutidine, collidine, 1-methylimidazole), inorganic bases (e.g., lithium carbonate, sodium carbonate, potassium carbonate, calcium carbonate and bicarbonate derivatives, mono, di and tri basic potassium and sodium phosphate). In one embodiment, the base is 1-methylimidazole.

In one embodiment, the solvent is selected from ethers (e.g., tetrahydrofuran, 2-methyltetrahydrofuran, methyl tert-butyl ether, cyclopentyl methyl ether), esters (e.g, ethyl acetate, isopropyl acetate), polar aprotic solvents (e.g., N,N-dimethylacetamide, N-methyl-2-pyrrolidinone, dimethyl sulfoxide), other nitriles (e.g., acetonitrile), hydrocarbon solvents (e.g., toluene), halogenated solvents (e.g., dichloromethane, 1,2-dichloroethane, chloroform, chlorobenzene), and a combination thereof. In one embodiment, the solvent is acetonitrile.

In one embodiment, the temperature of the reaction is from −50 to 50° C. In one embodiment, the temperature is from 10 to 30° C.

In one embodiment, the method comprises the step of converting a compound 9-G to a compound 9-H.

In one embodiment, the method comprises the step of converting a compound 9-H to a 9-I.

In one embodiment, the method comprises the step of converting a compound 9-I to a 9-J.

In one embodiment, the present disclosure provides a method of making a compound a compound selected from 9-H, 9-I, and 9-J.

In one embodiment, the present disclosure provides a method of making a compound 1 from a compound selected from 9-G, 9-H, 9-I, 9-L, and 9-J, as shown in Scheme 9.

J. Method of Preparing Formula 1-I from 10-A

In one embodiment, the present disclosure provides a method of making a compound selected from 10-B, 10-C, 10-D, 10-E, 10-F, 10-G, and 1-I, as shown in Scheme 10, wherein $R^5$ is methyl, $R^8$ is $C_{1-6}$ alkyl wherein alkyl is optionally substituted with $C_{6-10}$aryl, and $R^x$ is H or $C_{1-6}$alkyl, In one embodiment, $R^8$ is isopropyl, n-butyl, or benzyl. In one embodiment, $R^8$ is methyl. In one embodiment, $R^8$ is ethyl. In one embodiment, $R^x$ is H.

In one embodiment, PG is selected from silyl (e.g., tertbutyldiphenylsilyl, tert-butyldimethylsilyl (TBS)), alkylcarbonyl (e.g., COMe), arylcarbonyl (e.g., COPh), alkoxycarbonyl (e.g., $CO_2$tBu), aryloxycarbonyl ($CO_2$Ph), alkyl (e.g., trityl), alkoxymethyl (e.g., MOM). In one embodiment, PG is selected from a tri-$C_{1-6}$alkyl silyl group, a di-$C_{1-6}$alkyl-phenyl silyl group, a $C_{1-6}$alkyl-di-phenyl silyl group, and a tri-phenyl silyl group. In one embodiment, PG is tert-butyldimethylsilyl (TBS).

Scheme 10

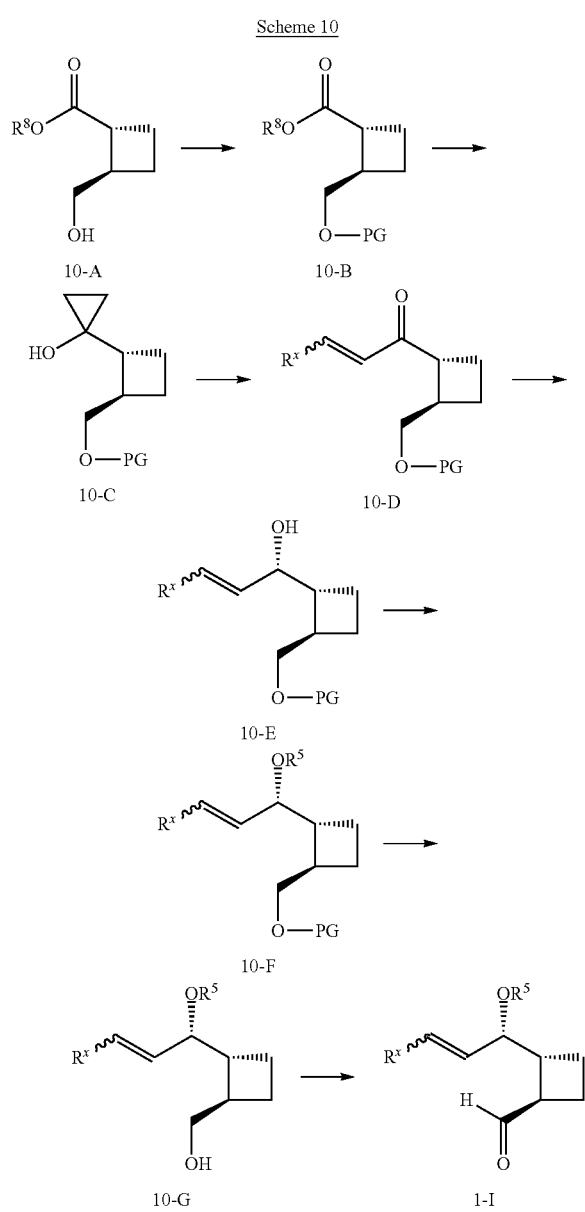

In one embodiment, the present disclosure provides a method to prepare a compound 10-B from a compound 10-A.

In one embodiment, the method comprises the step of treating a compound 10-A with a protecting reagent, and a base in a suitable solvent, for a time and under conditions effective to form a compound 10-B.

In one embodiment, the protecting reagent is selected from silyl chlorides (e.g., chlorotrimethylsilane, chlorotriethylsilane, chlorotripropylsilane, triisopropylsilyl chloride, tert-butyldiphenylsilyl chloride, chlorodimethylphenylsilane, chlorotriphenylsilane, tert-butyl(chloro)dimethylsilane), silyl trifluoromethanesulfonates (e.g., trimethylsilyl trifluoromethanesulfonate, triethylsilyl trifluoromethanesulfonate, triisopropylsilyl trifluoromethanesulfonate, tert-butyldimethylsilyl trifluoromethanesulfonate, dimethylphenylsilyl trifluoromethanesulfonate, triphenylsilyl trifluoromethanesulfonate), silyl bromides (e.g., bromotrimethylsilane, bromotriethylsilane, bromotripropylsilane, tri-isopropylsilyl bromide, tert-butyldimethylsilyl bromide, bromodimethylphenylsilane, bromotriphenylsilane), N,O-bis(trimethylsilyl)acetamide, N,O-bis(trimethylsilyl)trifluoroacetamide, N-methyl-N-(trimethylsilyl)trifluoroacetamide, benzyl halides (e.g., 3,5-dimethoxybenzyl chloride, 3,5-dimethoxybenzyl bromide), dibenzyl carbonate, acid chlorides (e.g., pivaloyl chloride, 1-adamantanecarbonyl chloride), anhydrides (e.g., di-tert-butyl carbonate), chloroformates (e.g., methyl chloroformate, ethyl chloroformate, benzyl chloroformate, phenyl chloroformate), alkyl chlorides (e.g., trityl chloride), alkoxymethyl chlorides (e.g., methoxymethyl chloride). In one embodiment, the protecting reagent is tert-butyl(chloro)dimethylsilane.

In one embodiment, the base is selected from tertiary amines (e.g., N-methylmorpholine, tripropylamine, N,N-diisopropylethylamine, tributylamine, 1,8-diazabicyclo[5.4.0]undec-7-ene, 1,4-diazabicyclo[2.2.2]octane), aromatic amines (e.g., pyridine, 2,6-lutidine, collidine, 1-methylimidazole, imidazole), inorganic bases (e.g., lithium carbonate, sodium carbonate, potassium carbonate, calcium carbonate, potassium phosphate, sodium phosphate). In one embodiment, the base is imidazole.

In one embodiment, the suitable solvent is selected ethers (e.g., tetrahydrofuran, 2-methyltetrahydrofuran, methyl tert-butyl ether, cyclopentyl methyl ether), hydrocarbon solvents (e.g., toluene, n-heptane), halogenated solvents (e.g., 1,2-dichloroethane, chloroform, dichloromethane, chlorobenzene), polar aprotic solvents (e.g., N,N-dimethylformamide, N,N-dimethylacetamide, N-methyl-2-pyrrolidinone, dimethyl sulfoxide), nitriles (e.g., acetonitrile), and a combination thereof. In one embodiment, the solvent is dichloromethane.

In one embodiment, the temperature of the reaction is from −30 to 60° C. In one embodiment, the temperature of the reaction is from 10 to 30° C.

In one embodiment, the present disclosure provides a method to prepare a compound 10-C from a compound 10-B.

In one embodiment, the method comprises the step of treating a compound 10-B with a Grignard reagent, and a promoter in a suitable solvent, for a time and under conditions effective to form a compound 10-C.

In one embodiment, the Grignard reagent is selected from ethylmagnesium bromide in other ethereal solvents (e.g., methyl tert-butyl ether, diethyl ether, dibutyl ether, dioxane), ethylmagnesium chloride in ethereal solvents (e.g., tetrahydrofuran, methyl tert-butyl ether, diethyl ether, dibutyl ether, dioxane), n-propylmagnesium bromide, 2-phenylethylmagnesium bromide. In one embodiment, the Grignard reagent is ethylmagnesium bromide.

In one embodiment, the promoter is selected from titanium(IV) alkoxides (e.g., titanium(IV) methoxide, titanium (IV) ethoxide, titanium(IV) propoxide, titanium(IV) isopropoxide, titanium(IV) butoxide). In one embodiment, the promoter is titanium(IV) isopropoxide.

In one embodiment, the suitable solvent is selected ethers (e.g., 2-methyltetrahydrofuran, methyl tert-butyl ether, cyclopentyl methyl ether), hydrocarbons (e.g., toluene, n-heptane), polar aprotic solvents (e.g., N,N-dimethylformamide, N,N-dimethylacetamide, N-methyl-2-pyrrolidinone, dimethyl sulfoxide), nitriles (e.g., acetonitrile), and a combination thereof. In one embodiment, the solvent is tetrahydrofuran.

In one embodiment, the temperature of the reaction is from −20 to 30° C. In one embodiment, the temperature of the reaction is from −5 to 15° C.

In one embodiment, the present disclosure provides a method to prepare a compound 10-D from a compound 10-C.

In one embodiment, the method comprises the step of treating a compound 10-C with a halogenating reagent, and a base in a suitable solvent, for a time and under conditions effective to form a compound 10-D.

In one embodiment, the halogenating reagent is selected from N-bromophthalimide, bromine, 1,3-dibromo-5,5-dimethylhydantoin, N-bromosaccharin, hypobromous acid, N-chlorophthalimide, N-chlorosuccinimide, N-chlorosaccharin, 1,3-dichloro-5,5-dimethylhydantoin, N-iodosucciminide, N-iodophthalimide, N-bromosuccinimide, iodine. In one embodiment, the halogenating reagent is N-bromosuccinimide.

In one embodiment, the base is selected from tertiary amines (e.g., N-methylmorpholine, tripropylamine, N,N-diisopropylethylamine, tributylamine, triethylamine, 1,8-diazabicyclo[5.4.0]undec-7-ene, 1,4-diazabicyclo[2.2.2]octane, DABCO), aromatic amines (e.g., pyridine, 2,6-lutidine, collidine, 1-methylimidazole). In one embodiment, the base is triethylamine.

In one embodiment, the suitable solvent is selected ethers (e.g., tetrahydrofuran, 2-methyltetrahydrofuran, methyl tert-butyl ether, cyclopentyl methyl ether), hydrocarbon solvents (e.g., toluene, n-heptane), esters (e.g., ethyl acetate, isopropyl acetate), halogenated solvents (e.g., 1,2-dichloroethane, dichloromethane, chloroform, chlorobenzene), and a combination thereof. In one embodiment, the solvent is dichloromethane.

In one embodiment, the temperature of the reaction is from −20 to 30° C. In one embodiment, the temperature of the reaction is from −5 to 20° C.

In one embodiment, the present disclosure provides a method to prepare a compound 10-E from a compound 10-D.

In one embodiment, the method comprises the step of treating a compound 10-D with an enzyme, a co-factor, a recycle system, and a buffer at a suitable pH in a suitable solvent, for a time and under conditions effective to form a compound 10-E.

In one embodiment, the enzyme is selected ketoreductases. In one embodiment, the halogenating reagent is CRED-A151.

In one embodiment, the co-factor is NADP. In one embodiment, the co-factor is NAD.

In one embodiment, the recycle system is selected from isopropanol, phosphite dehydrogenase (PDH) and phosphite, formate dehydrogenase (FDH) and ammonium formate, glucose dehydrogenase (GDH) and glucose monohydrate. In one embodiment, the recycle system is glucose dehydrogenase (GDH) and glucose monohydrate.

In one embodiment, the buffer is aqueous buffers (e.g., sodium phosphate). In one embodiment, the buffer is 0.1 M aqueous citrate buffer.

In one embodiment, the pH value is from 4 to 9. In one embodiment, the pH value is 6.2.

In one embodiment, the suitable solvent is selected ethers (e.g., tetrahydrofuran, 2-methyltetrahydrofuran, methyl tert-butyl ether, cyclopentyl methyl ether), polar aprotic solvents (e.g. N,N-dimethylacetamide, N-methyl-2-pyrrolidinone, DMSO), and a combination thereof. In one embodiment, the solvent is DMSO.

In one embodiment, the temperature of the reaction is from 20 to 40° C. In one embodiment, the temperature of the reaction is from 25 to 35° C.

In one embodiment, the present disclosure provides a method to prepare a compound 10-F from a compound 10-E.

In one embodiment, the method comprises the step of treating a compound 10-E with a base and a methylating reagent in a suitable solvent, for a time and under conditions effective to form a compound 10-F.

In one embodiment, the methylating reagent is selected from dimethyl sulfate, iodomethane, methyl triflate, methyl tosylate. In one embodiment, the methylating reagent is iodomethane.

In one embodiment, the base is selected from sodium hydride, potassium tert-butoxide, lithium tert-butoxide, sodium hydroxide, potassium hydroxide, lithium hydroxide, potassium tert-pentoxide, sodium tert-pentoxide, lithium tert-pentoxide, sodium hexamethyldisilazide, lithium hexamethyldisilazide, potassium hexamethyldisilazide, lithium diisoproylamide, sodium diisoproylamide, potassium diisoproylamide, sodium tert-butoxide. In one embodiment, the base is sodium tert-butoxide.

In one embodiment, the suitable solvent is selected ethers (e.g., 2-methyltetrahydrofuran, methyl tert-butyl ether, cyclopentyl methyl ether, tetrahydrofuran), hydrocarbon solvents (e.g., toluene, n-heptane), halogenated solvents (e.g., dichloromethane, 1,2-dichloroethane, chloroform, chlorobenzene), alcohols (e.g., tert-butanol, tert-amyl alcohol), polar aprotic solvents (e.g., N,N-dimethylacetamide, N,N-dimethylformamide, N-methyl-2-pyrrolidinone, dimethyl sulfoxide), water, and a combination thereof. In one embodiment, the solvent is tetrahydrofuran.

In one embodiment, the temperature of the reaction is from −78 to 50° C. In one embodiment, the temperature of the reaction is from −10 to 10° C.

In one embodiment, the present disclosure provides a method to prepare a compound 10-G from a compound 10-F.

In one embodiment, the method comprises the step of treating a compound 10-F with a deprotection reagent in a suitable solvent, for a time and under conditions effective to form a compound 10-G.

In one embodiment, the deprotection reagent is selected from sodium hydroxide, potassium hydroxide, lithium hydroxide, sulfuric acid, trifluoroacetic acid, phosphoric acid, hydrofluoric acid, hydrochloric acid (conc.), hydrogen fluoride pyridine, hydrogen fluoride triethylamine, potassium fluoride, sodium fluoride, lithium fluoride, cesium fluoride, tetramethylammonium fluoride, tetrabutylammonium fluoride. In one embodiment, the deprotection reagent is hydrochloric acid (conc.).

In one embodiment, the suitable solvent is selected ethers (e.g., 2-methyltetrahydrofuran, methyl tert-butyl ether, cyclopentyl methyl ether), hydrocarbon solvents (e.g, toluene, n-heptane), halogenated solvents (e.g., dichloromethane, 1,2-dichloroethane, chloroform, chlorobenzene), alcohols (e.g., ethanol, n-propanol, isopropanol, methanol), polar aprotic solvents (e.g., N,N-dimethylacetamide, N,N-dimethylformamide, N-methyl-2-pyrrolidinone, dimethyl sulfoxide), water, and a combination thereof. In one embodiment, the solvent is methanol.

In one embodiment, the temperature of the reaction is from −15 to 50° C. In one embodiment, the temperature of the reaction is from 10 to 30° C.

In one embodiment, the present disclosure provides a method of making a compound 1-I from a compound selected from 10-A, 10-B, 10-C, 10-C, 10-D, 10-E, 10-F, and 10-G, as shown in Scheme 10.

In one embodiment, the present disclosure provides a method of making a compound 1 from a compound selected from 1-I, 10-A, 10-B, 10-C, 10-C, 10-D, 10-E, 10-F, and 10-G, as shown in Scheme 1 and Scheme 10.

K. Method of Preparing Formula 5-E from 5-C

In one embodiment, the present disclosure provides a method of making a compound of 5-E from 5-C, as shown in Scheme 11. wherein $R^m$ is $C_{1-6}$ alkyl, and two $R^n$ moieties join together to form a $C_{2-4}$alkyl bridge, wherein the bridge is optionally substituted by one to four groups independently selected from $C_{1-3}$alkyl and phenyl. In one embodiment, $R^m$ is methyl. In one embodiment, two $R^n$ moieties join together to form a bridge selected from —CH$_2$CH$_2$—, —CH(CH$_3$)CH(CH$_3$)—, —CH$_2$CH(CH$_3$)—, —CH$_2$CH(C$_6$H$_5$)—, —C(CH$_3$)$_2$C(CH$_3$)$_2$—, —CH$_2$CH$_2$CH$_2$—, —CH$_2$CBr$_2$CH$_2$—, —CH$_2$(C═CH)CH$_2$—, —CH$_2$CH(C$_6$H$_5$)CH$_2$—, —CH(CH$_3$)CH$_2$CH(CH$_3$)—, —CH$_2$CH(CH$_3$)CH$_2$—, —CH$_2$C(CH$_3$)$_2$CH$_2$—, —CH$_2$C(CH$_2$CH$_3$)$_2$CH$_2$—, —CH$_2$CH$_2$CH$_2$CH$_2$—, —CH$_2$CH$_2$CH$_2$CH$_2$CH$_2$—, —CH(C$_6$H$_5$)CH(C$_6$H$_5$), —CH$_2$CH(C$_6$H$_5$)CH$_2$—, and -(o-C$_6$H$_4$)—. In one embodiment, two $R^n$ moieties join together to form —C(CH$_3$)$_2$C(CH$_3$)$_2$—.

Scheme 11

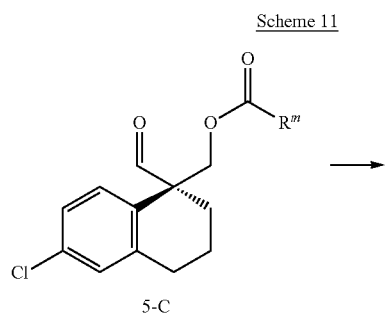

5-C

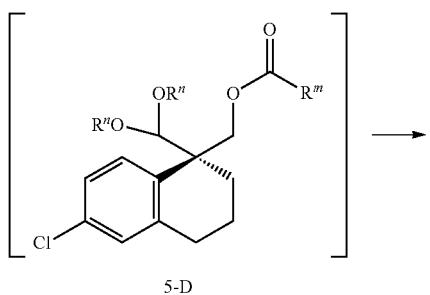

5-D

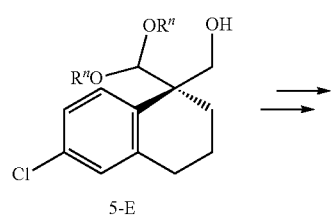

5-E

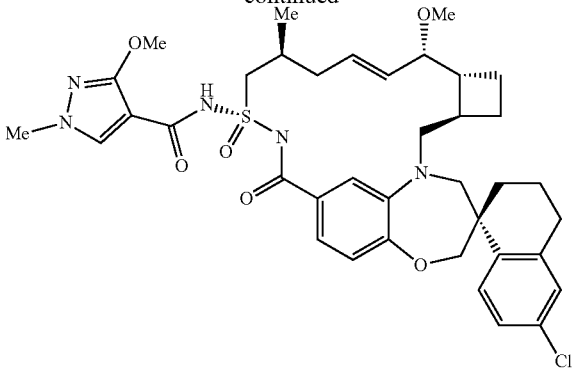

Compound 1

In one embodiment, the present disclosure provides a method to prepare a compound 5-D from a compound 5-C.

In one embodiment, the method comprises the step of treating a compound 5-C with an acid in a suitable solvent, for a time and under conditions effective to form a compound 5-D.

In one embodiment, the acid is selected from methanesulfonic acid, trifluoroacetic acid, trifluoromethanesulfonic acid, benzenesulfonic acid, camphorsulfonic acid, pyridinium p-toluenesulfonate, sulfuric acid, hydrochloric acid, hydrobromic acid, acetic acid, formic acid, phosphoric acid, and oxalic acid. In one embodiment, the acid is p-toluenesulfonic acid.

In one embodiment, the suitable solvent is selected from halogenated solvents (e.g., dichloromethane, 1,2-dichloroethane, chloroform, chlorobenzene), ethers (e.g., tetrahydrofuran, 2-methyltetrahydrofuran, methyl tert-butyl ether, cyclopentyl methyl ether), aromatic solvents (e.g, benzene, trifluorotoluene, xylenes, toluene), polar aprotic solvents (e.g., N,N-dimethylformamide, N,N-dimethylacetamide, N-methyl-2-pyrrolidinone, dimethyl sulfoxide), hydrocarbon solvents (e.g., cyclohexane, methyl cyclohexane, hexanes, heptanes), and a combination thereof. In one embodiment, the solvent is toluene.

In one embodiment, the temperature of the reaction is from 0 to 60° C. In one embodiment, the temperature of the reaction is about 45° C.

In one embodiment, the present disclosure provides a method to prepare a compound 5-E from a compound 5-D.

In one embodiment, the method comprises the step of treating a compound 5-D with a base in a suitable solvent, for a time and under conditions effective to form a compound 5-E.

In one embodiment, the base is selected from hydroxide bases (e.g., lithium hydroxide, sodium hydroxide, potassium hydroxide, ammonium hydroxide), carbonate bases (e.g., sodium carbonate, potassium carbonate, cesium carbonate), phosphate bases, potassium tert-butoxide, potassium methoxide, and sodium methoxide. In one embodiment, the base is sodium hydroxide.

In one embodiment, the suitable solvent is selected from 2-methyltetrahydrofuran, halogenated solvents (e.g., dichloromethane, 1,2-dichloroethane, chloroform, chlorobenzene), ethers (e.g., tetrahydrofuran, methyl tert-butyl ether, cyclopentyl methyl ether), alcohols (e.g., ethanol, methanol, n-propanol, isopropanol), aromatic solvents (e.g., benzene, trifluorotoluene, xylenes), polar aprotic solvents (e.g., N,N-dimethylformamide, N,N-dimethylacetamide, N-methyl-2-pyrrolidinone, dimethyl sulfoxide), hydrocarbon solvents (e.g., cyclohexane, methyl cyclohexane, hexanes, heptanes), and a combination thereof. In one embodiment, the solvent is the combination of 2-methyltetrahydrofuran and ethanol.

In one embodiment, the temperature of the reaction is from 0 to 60° C. In one embodiment, the temperature of the reaction is about 20° C.

In one embodiment, the present disclosure provides a method of making a compound 1 from a compound selected from 5-C, 5-D, and 5-E, as shown in Scheme 1 and Scheme 11.

IV. Compounds

In one embodiment, the present disclosure provides a compound selected from:

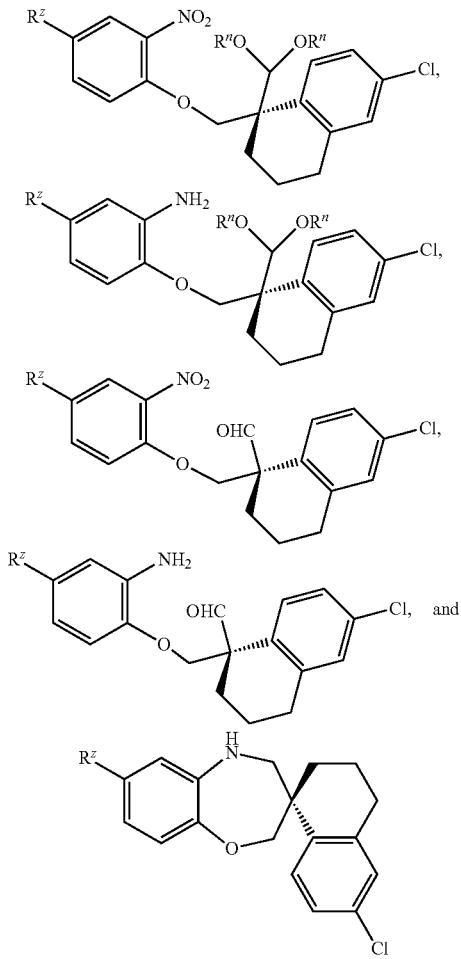

wherein
each $R''$ is independently $C_{1-6}$alkyl, or the two $R''$ moieties join together to form a $C_{2-4}$alkyl bridge, wherein the bridge is optionally substituted by one to four groups independently selected from $C_{1-3}$alkyl and phenyl; and $R^z$ is halogen or CN.

In one embodiment, $R''$ is methyl.

In one embodiment, two $R''$ moieties join together to form a bridge selected from —CH$_2$CH$_2$—, —CH(CH$_3$)CH(CH$_3$)—, —CH$_2$CH(CH$_3$)—, —CH$_2$CH(C$_6$H$_5$)—, —C(CH$_3$)$_2$C(CH$_3$)$_2$—, —CH$_2$CH$_2$CH$_2$—, —CH$_2$CBr$_2$CH$_2$—, —CH$_2$(C=CH)CH$_2$—, —CH$_2$CH(C$_6$H$_5$)CH$_2$—, —CH(CH$_3$)CH$_2$CH(CH$_3$)—, —CH$_2$CH(CH$_3$)CH$_2$—, —CH$_2$C(CH$_3$)$_2$CH$_2$—, —CH$_2$C(CH$_2$CH$_3$)$_2$CH$_2$—, —CH$_2$CH$_2$CH$_2$CH$_2$—, —CH$_2$CH$_2$CH$_2$CH$_2$CH$_2$—, —CH(C$_6$H$_5$)CH(C$_6$H$_5$), —CH$_2$CH(C$_6$H$_5$)CH$_2$—, and -(o-C$_6$H$_4$)—.

In one embodiment, two $R''$ moieties join together to form —C(CH$_3$)$_2$C(CH$_3$)$_2$—.

In one embodiment, the present disclosure provides a compound selected from:

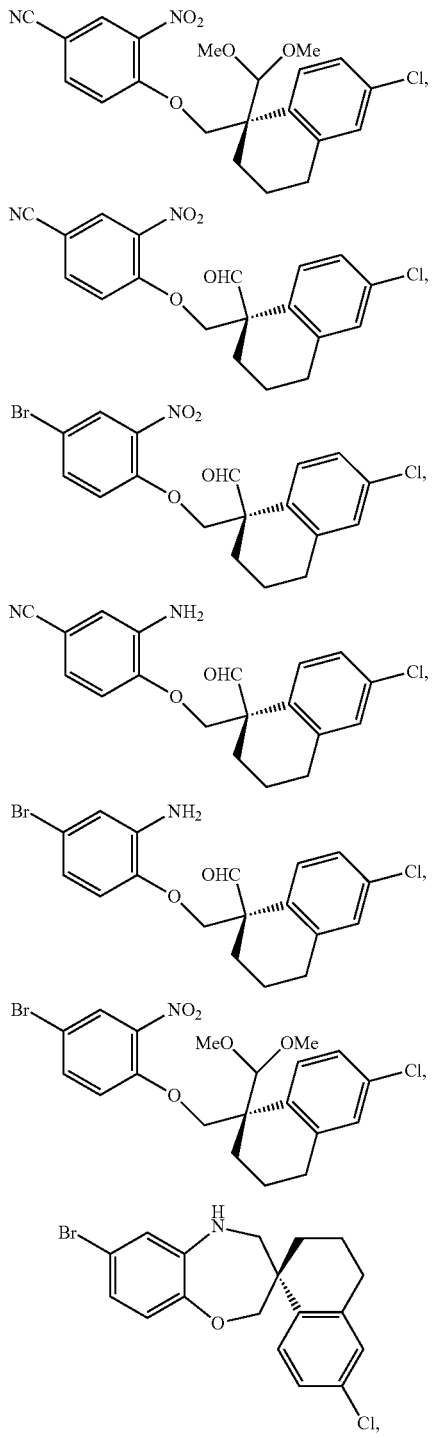

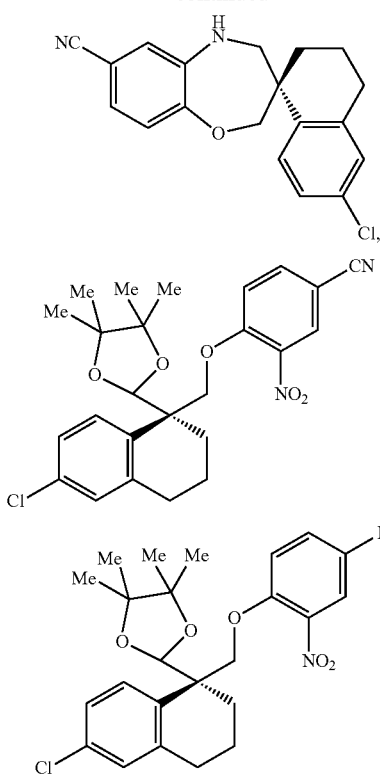
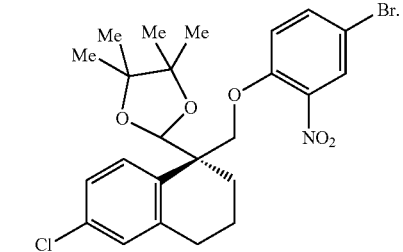
In one embodiment, the present disclosure provides a compound selected from:
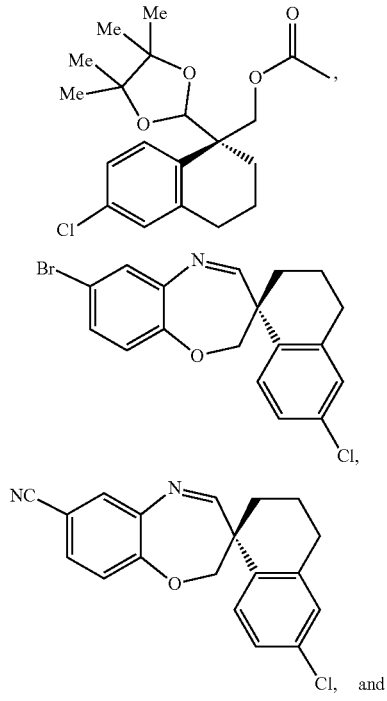
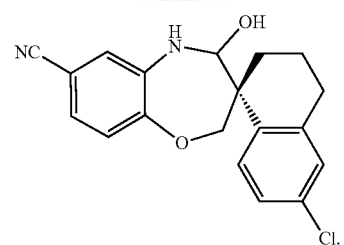
In one embodiment, the present disclosure provides a compound selected from:
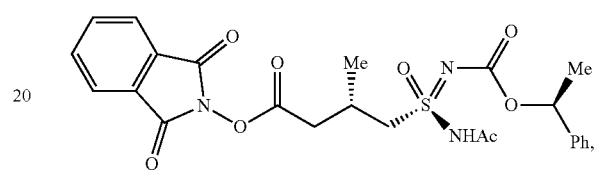
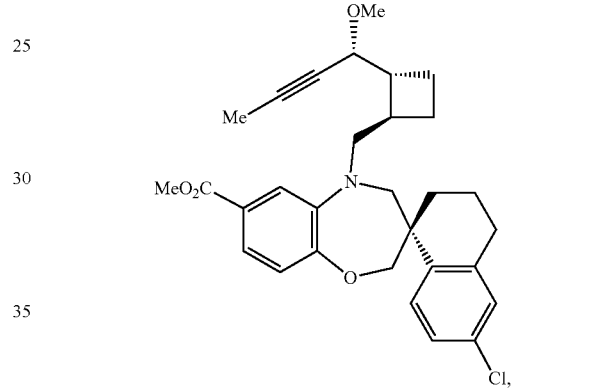
In one embodiment, the present disclosure provides a compound selected from:
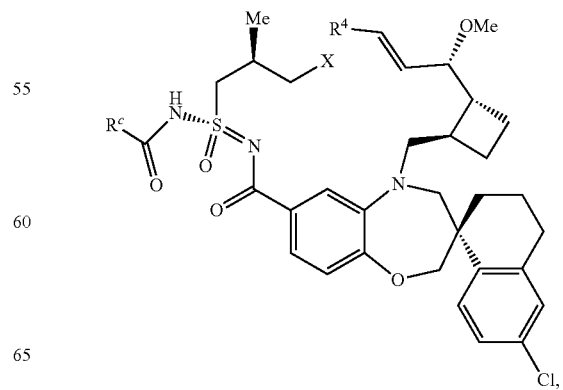

91

-continued

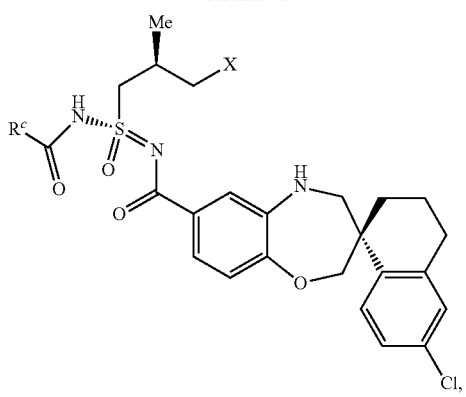

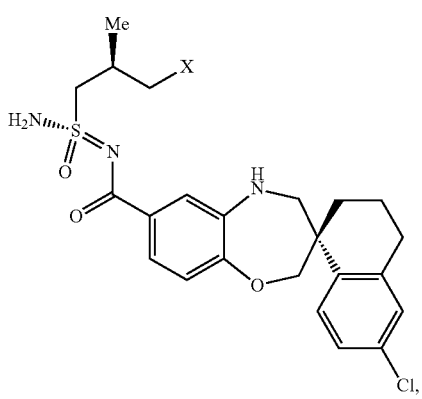

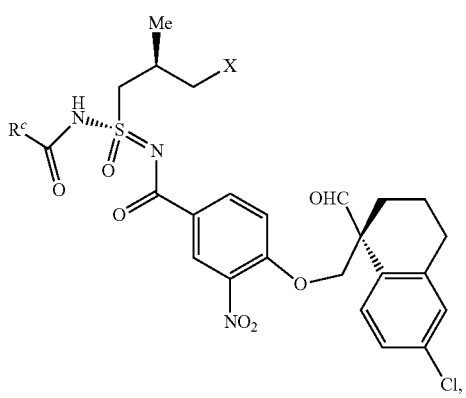

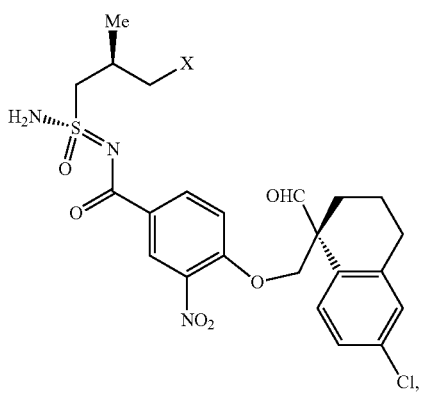

92

-continued

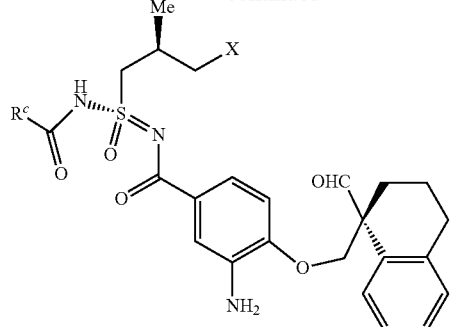

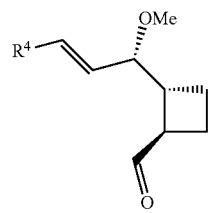

wherein
X is halogen,

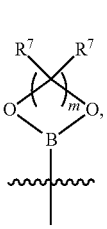 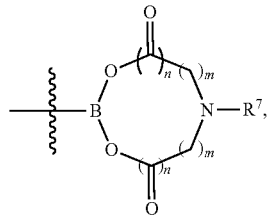

$C(O)_2R^1$, $-OS(O)_2R^2$, or $-OP(O)(R^2)_2$, wherein $R^1$ is H or $C_{1-6}$alkyl, each $R^2$ is $C_{1-6}$alkyl or $C_{6-10}$aryl, each $R^7$ is independently H or $C_{1-3}$alkyl, wherein each alkyl or aryl is optionally substituted with one to four halogen or $C_{1-3}$alky, m is 1, 2, or 3, and n is 0 or 1; and $R^4$ is halogen, and $R^c$ is $C_{1-6}$alkyl.

In one embodiment, X is selected from halogen, COOH,

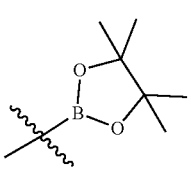 and 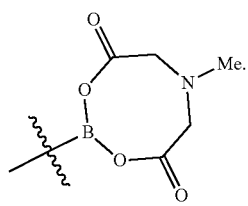

In one embodiment, the present disclosure provides a compound selected from:

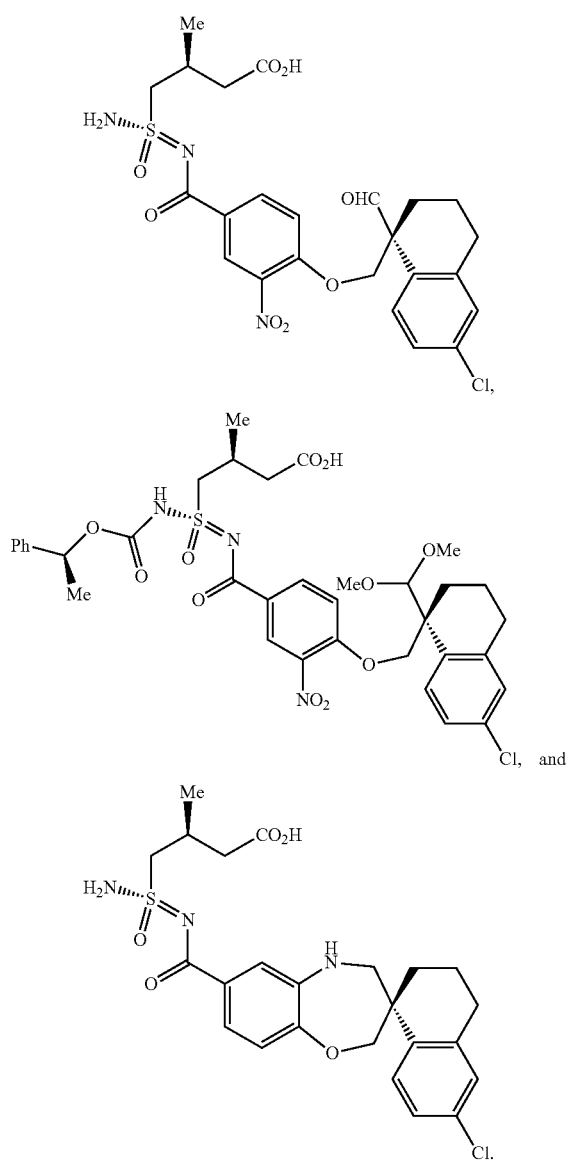

In one embodiment, the present disclosure provides a compound selected from:

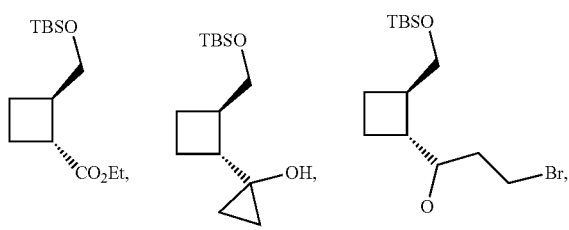

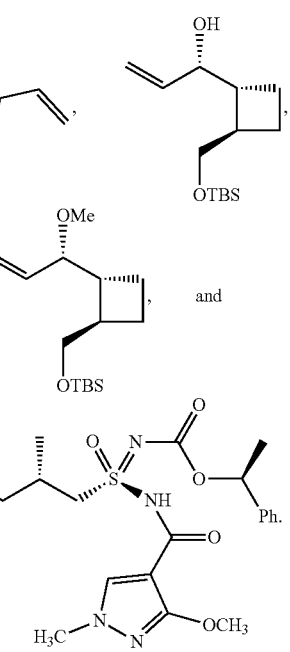

V. Examples

Oxidative Cleavage of EX-52 to EX-109:

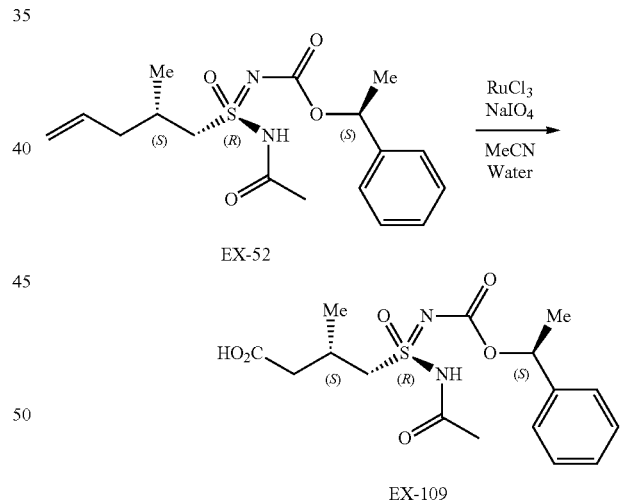

A reactor was charged with EX-52 (1.0 equiv., scaling factor), ruthenium(III) chloride hydrate (0.1 equiv.), sodium periodate (6.0 equiv.), and 1:1 v/v acetonitrile:water (20 volumes). The reaction mixture was stirred at about 20° C. for about 16 hours. The reaction mixture was diluted with ethyl acetate (50 volumes) and 5 wt % aqueous acetic acid (50 volumes). The aqueous layer was extracted with two portions of ethyl acetate (50 volumes) and the combined organic layers were washed with 10 wt % aqueous sodium thiosulfate (15 volumes) and water (15 volumes). The combined organic layers were dried over sodium sulfate, filtered, and concentrated to afford EX-109. $^1$H NMR (400 MHz, CDCl₃) δ 7.40-7.26 (m, 5H), 5.78 (q, J=6.6 Hz, 1H), 3.83 (dd, J=14.6, 6.3 Hz, 1H), 3.68 (dd, J=14.5, 6.0 Hz, 1H), 2.72-2.54 (m, 2H), 2.42 (dd, J=16.2, 6.7 Hz, 1H), 2.12 (s, 3H), 1.59 (d, J=6.6 Hz, 3H), 1.20 (d, J=6.7 Hz, 3H).

Esterification of EX-109 to EX-110:

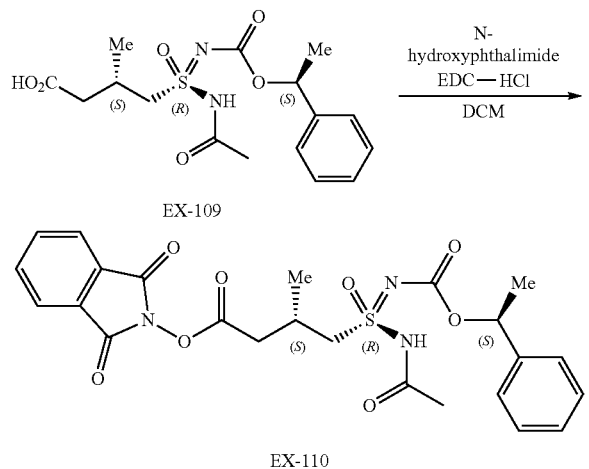

A reactor was charged with EX-109 (1.0 equiv., scaling factor), N-hydroxyphthalimide (2.0 equiv.), EDC.HCl (2.0 equiv.), and dichloromethane (10 volumes). The reaction mixture was stirred at about 20° C. for about 2 hours. The reaction mixture was diluted with ethyl acetate (50 volumes) and the organic layer was washed with 5 wt % aqueous acetic acid (20 volumes), 3 M aqueous potassium carbonate (20 volumes), and water (20 volumes). The organic layer was dried over sodium sulfate, filtered, and concentrated. The crude product was purified by chromatography using ethyl acetate, heptane, and acetic acid to afford EX-110. ¹H NMR (400 MHz, CDCl₃) δ 7.88 (dt, J=7.3, 3.6 Hz, 2H), 7.80 (dq, J=6.7, 4.0, 3.6 Hz, 2H), 7.39-7.25 (m, 4H), 5.76 (q, J=6.6 Hz, 1H), 3.74 (qd, J=14.6, 6.2 Hz, 2H), 2.94 (dd, J=15.2, 4.6 Hz, 1H), 2.76 (ddt, J=22.5, 15.3, 6.9 Hz, 2H), 2.10 (d, J=5.8 Hz, 3H), 1.57 (d, J=6.6 Hz, 3H), 1.28 (d, J=6.6 Hz, 3H).

Borylation of EX-110 to EX-111:

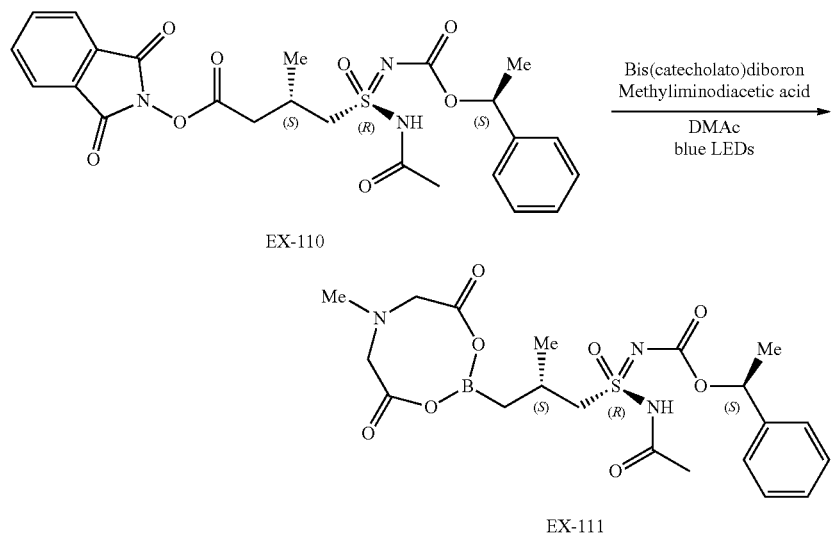

A reactor was charged with EX-110 (1.0 equiv., scaling factor), bis(catecholato)diboron (1.3 equiv.), and dimethylacetamide (20 volumes). The reaction mixture was irradiated with a 34 W blue LED lamp at about 20° C. for about 3 hours. Methyliminodiacetic acid (5.0 equiv.) was added and the reaction mixture was heated to about 50-60° C. for about 1 hour. The reaction mixture was diluted with ethyl acetate (100 volumes) and water (50 volumes). The aqueous layer was extracted with ethyl acetate (75 volumes) and the combined organic layers were washed with saturated aqueous sodium chloride (50 volumes). The organic layer was dried over sodium sulfate, filtered, and concentrated. The crude product was purified by chromatography using dichloromethane and methanol to afford EX-111. ¹H NMR (400 MHz, CDCl₃) δ 7.34 (dd, J=8.3, 5.3 Hz, 4H), 7.28 (s, 1H), 5.72 (q, J=6.6 Hz, 1H), 3.84 (dd, J=16.8, 3.1 Hz, 2H), 3.73-3.54 (m, 4H), 2.65 (s, 3H), 2.46-2.36 (m, 1H), 2.08 (s, 3H), 1.55 (d, J=6.6 Hz, 3H), 1.16 (d, J=6.9 Hz, 3H), 0.91 (dd, J=14.3, 4.9 Hz, 1H), 0.62 (dd, J=14.4, 8.0 Hz, 1H).

Oxidative Cleavage of EX-84 and Deprotection to EX-112:

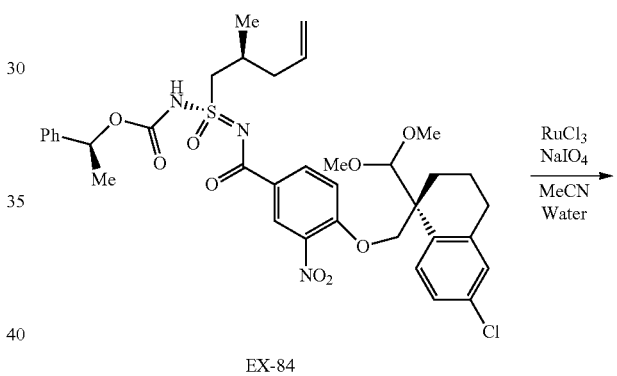

-continued

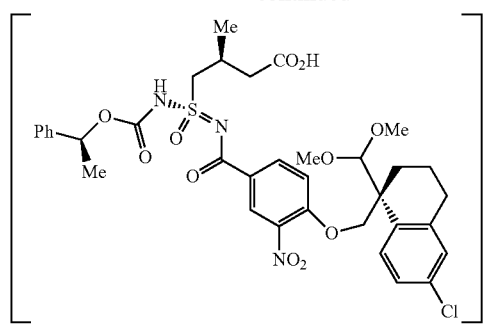

Reductive Cyclization of EX-112 to EX-113:

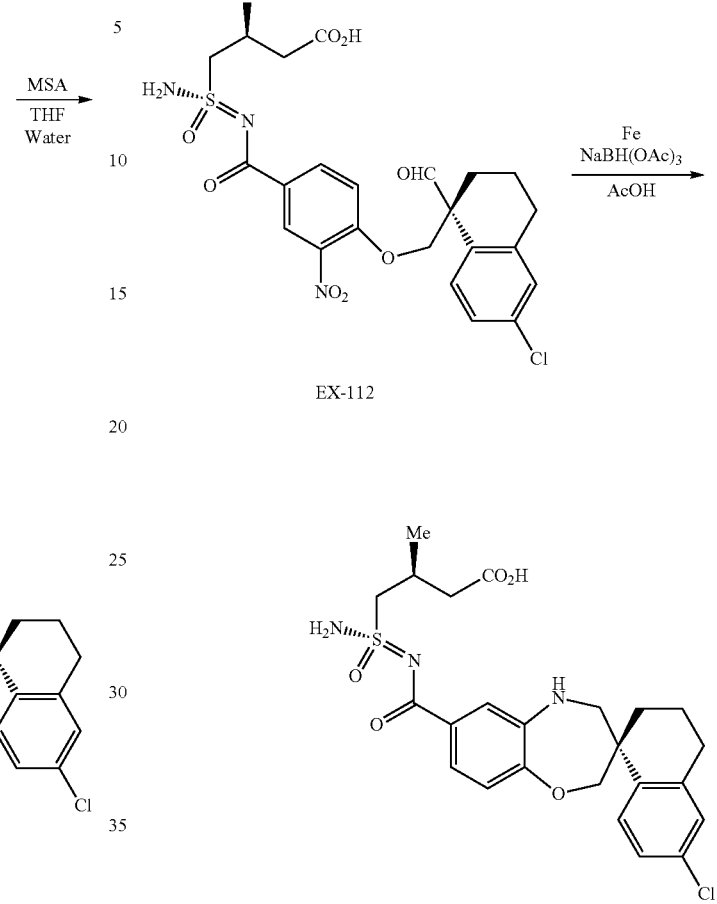

A reactor was charged with EX-84 (1.0 equiv., scaling factor), ruthenium(III) chloride hydrate (0.3 equiv.), sodium periodate (6.0 equiv.), and 1:1 v/v acetonitrile:water (20 volumes). The reaction mixture was stirred at about 0° C. for about 2 hours. The reaction mixture was diluted with ethyl acetate (80 volumes) and 5 wt % aqueous acetic acid (40 volumes). The mixture was filtered through Celite and the filtrate extracted with two portions of ethyl acetate (40 volumes). The combined organic layers were dried over sodium sulfate, filtered, and concentrated. The crude product was charged with 15 v/v % water in tetrahydrofuran (10 volumes). The solution was charged with methanesulfonic acid (2 volumes) and agitated at about 65° C. for about 18 hours. The reaction mixture was cooled to about 20° C. and diluted with ethyl acetate (20 volumes) and water (20 volumes). The aqueous layer was extracted with ethyl acetate (20 mL) and the combined organic layer was dried over sodium sulfate, filtered, and concentrated to dryness. The crude product was purified by chromatography using ethyl acetate and heptane to afford EX-112. $^1$H NMR (400 MHz, DMSO) δ 12.12 (s, 1H), 9.68 (s, 1H), 8.40 (d, J=2.1 Hz, 1H), 8.19 (dd, J=8.9, 2.1 Hz, 1H), 7.51 (s, 2H), 7.48 (d, J=5.9 Hz, 1H), 7.36 (d, J=8.4 Hz, 1H), 7.31 (d, J=2.3 Hz, 1H), 7.27 (dd, J=8.4, 2.3 Hz, 1H), 4.75 (d, J=9.6 Hz, 1H), 4.46 (d, J=9.5 Hz, 1H), 3.61-3.45 (m, 2H), 2.79 (t, J=6.3 Hz, 2H), 2.49-2.42 (m, 2H), 2.28-2.15 (m, 2H), 2.02 (dd, J=8.5, 3.2 Hz, 1H), 1.85 (t, J=4.6 Hz, 1H), 1.77 (dt, J=9.0, 4.4 Hz, 1H), 1.07 (t, J=7.5 Hz, 3H).

A reactor was charged with EX-112 (1.0 equiv., scaling factor), iron (10.0 equiv.), and acetic acid (10 volumes). The mixture was agitated at about 70° C. for about 2 hours. The reaction mixture was cooled to about 20° C. and charged with sodium triacetoxyborohydride (2.0 equiv.). The mixture was agitated at about 20° C. for approximately 30 minutes. The reaction mixture was diluted with ethyl acetate (150 volumes) and filtered through Celite. The organic layer was washed with two portions of water (40 volumes). The organic layer was dried over sodium sulfate, filtered, and concentrated to dryness. The crude product was purified by chromatography using ethyl acetate, heptane, and acetic acid to afford EX-113. $^1$H NMR (400 MHz, DMSO) δ 12.09 (s, 1H), 7.83 (d, J=8.5 Hz, 1H), 7.41 (d, J=2.1 Hz, 1H), 7.32 (s, 2H), 7.25 (dd, J=8.3, 2.1 Hz, 2H), 7.15 (d, J=2.4 Hz, 1H), 6.79 (d, J=8.2 Hz, 1H), 5.96-5.85 (m, 1H), 4.12-4.02 (m, 2H), 3.50-3.40 (m, 2H), 3.31 (d, J=4.4 Hz, 2H), 3.26 (d, J=3.3 Hz, 1H), 3.19 (dd, J=13.6, 4.6 Hz, 1H), 2.71 (q, J=6.7, 5.9 Hz, 2H), 2.22 (dd, J=15.1, 7.6 Hz, 1H), 1.83 (d, J=11.8 Hz, 1H), 1.74 (d, J=24.7 Hz, 2H), 1.55 (t, J=10.3 Hz, 1H), 1.07 (d, J=6.3 Hz, 3H).

Oxidative Cleavage of EX-9 to EX-114:

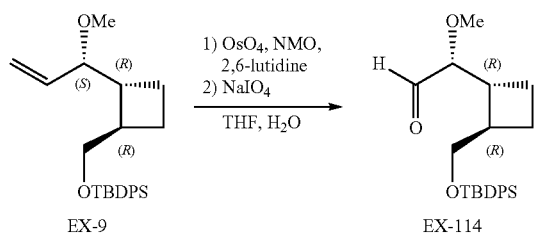

EX-9 → EX-114

A reactor charged with EX-9 (1.0 equiv, scaling factor), methylmorpholine N-oxide (1.5 equiv), tetrahydrofuran (10 volumes) and water (1 volume) before agitating. Once homogeneous, 2,6-lutidine (2.0 equiv) and osmium tetroxide (0.05 equiv, 4 wt % in water) were added and the reaction stirred at about 20° C. for about 3 days. At that time, sodium periodate (2.5 equiv) was added and stirred for about 6 hours. After which, the reaction was diluted with ethyl acetate (60 volumes) and water (30 volumes) before it was charged to a separatory funnel and the resulting layers separated. The aqueous layer was extracted with ethyl acetate (twice, 100 volumes total) and the organic layer washed with 30 wt % aqueous solution of citric acid (once, 30 volumes), water (once, 30 volumes) and saturated aqueous sodium chloride (once, 30 volumes) before drying over sodium sulfate. The dried organic layers were then filtered and concentrated to afford EX-114. The crude material was used directly in the preparation of EX-115. $^1$H NMR (400 MHz, CDCl$_3$) δ 9.51 (d, J=2.5 Hz, 1H), 7.70-7.58 (m, 5H), 7.39-7.27 (m, 8H), 3.61-3.47 (m, 2H), 3.45-3.36 (m, 1H), 3.34 (s, 3H), 2.55-2.43 (m, 2H), 1.89-1.68 (m, 4H), 1.01 (s, 12H).

Seyferth-Gilbert Homologation of EX-114 to EX-115:

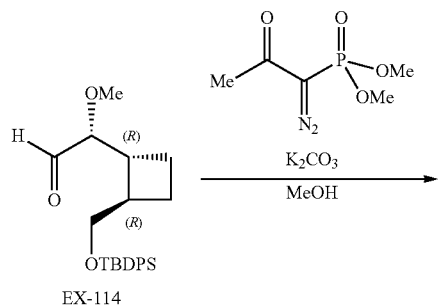

A reactor was charged with EX-114 (1.0 equiv, scaling factor), potassium carbonate (3.5 equiv) and methanol (100 volumes) before agitating. Once homogeneous, dimethyl (1-azoacetonyl)phosphonate (1.5 quiv, 10 wt % solution in acetonitrile) was charged and then stirred at about 20° C. for about 14 hours. At that time, the reaction was diluted with methyl tert-butyl ether (200 volumes) before transferring the mixture to a separatory funnel. The organic layer was washed with a 2.5 wt % aqueous solution of sodium bicarbonate (twice, 200 volumes total) and saturated aqueous sodium chloride (once, 100 volumes) before drying it over sodium sulfate. The dried organic layers were then filtered, concentrated and purified by column chromatography using ethyl acetate and heptane to afford EX-115. $^1$H NMR (400 MHz, CDCl$_3$) δ 7.71 (dt, J=8.0, 2.1 Hz, 4H), 7.50-7.36 (m, 6H), 3.97 (dd, J=6.0, 2.1 Hz, 1H), 3.69 (d, J=5.4 Hz, 2H), 3.42 (s, 3H), 2.66-2.42 (m, 2H), 2.02-1.74 (m, 4H), 1.11 (s, 9H).

Methylation of EX-115 to EX-116:

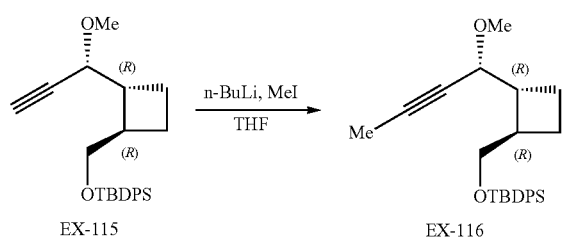

A reactor was charged with EX-115 (1.0 equiv, scaling factor) and tetrahydrofuran (3.0 volumes) before cooling the flask to around −80° C. The resulting solution was charged with n-butyl lithium (2.0 equiv, 2.5 M in hexanes) aged for around one hour around −80° C. before charging methyl iodide (2.0 equiv) and allowed to warm to about 20° C. overnight. At which time, triethylamine (1.5 equiv), methyl tert-butyl ether (50 volumes) and water (50 volumes) were added before transferring to the crude reaction to a separatory funnel and separating the resulting phases. The aqueous layer was extracted with methyl tert-butyl ether (twice, 150 volumes total) and the organic layer washed with a 0.1 M aqueous solution of hydrochloric acid (50 volumes), water (50 volumes) and saturated aqueous sodium chloride (50 volumes) before drying over sodium sulfate. The dried organic layers were then filtered and concentrated to afford EX-116. The crude material was directly used in the preparation of EX-117. $^1$H NMR (400 MHz, CDCl$_3$) δ 7.69 (ddt, J=6.6, 2.6, 1.6 Hz, 5H), 7.48-7.34 (m, 5H), 3.90 (dq, J=6.1, 2.1 Hz, 1H), 3.72-3.63 (m, 2H), 3.37 (s, 3H), 3.23 (s, 3H), 2.57-2.39 (m, 2H), 1.88 (dd, J=7.5, 2.5 Hz, 4H) 1.08 (s, 9H).

Desilylation of EX-116 to EX-117:

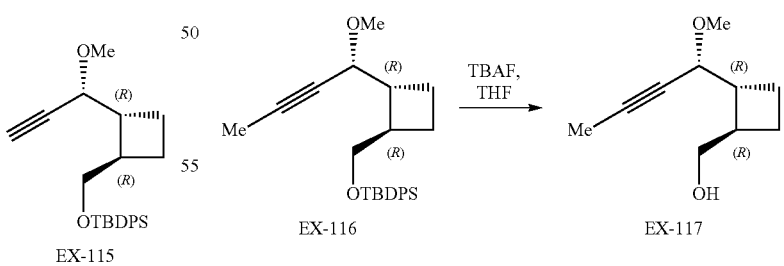

A reactor was charged with EX-116 (1.0 equiv, scaling factor) and tetrahydrofuran (10 volumes) at about 25° C. Tetrabutylammonium fluoride (3.0 equiv, 1 M in tetrahydrofuran) was then added and agitated for about 20 h. At which time, water (50 volumes) was added before transferring to a separatory funnel and separating the resulting phases. The aqueous layer was extracted with ethyl acetate (twice, 200 volumes total) and the combined organic layer washed with saturated aqueous sodium chloride (once, 100 volumes) before drying over sodium sulfate. The dried organic layers were then filtered, concentrated and purified by column chromatography using ethyl acetate and heptane to afford EX-117. ¹H NMR (400 MHz, CDCl₃) δ 3.72 (dd, J=9.0, 2.1 Hz, 1H), 3.56 (dd, J=10.5, 4.3 Hz, 1H), 3.47-3.35 (m, 4H), 2.37-2.17 (m, 2H), 2.05-1.79 (m, 6H), 1.71 (dq, J=10.5, 9.2, 8.6 Hz, 1H), 1.64-1.47 (m, 1H).

Oxidation of EX-117 to EX-118:

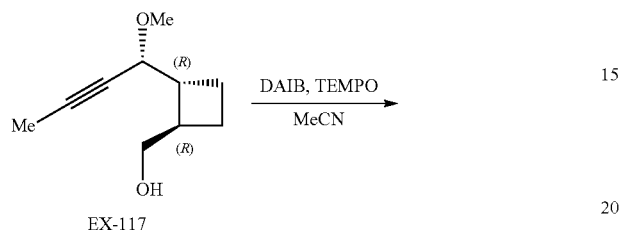

A reactor was charged with EX-117 (1.0 equiv, scaling factor), acetonitrile (18 volumes), iodobenzene diacetate (1.1 equiv) and tetramethylpiperidinyloxyl (0.075 equiv) at around 20° C. before agitating for about 20 hours. After which, the resulting solution contained EX-118 and was used directly in the preparation of EX-119. ¹H NMR (400 MHz, CDCl₃) δ 9.75 (d, J=1.7 Hz, 1H), 3.98-3.86 (m, 1H), 3.42 (s, 3H), 3.18 (q, J=8.7 Hz, 1H), 2.91-2.74 (m, 2H), 2.12-1.88 (m, 6H).

Reductive Amination of EX-118 to EX-119:

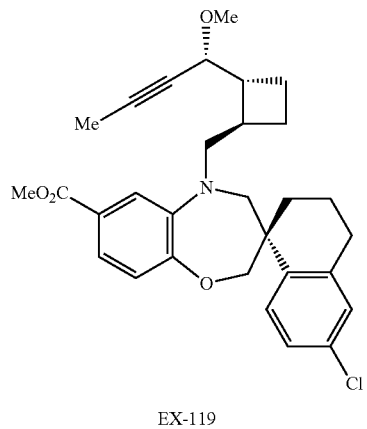

A reactor was charged with EX-12 (1.1 equiv), EX-118 (1 equiv, scaling factor) dissolved in acetonitrile, acetonitrile (40 volumes), magnesium sulfate (200 wt %), triethylsilane (2.0 equiv) and TFA (2 equiv) and agitated at about 20° C. for about 3 hours. The reaction mixture was diluted with dichloromethane (250 volumes) and filtered through Celite. The organic layer was washed with 2M aqueous potassium carbonate (400 volumes) and water (400 volumes). The organic layer was dried over magnesium sulfate, filtered, and concentrated to dryness. The crude product was purified by chromatography using ethyl acetate and heptane to afford EX-119. ¹H NMR (400 MHz, Chloroform-d) δ 7.75 (d, J=8.5 Hz, 1H), 7.50-7.41 (m, 2H), 7.21 (dd, J=8.5, 2.2 Hz, 1H), 7.13 (d, J=2.2 Hz, 1H), 6.96 (d, J=8.1 Hz, 1H), 4.21-4.08 (m, 2H), 3.93 (s, 3H), 3.75-3.62 (m, 2H), 3.48 (s, 3H), 3.36 (d, J=14.3 Hz, 1H), 3.28 (dd, J=14.9, 8.7 Hz, 1H), 2.86-2.77 (m, 2H), 2.64 (pd, J=8.8, 3.3 Hz, 1H), 2.34 (p, J=8.4 Hz, 1H), 2.10-1.99 (m, 2H), 1.98-1.80 (m, 7H), 1.83-1.64 (m, 1H), 1.62-1.51 (m, 1H), 1.36 (t, J=6.8 Hz, 1H).

Propynyl Magnesium Bromide Addition of EX-120 to EX-121 and EX-122:

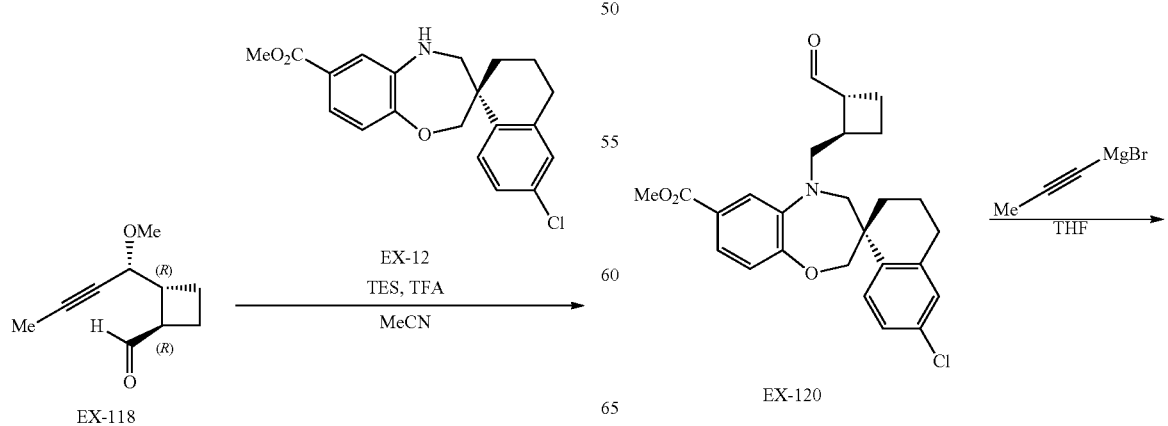

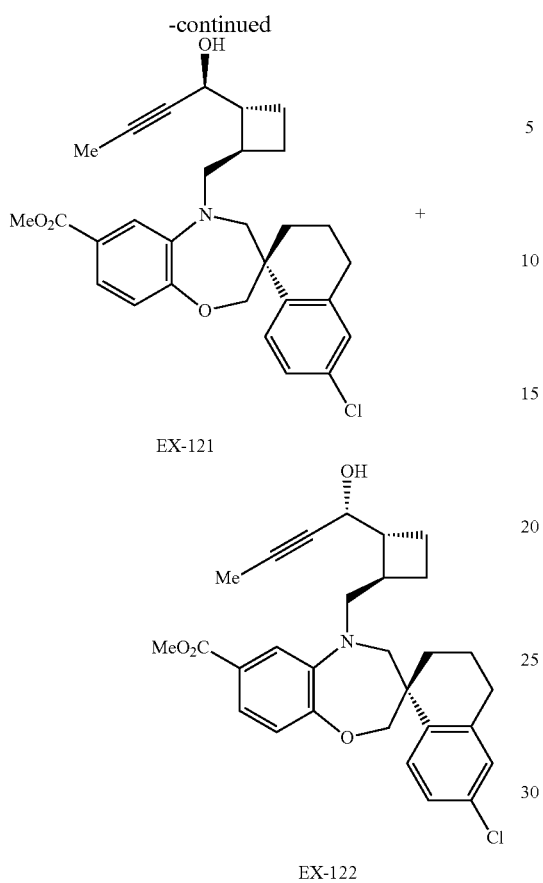

EX-121

EX-122

A reactor was charged with EX-120 (1.0 equiv, scaling factor), and tetrahydrofuran (18 V) before the solution was agitated and cooled to around −80° C. The contents were charged with propenyl magnesium bromide (1.5 equiv, 0.5 M solution in tetrahydrofuran), stirred at around −80° C. for about an hour before warming to about 20° C. After which the reaction was treated with a 25 wt % aqueous solution of ammonium chloride (30 volumes) and then transferred to a separatory funnel. The resulting layers were separated. The aqueous layer was extracted with ethyl acetate (twice, 30 volumes total), before the combined organic layers were washed with saturated aqueous sodium chloride (once, 10 volumes) and then dried over sodium sulfate. The dried organic layers were then filtered, concentrated and purified by column chromatography using ethyl acetate and heptane to afford EX-121 and EX-122. EX-121: $^1$H NMR (400 MHz, CDCl$_3$) δ 7.74 (d, J=8.5 Hz, 1H), 7.57 (d, J=1.9 Hz, 1H), 7.41 (dd, J=8.2, 1.9 Hz, 1H), 7.17 (dd, J=8.5, 2.3 Hz, 1H), 7.09 (d, J=2.3 Hz, 1H), 6.93 (d, J=8.2 Hz, 1H), 4.41 (tt, J=4.6, 2.4 Hz, 1H), 4.15-4.08 (m, 2H), 3.91 (s, 3H), 3.80 (dd, J=15.0, 2.7 Hz, 1H), 3.65 (d, J=14.2 Hz, 1H), 3.33 (d, J=14.3 Hz, 1H), 3.23 (dd, J=14.9, 9.0 Hz, 1H), 3.05 (d, J=4.4 Hz, 1H), 2.85-2.67 (m, 3H), 2.33 (qd, J=8.6, 6.1 Hz, 1H), 2.13-1.97 (m, 2H), 2.01-1.86 (m, 2H), 1.91-1.72 (m, 1H), 1.74-1.62 (m, 1H), 1.59-1.47 (m, 1H), 1.35-1.26 (m, 4H). EX-122: $^1$H NMR (400 MHz, Chloroform-d) δ 7.73 (d, J=8.5 Hz, 1H), 7.62 (d, J=2.0 Hz, 1H), 7.39 (dd, J=8.2, 2.0 Hz, 1H), 7.18 (dd, J=8.5, 2.4 Hz, 1H), 7.10 (d, J=2.3 Hz, 1H), 6.92 (d, J=8.2 Hz, 1H), 4.33 (dq, J=6.9, 2.2 Hz, 1H), 4.19-4.06 (m, 2H), 3.91 (s, 3H), 3.83 (dd, J=15.0, 2.6 Hz, 1H), 3.63 (d, J=14.2 Hz, 1H), 3.28 (d, J=14.2 Hz, 1H), 3.18 (dd, J=15.0, 8.7 Hz, 1H), 2.78 (q, J=5.4 Hz, 2H), 2.65-2.51 (m, 1H), 2.30 (p, J=8.4 Hz, 1H), 2.06-1.46 (m, 12H).

Methylation of EX122 to EX119:

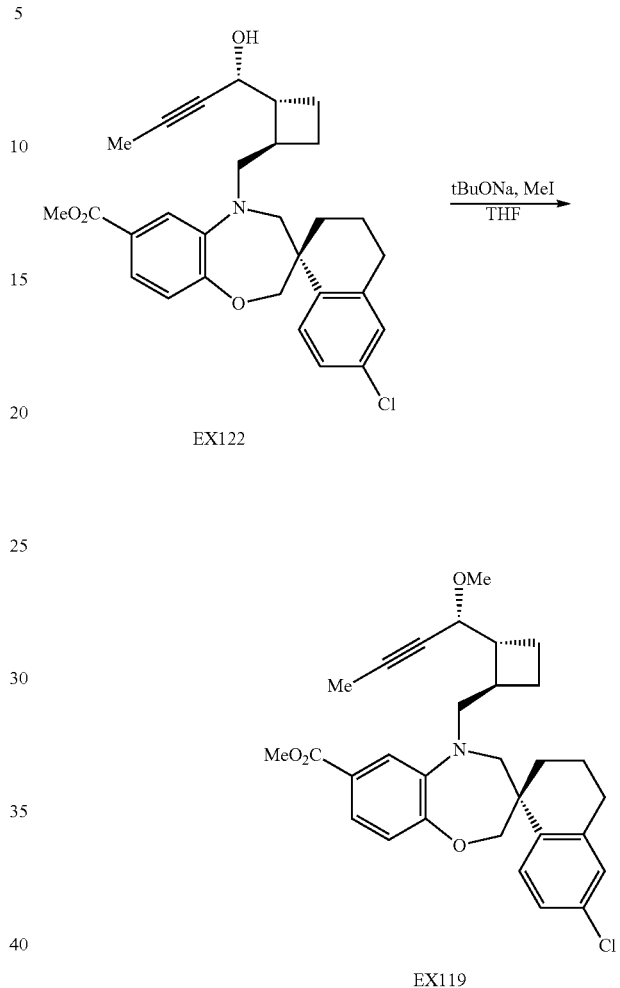

A reactor was charged with EX122 (1 equiv, scaling factor) and tetrahydrofuran (10 volumes) and iodomethane (5.0 equiv) and cooled to about 0° C. Sodium tert-butoxide (1.5 equiv, 2 M in tetrahydrofuran) was charged and the mixture was agitated at about 0° C. for about 4 h. At which time an addition portion of sodium tert-butoxide (0.25 equiv, 2 M in tetrahydrofuran) was charged at about 0° C. and agitated for about 4 hours. Triethylamine (4.1 equiv) was charged and the mixture was diluted with methyl tert-butyl ether (30 volumes) and water (20 volumes). The layers were separated and the aqueous layer was back-extracted with methyl tert-butyl ether (twice, 35 volumes total). The combined organic layers were washed with a solution of sodium metabisulfite (5 equiv) in water (10 volumes), then saturated aqueous sodium chloride solution (20 volumes), and then dried over magnesium sulfate, filtered, and concentrated. The crude product was purified by chromatography with ethyl acetate and hexanes to afford EX119. $^1$H NMR (400 MHz, CDCl$_3$) δ 7.71 (d, J=8.5 Hz, 1H), 7.47-7.38 (m, 2H), 7.18 (dd, J=8.5, 2.3 Hz, 1H), 7.10 (d, J=2.3 Hz, 1H), 6.93 (d, J=8.2 Hz, 1H), 4.19-4.05 (m, 2H), 3.90 (s, 3H), 3.77-3.73 (m, 1H), 3.67-3.63 (m, 1H), 3.40-3.24 (m, 5H), 2.80-2.76 (m, 3H), 2.31 (tq, J=8.7, 5.3 Hz, 1H), 2.06-1.71 (m, 10H), 1.53-1.42 (t, J=12.7 Hz, 1H), 1.28 (t, J=7.1 Hz, 1H).

Saponification of EX-119 to EX-123:

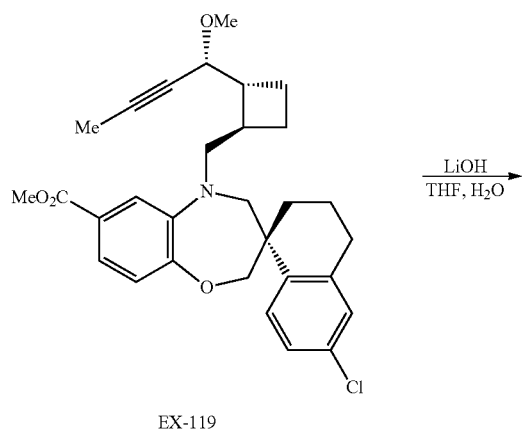

EX-119

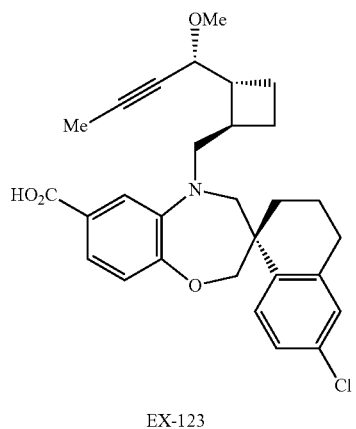

EX-123

A reactor was charged with EX-119 (1.0 equiv, scaling factor), tetrahydrofuran (20 volumes), water (20 volumes) and lithium hydroxide (10 equiv) before the reaction was heated (50° C.) for about 5 days. At that time, the reaction was cooled to 20° C. before charging 1M aqueous hydrochloric acid (60 volumes), the reaction was transferred to a separatory funnel and the resulting layers separated. The aqueous layer was extracted with ethyl acetate (thrice, 60 volumes total), before the combined organic layers dried over sodium sulfate. The dried organic layers were then filtered, concentrated and purified by column chromatography using ethyl acetate and heptane to afford EX-123. $^1$H NMR (400 MHz, CDCl$_3$) δ 12.18 (s, 1H), 7.73 (d, J=8.4 Hz, 1H), 7.56-7.47 (m, 2H), 7.19 (d, J=8.3 Hz, 1H), 7.13-7.08 (m, 1H), 6.96 (d, J=8.1 Hz, 1H), 4.20-4.08 (m, 2H), 3.90 (d, J=7.1 Hz, 1H), 3.79-3.68 (m, 2H), 3.47 (s, 3H), 3.36 (d, J=14.2 Hz, 1H), 3.32-3.21 (m, 1H), 2.79 (q, J=6.3, 5.5 Hz, 2H), 2.61 (q, J=8.4, 7.8 Hz, 1H), 2.30 (q, J=8.5 Hz, 1H), 2.06 (d, J=11.9 Hz, 3H), 1.93 (t, J=8.6 Hz, 3H), 1.88-1.66 (m, 4H), 1.60-1.48 (m, 1H).

SNAr of 4-Bromo-1-Fluoro-2-Nitrobenzene with EX-11 to Give EX-124:

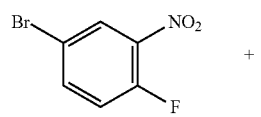

+

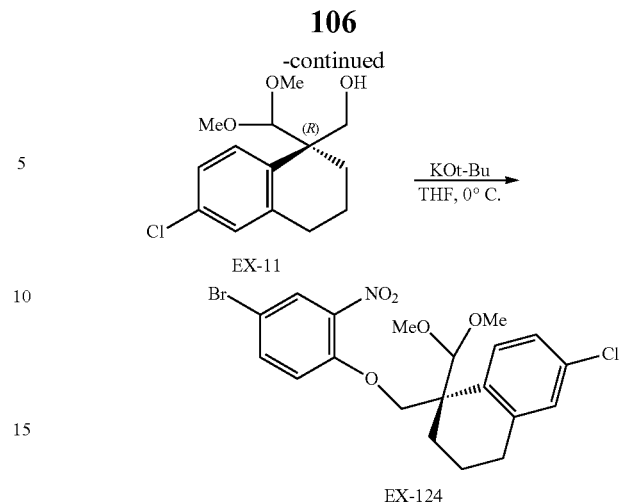

A reactor was charged with EX-11 (1.0 equiv, scaling factor), 4-bromo-1-fluoro-2-nitrobenzene (1.05 equiv), and tetrahydrofuran (10 volumes). The reaction mixture was charged with a solution of potassium tert-butoxide in tetrahydrofuran (2.4 equiv) over about 10 minutes. The reaction mixture was agitated at about 20° C. for about 1 hour. The reaction mixture was quenched with water (10 volumes) and extracted with ethyl acetate (40 volumes). The organic layer was washed with brine (20 volumes), dried over magnesium sulfate, filtered, and concentrated. The crude product was purified by chromatography using ethyl acetate and heptane to afford EX-124. $^1$H NMR (400 MHz, Chloroform-d) δ 8.04 (d, J=2.5 Hz, 1H), 7.71 (d, J=8.4 Hz, 1H), 7.62 (dd, J=8.9, 2.5 Hz, 1H), 7.20-7.09 (m, 2H), 6.96 (d, J=8.9 Hz, 1H), 4.75 (s, 1H), 4.20 (d, J=8.6 Hz, 1H), 4.10 (d, J=8.5 Hz, 1H), 3.50 (s, 3H), 3.43 (s, 3H), 2.87-2.68 (m, 2H), 2.19-2.04 (m, 1H), 2.01-1.87 (m, 2H), 1.79-1.64 (m, 1H).

Acetal Hydrolysis and Reductive Cyclization of EX-124 to EX-126:

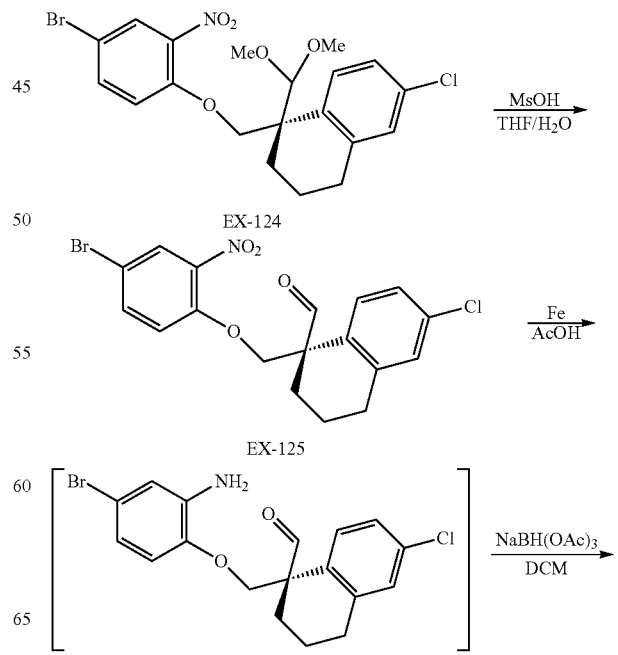

-continued

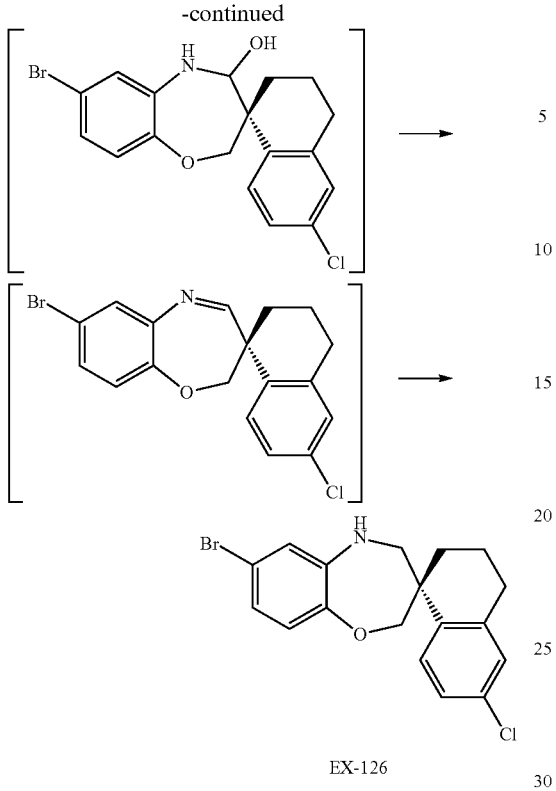

EX-126

A vial was charged with EX-124 (1.0 equiv, scaling factor), water (2 volumes) and tetrahydrofuran (10 volumes). The solution was charged with methanesulfonic acid (4 equiv.) and agitated at about 50° C. for about 48 hours. The reaction mixture was cooled to about 20° C. and charged with saturated aqueous sodium bicarbonate (10 volumes) before extracting the crude reaction mixture with ethyl acetate (30 volumes). The organic layer was washed with water (15 volumes). The organic layer was dried over magnesium sulfate, filtered, and concentrated to dryness. The crude product (EX-125) was used directly in the next step. A vial was charged with EX-125 (1.0 equiv, scaling factor), iron (10 equiv), and acetic acid (10 volumes). The mixture was agitated at about 50° C. for about 18 hours. The reaction mixture was cooled to about 20° C. and diluted with dichloromethane (20 volumes) before filtering the reaction mixture through a pad of Celite. The solution was then charged with sodium triacetoxyborohydride (1.2 equiv) and agitated at about 20° C. for approximately 3 hours. The reaction mixture quenched with saturated aqueous sodium bicarbonate (10 volumes) before extracting the resulting solution with dichloromethane (100 volumes). The organic layer was dried over magnesium sulfate, filtered, and concentrated to dryness. The crude product was purified by chromatography using ethyl acetate and heptane to afford EX-126. $^1$H NMR (400 MHz, Chloroform-d) δ 7.85 (d, J=8.4 Hz, 1H), 7.19 (dd, J=8.5, 2.4 Hz, 1H), 7.10 (d, J=2.3 Hz, 1H), 6.86-6.74 (m, 3H), 4.14 (q, J=12.2 Hz, 2H), 3.86 (s, 1H), 3.50 (d, J=13.7 Hz, 1H), 3.33 (d, J=13.6 Hz, 1H), 2.75 (t, J=6.3 Hz, 2H), 1.93-1.53 (m, 4H).

Reductive Amination of EX-126 with EX-11 to EX-127:

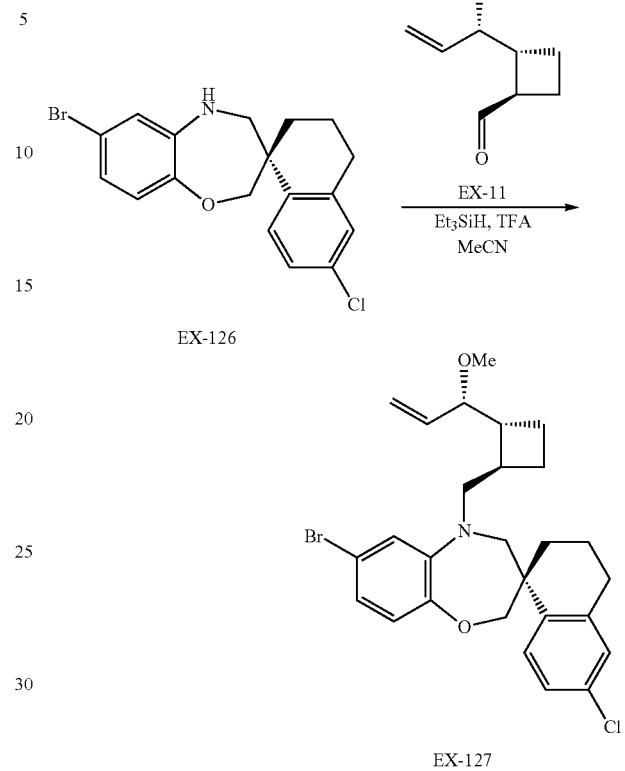

A vial was charged with EX-126 (1 equiv, scaling factor), EX-11 (1.2 equiv, 6.5 wt % solution in acetonitrile), trifluoroacetic acid (0.5 equiv.), triethylsilane (2.0 equiv.) and acetonitrile (10 volumes) before agitating at about 20° C. for about 24 hours. The mixture was then concentrated to dryness and purified directly by chromatography using ethyl acetate and heptane to afford EX-127. $^1$H NMR (400 MHz, Chloroform-d) δ 7.72 (d, J=8.5 Hz, 1H), 7.19 (dd, J=8.5, 2.4 Hz, 1H), 7.09 (d, J=2.3 Hz, 1H), 6.92 (d, J=1.3 Hz, 1H), 6.77 (d, J=1.5 Hz, 2H), 5.64-5.50 (m, 1H), 5.29-5.19 (m, 2H), 4.10-3.97 (m, 2H), 3.79-3.68 (m, 2H), 3.50 (t, J=8.4 Hz, 1H), 3.42 (s, 3H), 3.25 (d, J=14.3 Hz, 1H), 3.06 (dd, J=15.0, 9.8 Hz, 1H), 2.82-2.73 (m, 2H), 2.49 (q, J=8.7 Hz, 1H), 2.05-1.57 (m, 8H), 1.45 (t, J=12.5 Hz, 1H).

Carboxylation of EX-127 to EX-60:

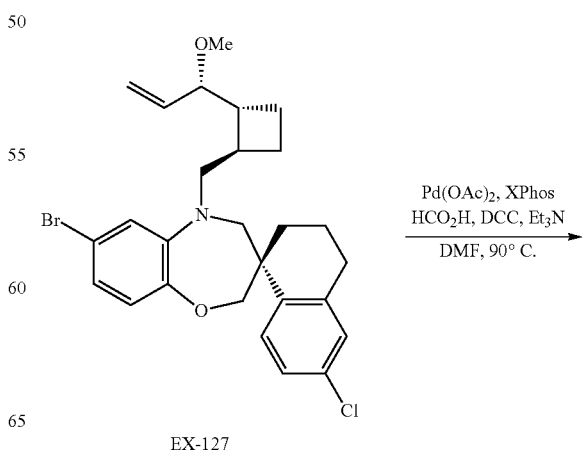

EX-127

-continued

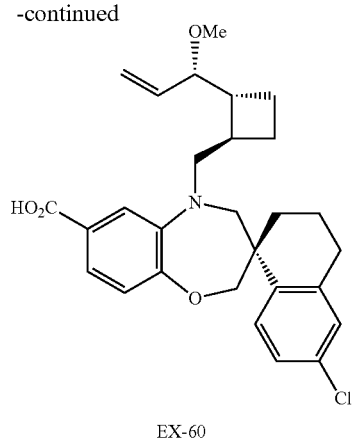

EX-60

A vial was charged with EX-127 (1.0 equiv, scaling factor), palladium acetate (0.1 equiv), 4,5-bis(diphenylphosphino)-9,9-dimethylxanthene (0.1 equiv), dicyclohexylcarbodiimide (0.2 equiv. of a 1.0 M solution in dichloromethane), dimethylformamide (20 volumes), formic acid (3.5 equiv) and triethylamine (2.0 equiv) before sealing the vial and heating to about 90° C. for about 18 hours. The reaction was allowed to cool to about 20° C. before concentrating to dryness and purifying directly by chromatography using ethyl acetate and heptane to afford EX-60. $^1$H NMR (400 MHz, Chloroform-d) δ 7.71 (d, J=8.5 Hz, 1H), 7.54-7.42 (m, 2H), 7.17 (dd, J=8.5, 2.3 Hz, 1H), 7.08 (d, J=2.4 Hz, 1H), 6.93 (d, J=8.2 Hz, 1H), 5.64-5.51 (m, 1H), 5.26-5.15 (m, 2H), 4.18-4.05 (m, 2H), 3.76 (dd, J=14.8, 3.3 Hz, 1H), 3.67 (d, J=14.4 Hz, 1H), 3.49 (t, J=8.1 Hz, 1H), 3.39-3.27 (m, 4H), 3.19 (dd, J=14.9, 9.4 Hz, 1H), 2.87-2.68 (m, 2H), 2.54 (tq, J=11.8, 4.7, 3.0 Hz, 1H), 2.17-1.96 (m, 3H), 1.97-1.73 (m, 3H), 1.73-1.41 (m, 3H).

SNAr of 4-Fluoro-3-Nitrobenzonitrile with EX-11 to Give EX-128:

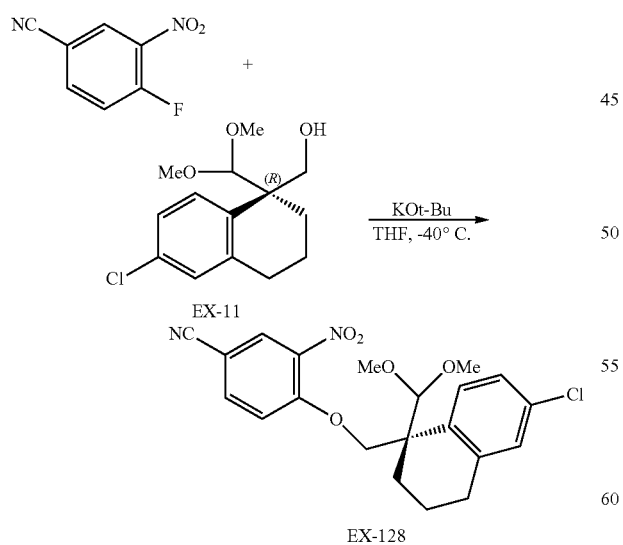

A vial was charged with EX-11 (1.0 equiv, scaling factor), 4-fluoro-3-nitrobenzonitrile (1.2 equiv), and tetrahydrofuran (10 volumes) before cooling the vial to about −40° C. The reaction mixture was charged with a solution of potassium tert-butoxide in tetrahydrofuran (1.2 equiv) over about 10 minutes. The reaction mixture was agitated at about −40° C. for about 1 hour. The reaction mixture warmed to about 20° C. before it was quenched with water (10 volumes) and extracted with ethyl acetate (40 volumes). The organic layer was washed with brine (20 volumes), dried over magnesium sulfate, filtered, and concentrated. The crude product was purified by chromatography using ethyl acetate and heptane to afford EX-128. $^1$H NMR (400 MHz, Chloroform-d) δ 8.12 (d, J=2.1 Hz, 1H), 7.72 (dd, J=8.7, 2.2 Hz, 1H), 7.61-7.54 (m, 1H), 7.12-7.01 (m, 3H), 4.62 (s, 1H), 4.24-4.09 (m, 2H), 3.40 (s, 3H), 3.34 (s, 3H), 2.68 (td, J=15.8, 14.2, 7.5 Hz, 2H), 2.04 (t, J=10.5 Hz, 1H), 1.86 (t, J=9.0 Hz, 2H), 1.47 (s, 1H).

Acetal Hydrolysis and Reductive Cyclization of EX-128 to EX-130:

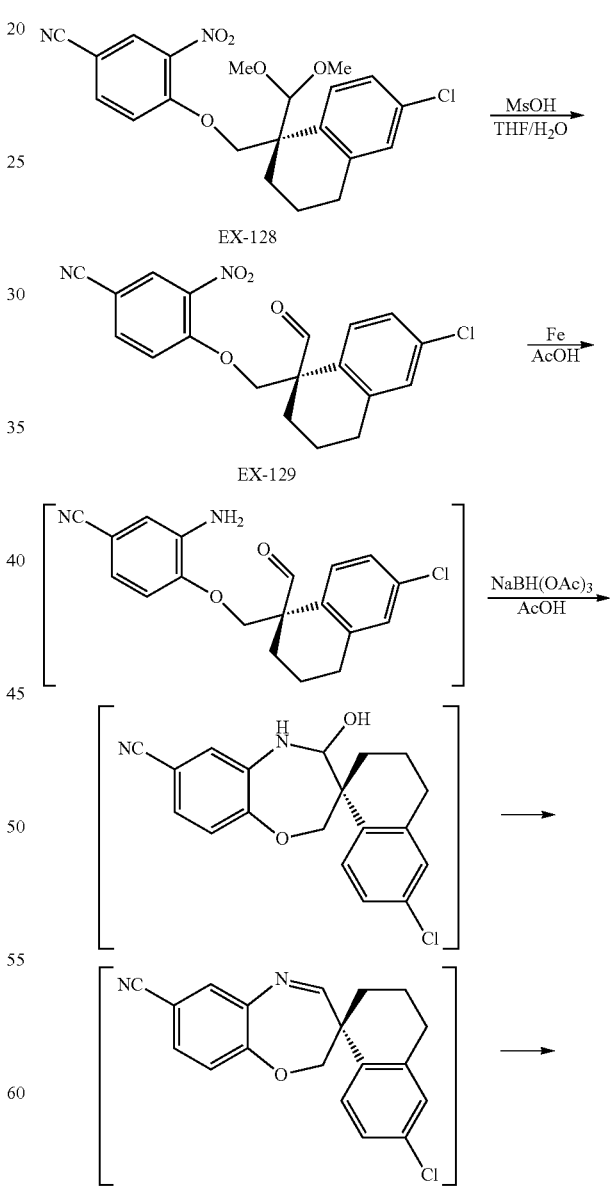

-continued

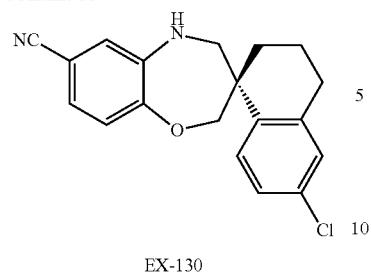

EX-130

A vial was charged with EX-128 (1.0 equiv, scaling factor), water (2 volumes) and tetrahydrofuran (10 volumes). The solution was charged with methanesulfonic acid (4 equiv.) and agitated at about 50° C. for about 48 hours. The reaction mixture was cooled to about 20° C. and charged with saturated aqueous sodium bicarbonate (10 volumes) before extracting the crude reaction mixture with ethyl acetate (30 volumes). The organic layer was washed with water (15 volumes). The organic layer was dried over magnesium sulfate, filtered, and concentrated to dryness. The crude product (EX-129) was used directly in the next step.

A vial was charged with EX-129 (1.0 equiv, scaling factor), iron (10 equiv), and acetic acid (10 volumes). The mixture was agitated at about 50° C. for about 18 hours. The reaction mixture was cooled to about 20° C. and diluted with dichloromethane (20 volumes) before filtering the reaction mixture through a pad of Celite. The solution was then charged with sodium triacetoxyborohydride (1.2 equiv) and agitated at about 20° C. for about 3 hours. The reaction mixture quenched with saturated aqueous sodium bicarbonate (10 volumes) before extracting the resulting solution with dichloromethane (100 volumes). The organic layer was dried over magnesium sulfate, filtered, and concentrated to dryness. The crude product was purified by chromatography using ethyl acetate and heptane to afford EX-130. $^1$H NMR (400 MHz, Chloroform-d) δ 7.83 (d, J=8.5 Hz, 1H), 7.19 (dd, J=8.5, 2.4 Hz, 1H), 7.10 (d, J=2.3 Hz, 1H), 7.03 (dd, J=8.2, 1.9 Hz, 1H), 6.97-6.88 (m, 2H), 4.02 (s, 1H), 3.51 (d, J=13.7 Hz, 1H), 3.36 (d, J=13.8 Hz, 1H), 2.76 (dd, J=7.3, 5.3 Hz, 2H), 1.97-1.72 (m, 3H), 1.66 (ddd, J=12.2, 9.6, 2.7 Hz, 1H), 1.34-1.21 (m, 2H).

Reductive Amination of EX-130 with EX-11 to EX-131:

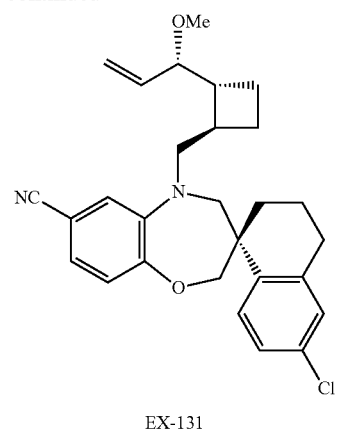

EX-131

A vial was charged with EX-130 (1 equiv, scaling factor), EX-11 (1.2 equiv, 6.5 wt % solution in acetonitrile), trifluoroacetic acid (0.5 equiv.), triethylsilane (2.0 equiv.) and acetonitrile (10 volumes) before agitating at about 20° C. for about 24 hours. The mixture was then concentrated to dryness and purified directly by chromatography using ethyl acetate and heptane to afford EX-131. $^1$H NMR (400 MHz, Chloroform-d) δ 7.62 (d, J=8.5 Hz, 1H), 7.10 (dd, J=8.5, 2.3 Hz, 1H), 7.00 (dd, J=6.0, 2.1 Hz, 2H), 6.93-6.80 (m, 2H), 5.57-5.40 (m, 1H), 5.25-5.07 (m, 2H), 4.01 (s, 2H), 3.79-3.53 (m, 2H), 3.49-3.07 (m, 5H), 3.06-2.83 (m, 1H), 2.78-2.60 (m, 2H), 2.45-2.26 (m, 1H), 2.05-1.28 (m, 8H), 0.86-0.74 (m, 1H).

Nitrile Hydrolysis of EX-131 to EX-60:

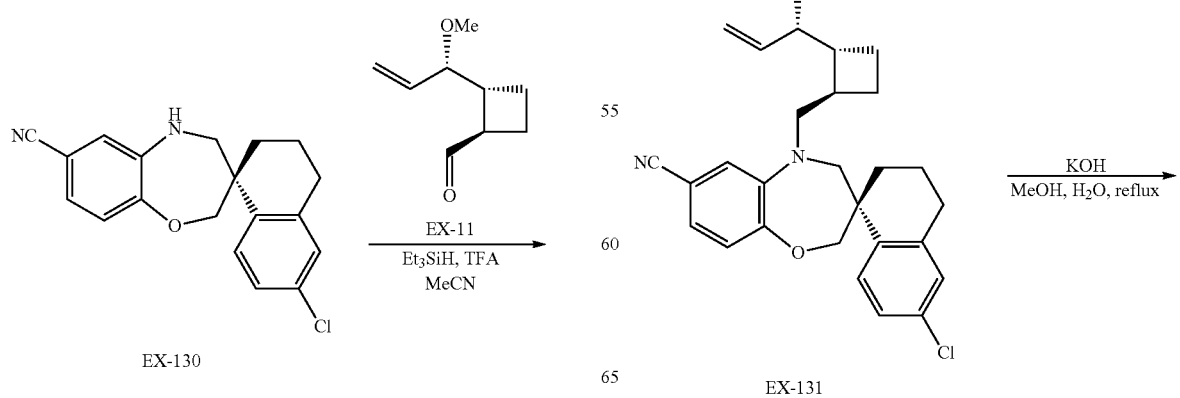

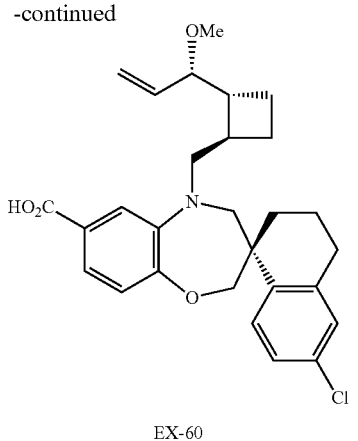

EX-60

A vial was charged with EX-131 (1 equiv, scaling factor), methanol (40 volumes), water (4 volumes) and potassium hydroxide (10 equiv.) before agitating at about 110° C. for about 48 hours. The reaction mixture was then charged with aqueous HCl (1.0 M, 20 volumes) and heated to about 100° C. for about 2 hours before cooling down to about 20° C. The reaction was then concentrated and purified directly by chromatography using ethyl acetate and heptane to afford EX-60.

Acetal Formation and Acetate Hydrolysis of EX-132 to EX-133:

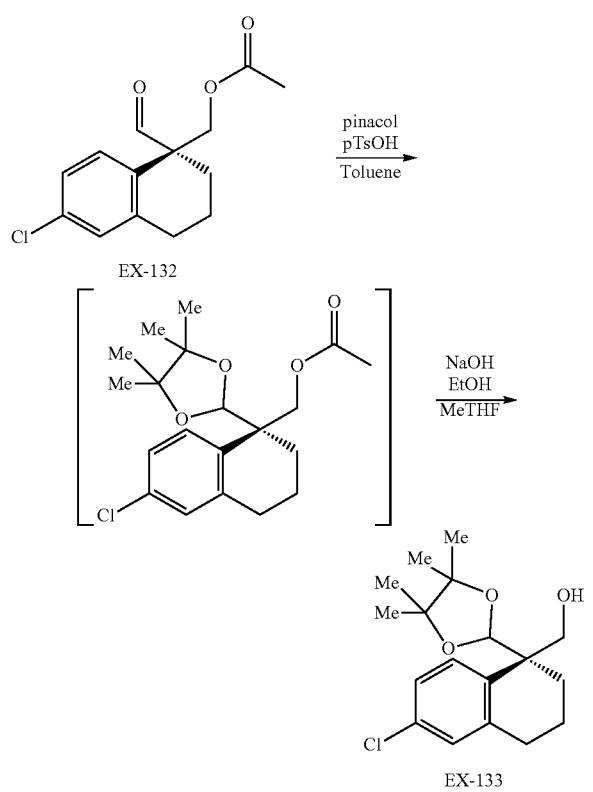

A reactor fitted with a Dean-Stark apparatus was charged with EX-132 (1.0 equiv, scaling factor), pinacol (2.0 equiv), p-toluenesulfonic acid (0.05 equiv), and toluene (15 volumes). The reaction mixture was heated to about 45° C. and partial vacuum was applied. The mixture was agitated for about 24 h. The mixture was concentrated to dryness and the crude material was diluted with MeTHF (10 volumes). An aqueous solution of 1N NaOH (3 equiv) and EtOH (4 volumes) were charged and the resulting biphasic mixture was agitated for about 5 h. The layers were separated, and the organic layer was washed with an aqueous solution of NaCl (15 volumes). The organic layer was concentrated to dryness and the resulting residue was dissolved in EtOH (21 volumes). Water (37 volumes) was added in a dropwise fashion. The resulting slurry was filtered, rinsed with water (10 volumes) and dried to give EX-133. $^1$H NMR (400 MHz, CDCl$_3$): δ 7.37 (d, J=8.4 Hz, 1H), 7.10 (d, J=8.9 Hz, 2H), 5.27 (s, 1H), 3.89 (d, J=11.3 Hz, 1H), 3.56 (d, J=11.4 Hz, 1H), 2.74 (q, J=7.1, 6.1 Hz, 2H), 2.02-1.87 (m, 3H), 1.82-1.71 (m, 1H), 1.65-1.50 (m, 1H), 1.28-1.10 (m, 12H).

SNAr of 4-Bromo-1-Fluoro-2-Nitrobenzene with EX-133 to Give EX-134:

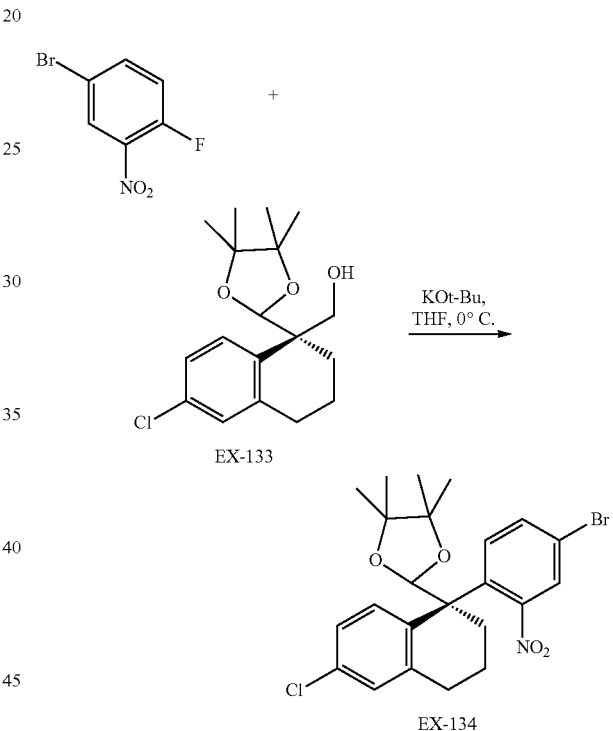

A reactor was charged with EX-133 and tetrahydrofuran (10 volumes) and cooled to about 0° C. Potassium tert-butoxide in tetrahydrofuran (2.5 equiv) was added over about 20 min followed by 4-bromo-1-fluoro-2-nitrobenzene over about 20 min. The reaction mixture was stirred for about 2 h at 0° C. then quenched with water (5 volumes). The mixture was concentrated and then dissolved with ethyl acetate (10 volumes). The organic layer was washed with saturated sodium chloride solution (5 volumes). The phases were separated and the aqueous layer was extracted with ethyl acetate (10 volumes) twice. The combined organic layers was dried over magnesium sulfate, filtered, and concentrated. The crude product was purified by silica gel chromatography using ethyl acetate and heptane to afford EX-134. $^1$H NMR (400 MHz, Chloroform-d) δ 7.97 (d, J=2.4 Hz, 1H), 7.68-7.53 (m, 2H), 7.12 (d, J=7.2 Hz, 2H), 6.96 (d, J=9.0 Hz, 1H), 5.39 (s, 1H), 4.38-4.17 (m, 2H), 2.78 (t, J=6.3 Hz, 2H), 2.26-1.71 (m, 4H), 1.40-0.85 (m, 12H).

Pinacol Hydrolysis of EX-134 to EX-125:

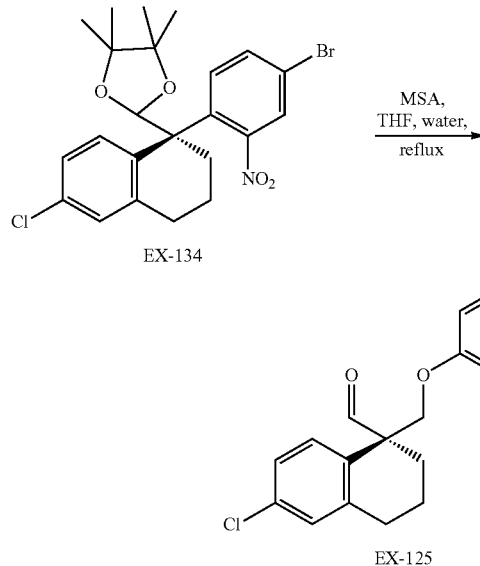

A reactor was charged with EX-134 and tetrahydrofuran (10 volumes) followed by water (2 volumes) and MSA (4 equiv.). The reaction mixture was stirred for about 17 h at reflux then quenched with saturated NaHCO$_3$ in water (7 volumes) at 20° C. The mixture was extracted with ethyl acetate (10 volumes). The phases were separated and the aqueous layer was extracted with ethyl acetate (10 volumes). The combined organic layers was washed with water (10 volumes), dried over magnesium sulfate, filtered, and concentrated. The crude product was purified by silica gel chromatography using ethyl acetate and heptane to afford EX-125. $^1$H NMR (400 MHz, Chloroform-d) δ 9.56 (d, J=0.8 Hz, 1H), 8.01 (d, J=2.5 Hz, 1H), 7.64 (dd, J=8.9, 2.5 Hz, 1H), 7.26-6.98 (m, 4H), 4.52 (d, J=9.0 Hz, 1H), 4.21 (dd, J=8.9, 0.9 Hz, 1H), 2.89 (td, J=7.1, 6.5, 3.4 Hz, 2H), 2.38-2.14 (m, 2H), 2.06-1.88 (m, 2H).

SNAr of 4-Fluoro-3-Nitrobenzonitrile with EX-133 to Give EX-135:

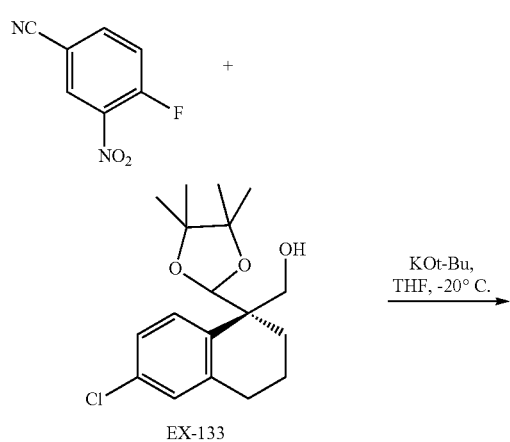

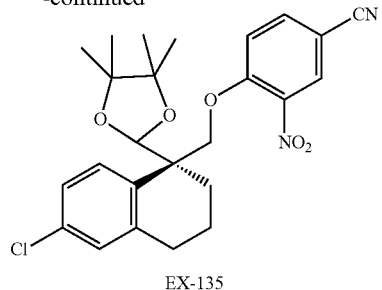

A reactor was charged with EX-133 and tetrahydrofuran (10 volumes) and cooled to about −20° C. Potassium tert-butoxide in tetrahydrofuran (2.5 equiv) was added over about 40 min followed by 4-fluoro-3-nitrobenzonitrile over about 10 min. The reaction mixture was stirred for about 2 h at 0° C. then quenched with water (5 volumes). The mixture was concentrated and then dissolved with ethyl acetate (10 volumes). The organic layer was washed with saturated sodium chloride solution (5 volumes). The phases were separated and the aqueous layer was extracted with ethyl acetate (10 volumes) twice. The combined organic layers were dried over magnesium sulfate, filtered, and concentrated. The crude product was purified by silica gel chromatography using ethyl acetate and heptane to afford EX-135. $^1$H NMR (400 MHz, Chloroform-d) δ 7.97 (d, J=2.1 Hz, 1H), 7.61 (dd, J=8.8, 2.1 Hz, 1H), 7.36 (d, J=8.3 Hz, 1H), 7.04-6.89 (m, 3H), 5.19 (s, 1H), 4.24-4.11 (m, 2H), 2.61 (t, J=6.3 Hz, 2H), 2.10-1.52 (m, 4H), 1.20-0.68 (m, 12H).

Pinacol Hydrolysis of EX-135 to EX-129:

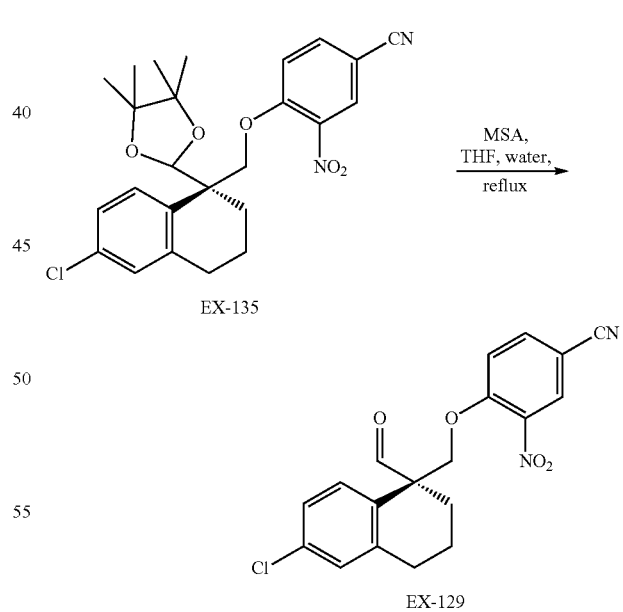

A reactor was charged with EX-135 and tetrahydrofuran (10 volumes) followed by water (2 volumes) and MSA (4 equiv.). The reaction mixture was stirred for about 17 h at reflux and then quenched with saturated NaHCO$_3$ in water (7 volumes) at 20° C. The mixture was extracted with ethyl acetate (10 volumes). The phases were separated and the aqueous layer was extracted with ethyl acetate (10 volumes).

The combined organic layers were washed with water (10 volumes), dried over magnesium sulfate, filtered, and concentrated. The crude product was purified by silica gel chromatography using ethyl acetate and heptane to afford EX-129. ¹H NMR (400 MHz, Chloroform-d) δ 9.53 (d, J=0.8 Hz, 1H), 8.19 (d, J=2.1 Hz, 1H), 7.83 (dd, J=8.8, 2.1 Hz, 1H), 7.27-7.04 (m, 4H), 4.62 (d, J=9.1 Hz, 1H), 4.29 (dd, J=9.1, 1.0 Hz, 1H), 2.97-2.83 (m, 2H), 2.40-1.88 (m, 4H).

Amide Coupling of EX-51 and EX-72 and Deprotection to EX-136:

Step 1:

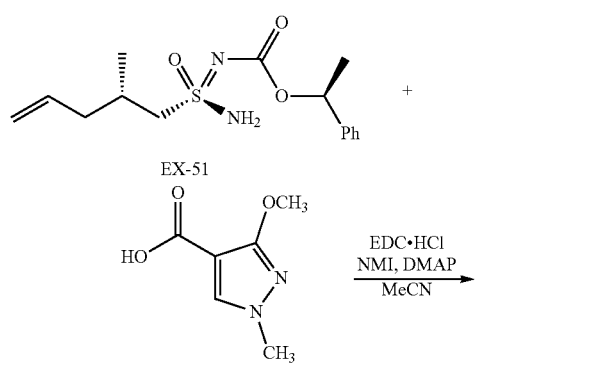

nopyridine (1.0 equiv), and acetonitrile (15 volumes). To this mixture was charged 1-methylimidazole (3.0 equiv) and N-(3-dimethylaminopropyl)-N'-ethylcarbodiimide hydrochloride (1.3 equiv), and the contents were agitated at about 20° C. for about 20 h. Dichloromethane (15 volumes) and 10% (w/w) aqueous citric acid (12 volumes) were charged to the vessel, and the layers were separated. The aqueous layer was washed with dichloromethane (15 volumes), and the layers were separated. Concentrated the combined organic layers under reduced pressure, then charged 2-methyltetrahydrofuran (20 volumes). Agitated the contents at about 60° C., then charged 10% (w/w) aqueous citric acid (12 volumes). Agitated the contents at about 60° C. for about 48 h, then separated the layers. The aqueous layer was washed with 2-methyltetrahydrofuran (10 volumes), and the layers were separated. The combined organic layers were dried over sodium sulfate and concentrated. The crude product was purified by chromatography using ethyl acetate and hexanes to afford EX-136. ¹H NMR (400 MHz, Chloroform-d) δ 7.72 (s, 1H), 5.80-5.60 (m, 1H), 5.15-4.99 (m, 2H), 3.98 (s, 3H), 3.73 (s, 3H), 3.50 (dd, J=14.3, 5.0 Hz, 1H), 3.22 (dd, J=14.3, 7.2 Hz, 1H), 2.38-2.07 (m, 3H), 1.13 (d, J=6.7 Hz, 3H).

Amide Coupling of EX-60 and EX-136 to EX-73:

Step 2:

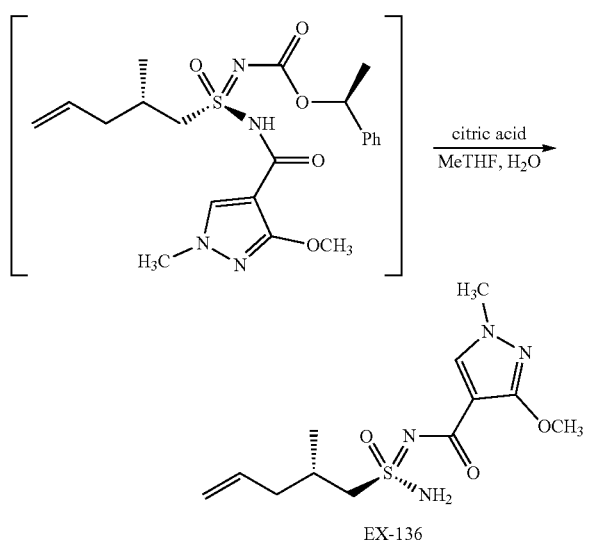

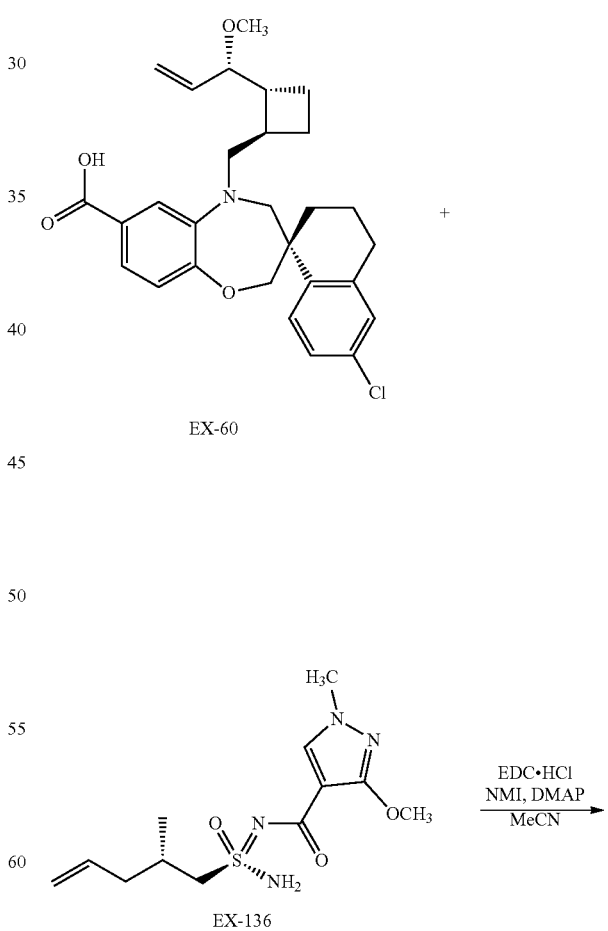

An inert reaction vessel was charged with EX-51 (1.0 equiv, scaling factor), EX-72 (1.06 equiv), 4-dimethylami- -continued

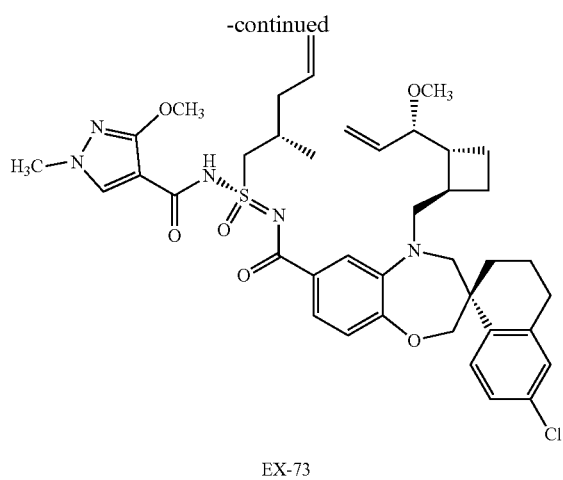

EX-73

An inert reaction vessel was charged with EX-60 (1.0 equiv, scaling factor), EX-136 (1.06 equiv), 4-dimethylaminopyridine (1.0 equiv), and acetonitrile (10 volumes). To this mixture was charged 1-methylimidazole (3.0 equiv) and N-(3-dimethylaminopropyl)-N'-ethylcarbodiimide hydrochloride (1.3 equiv), and the contents were agitated at about 20° C. for about 24 h. Ethyl acetate (10 volumes) and 10% (w/w) aqueous citric acid (10 volumes) were charged to the vessel, and the layers were separated. The crude product was carried forward to Compound 1 utilizing the Ring-Closing Metathesis of EX-73 to Compound 1 and matched authentic material.

Esterification of EX-137 to EX-138:

An inert reaction vessel was charged with EX-137 (1.0 equiv, scaling factor), ethanol (5 volumes, and sulfuric acid (0.02 volumes). The resulting mixture was then warmed to about 80° C. and stirred overnight. The reaction mixture was concentrated to dryness under vacuum. The residue was then diluted with methyl tert-butyl ether (2 volumes) followed by the addition of a saturated solution of aqueous sodium bicarbonate (2 volumes). The layers were separated, the aqueous layer was backextracted with methyl tert-butyl ether (2 volumes), and the combined organic layers were washed with a 15 wt % aqueous solution of sodium chloride (2 volumes). The layers were separated, and the organic layer was over sodium sulfate. The drying agent was removed via filtration then the filtrate was concentrated to afford EX-138. $^1$H NMR (400 MHz, chloroform-d) δ 4.20-4.09 (m, 4H), 3.41-3.36 (m, 2H), 2.19-2.16 (m, 4H), 1.59-1.18 (m, 6H)

Enzymatic Hydrolysis of EX-138 to EX-139:

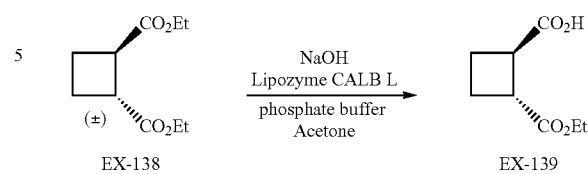

A reactor was charged with EX-138 (1.0 equiv, scaling factor), acetone (4 volumes), 0.1 M pH 7 phosphate buffer (20 volumes), and Lipozyme CALB L (0.05 volumes). The reaction mixture was warmed to about 30° C. and the pH was maintained between 7.0-7.5 via the addition of 1 N NaOH. After about 4 h, the reaction mixture was diluted with dichloromethane (10 volumes) and acidified with 1 M aqueous HCl (5 volumes). The layers were separated, and the aqueous layer was back-extracted with dichloromethane (10 volumes). The organic layers were combined and dried over sodium sulfate. The drying agent was removed via filtration then the filtrate was concentrated to dryness under vacuum affording EX-139. $^1$H NMR (400 MHz, DMSO-d6) δ 12.31 (s, 1H), 4.07 (q, J=7.1 Hz, 2H), 3.30-3.16 (m, 2H), 2.15-1.94 (m, 4H), 1.17 (t, J=7.1 Hz, 3H).

Reduction of EX-139 to EX-140:

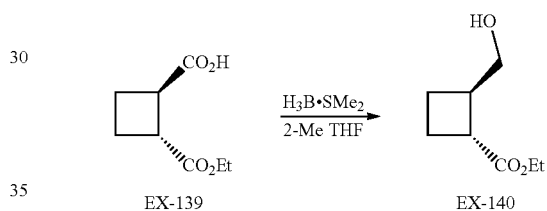

To 2-methyltetrahydrofuran (10 volumes) was added borane dimethylsulfide complex (1.5 equiv) and the resulting solution was cooled to about 0° C. followed by the addition of a solution of EX-139 (1.0 equiv, scaling factor) in 2-methyltetrahydrofuran (5 volumes) at such a rate to maintain the internal temperature below about 10° C. Once the addition was complete, the reaction mixture was warmed to about room temperature and stirred for about 2 h. The reaction mixture was quenched by the slow addition of methanol (10 volumes) The resulting solution was concentrated to dryness and the resulting material was diluted with methanol (10 volumes). The solution was concentrated to dryness and diluted with methanol (10 volumes). The solution was concentrated to dryness to afford EX-140. $^1$H NMR (400 MHz, chloroform-d) δ 4.14 (qd, J=7.1, 0.7 Hz, 2H), 3.63 (qd, J=10.9, 6.2 Hz, 2H), 2.95-2.87 (m, 1H), 2.77-2.66 (m, 1H), 2.28-2.12 (m, 1H), 2.12-2.02 (m, 1H), 2.00-1.84 (m, 2H), 1.72 (ddt, J=11.1, 10.1, 9.0 Hz, 1H), 1.25 (t, J=7.2 Hz, 3H).

Silyl Protection of EX-140 to EX-141:

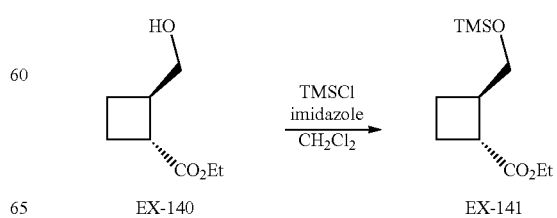

An inert reaction vessel was charged with EX-140 (1.0 equiv, scaling factor) and dichloromethane (10 volumes), and the mixture was cooled to about 0° C. To this mixture was charged imidazole (2.5 equiv) and tert-butyldimethylsilyl chloride (1.2 equiv), and the contents were agitated for about 17 h while warming to about 20° C. Dichloromethane (10 volumes) and water (10 volumes) were charged to the vessel, and the layers were separated. Water (10 volumes) was charged to the organic layer, and the layers were separated. The organic layer was dried with sodium sulfate and concentrated to give EX-141. $^1$H NMR (400 MHz, Chloroform-d) δ 4.11 (q, J=7.1 Hz, 2H), 3.65-3.52 (m, 2H), 2.95 (qd, J=8.8, 0.9 Hz, 1H), 2.78-2.61 (m, 1H), 2.21-1.98 (m, 2H), 1.89-1.77 (m, 2H), 1.24 (t, J=7.1 Hz, 3H), 0.90 (s, 9H), 0.05 (s, 6H).

Kulinkovich Cyclopropanation of EX-141 to EX-142:

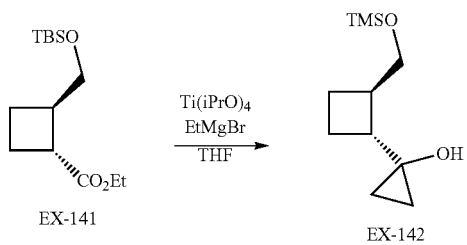

An inert reaction vessel was charged with EX-141 (1.0 equiv, scaling factor) and THF (10 volumes), and the mixture was cooled to about 0° C. To this mixture was charged titanium(IV) isopropoxide (1.0 equiv) followed by a 40 wt % solution of ethylmagnesium bromide in 2-MeTHF (3.0 equiv), and the contents were agitated for about 17 h while warming to about 20° C. A 20 wt % solution of citric acid in water (6.5 volumes) and a 25 wt % solution of ammonium chloride in water (6.5 volumes) were combined and charged to the vessel, and the layers were separated. MTBE (22 volumes) was charged to the aqueous layer, and the layers were separated. A 15 wt % solution of sodium chloride in water (6.5 volumes) was charged to the combined organic layers, and the layers were separated. The organic layer was dried with sodium sulfate and concentrated to give EX-142. $^1$H NMR (400 MHz, Chloroform-d) δ 3.70 (dd, J=9.7, 4.5 Hz, 1H), 3.45 (t, J=9.9 Hz, 1H), 2.61-2.51 (m, 1H), 2.38-2.24 (m, 1H), 1.81-1.66 (m, 2H), 1.57-1.41 (m, 1H), 1.23 (qd, J=10.0, 8.4 Hz, 1H), 0.90 (s, 9H), 0.74 (ddd, J=10.8, 6.3, 5.1 Hz, 1H), 0.66-0.52 (m, 2H), 0.37 (ddd, J=10.4, 6.7, 5.1 Hz, 1H), 0.09 (d, J=1.1 Hz, 6H).

Protection of EX-143 to EX-144:

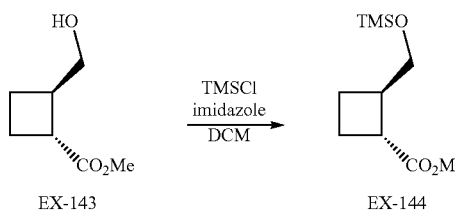

To a reactor was charged EX-143 (1.0 equiv, scaling factor) and dichloromethane (8 volumes). The resulting mixture was cooled to about 0° C. and imidazole (2.5 equiv) and tert-butyldimethylchlorosilane (1.2 equiv) were charged. The reaction mixture was agitated for about 12 h, then water (10 volumes) and dichloromethane (8 volumes) were charged. The layers were separated, and the organic layer was washed with water (10 volumes). The layers were separated and the organic later was dried over sodium sulfate, filtered, and concentrated to give EX-144. $^1$H NMR (400 MHz, CDCl$_3$): δ 3.16 (s, 3H), 3.59-3.49 (m, 2H), 2.96-2.92 (m, 1H), 2.70-2.59 (m, 1H), 2.13-1.94 (m, 2H), 1.86-1.71 (m, 2H), 0.85 (s, 9H), 0.01 (s, 6H)

Kulinkovich Cyclopropanation of EX-144 to EX-142:

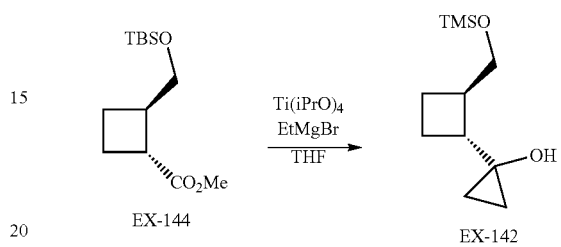

A reactor was charged with EX-144 (1.0 equiv, scaling factor) and tetrahydrofuran (11 volumes) and cooled to about 0° C. Titanium(IV) isopropoxide (1.0 equiv) was charged to the mixture followed by 40 wt % ethylmagnesium bromide in 2-methyltetrahydrofuran (3.0 equiv) which was added over about 1 h at about 0° C. The mixture was warmed to about 22° C. and quenched with 25 wt % aqueous ammonium chloride solution (6 volumes) followed by 20 wt % citric acid solution (6 volumes). The aqueous layer was removed and back-extracted with methyl tert-butyl ether (22 volumes). The organic layers were combined, washed with 15 wt % aqueous sodium chloride solution (7 volumes), dried over sodium sulfate, filtered, and concentrated to afford EX-142. $^1$H NMR (400 MHz, Chloroform-d) δ 3.70 (dd, J=9.7, 4.5 Hz, 1H), 3.45 (t, J=9.9 Hz, 1H), 2.61-2.51 (m, 1H), 2.38-2.24 (m, 1H), 1.81-1.66 (m, 2H), 1.57-1.41 (m, 1H), 1.23 (qd, J=10.0, 8.4 Hz, 1H), 0.90 (s, 9H), 0.74 (ddd, J=10.8, 6.3, 5.1 Hz, 1H), 0.66-0.52 (m, 2H), 0.37 (ddd, J=10.4, 6.7, 5.1 Hz, 1H), 0.09 (d, J=1.1 Hz, 6H).

Synthesis of EX-145 from EX-142:

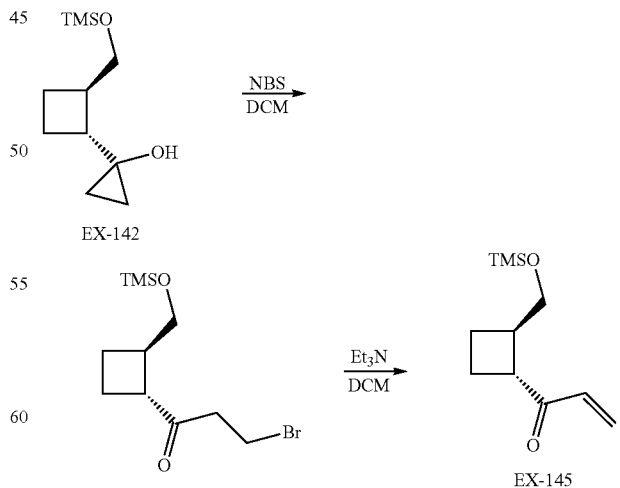

A reactor was charged with EX-142 (1.0 equiv, scaling factor) in dichloromethane (8 volumes) and cooled to about 0° C. N-Bromosuccinimide (1.05 equiv) was charged in one portion and agitated for about 1.5 h at about 0° C. Triethylamine (2.0 equiv) was charged at 0° C. and agitated for about 2.5 h at about 0° C. The reaction mixture was quenched with 20 wt % citric acid solution (6 volumes) and warmed to about 20° C. The layers were separated and the organic layer was washed with 5 wt % sodium bicarbonate solution (8 volumes) followed by 15 wt % aqueous sodium chloride solution (15 volumes), dried over magnesium sulfate, filtered, then concentrated to afford EX-145. $^1$H NMR (400 MHz, CDCl$_3$) δ 6.27-6.36 (m, 1H), 6.22-6.13 (m, 1H), 5.75-5.70 (m, 1H), 3.61-3.51 (m, 2H), 3.43-3.33 (m, 1H), 2.66-2.55 (m, 1H), 2.18-2.07 (m, 1H), 2.00-1.91 (m, 1H), 1.85-1.76 (m, 2H), 0.85 (s, 9H), 0.01 (s, 6H).

Ketoreductase Reduction of EX-145 to EX-146:

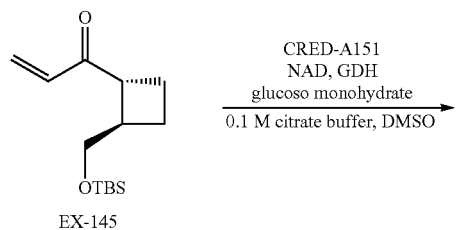

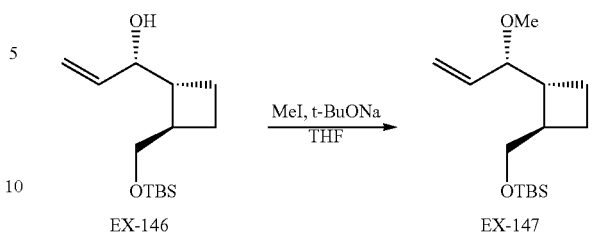

A reaction vessel was charged with NAD (1.0 wt %), GDH (2.0 wt %), glucose monohydrate (1.2 equiv), 0.1 M aqueous citrate buffer at pH 6.2 (17 volumes), and a solution of EX-145 (1.0 equiv) in DMSO (2 volumes). To this mixture was charged CRED-A151 (50 wt %), and the contents were agitated at about 30° C. for about 14 h. Additional NAD (0.2 wt %), GDH (0.4 wt %), and CRED-A151 (10 wt %) were charged to the vessel, and the contents were agitated for about 9 h. 1 M aqueous citrate buffer at pH 3.6 was charged to the vessel to adjust the pH of the contents to about 4.5, and then the contents were cooled to about 4° C. Saturated aqueous sodium chloride (20 volumes) and MTBE (120 volumes) were charged to the vessel, and the layers were separated. The organic layer was filtered through Celite. Saturated aqueous sodium chloride (20 volumes) was charged to the organic layer, and the layers were separated; this was repeated once more. The organic layer was dried with magnesium sulfate and concentrated to give EX-146. $^1$H NMR (400 MHz, Chloroform-d) δ 5.72 (ddd, J=17.0, 10.4, 6.5 Hz, 1H), 5.24 (ddd, J=17.1, 2.0, 1.2 Hz, 1H), 5.07 (ddd, J=10.4, 1.9, 1.0 Hz, 1H), 3.94-3.81 (m, 2H), 3.70 (dd, J=9.6, 4.4 Hz, 1H), 3.38 (dd, J=10.7, 9.6 Hz, 1H), 2.39-2.22 (m, 1H), 2.09-1.95 (m, 1H), 1.91-1.75 (m, 2H), 1.70-1.41 (m, 2H), 0.91 (s, 9H), 0.09 (s, 6H).

Methylation of EX-146 to EX-147:

An inert reaction vessel was charged with EX-146 (1.0 equiv, scaling factor) and THF (10 volumes), and the mixture was cooled to about 0° C. To this mixture was charged sodium tert-butoxide (3.0 equiv) and iodomethane (6.0 equiv), and the contents were agitated at about 0° C. for about 2 h. Triethylamine (7.6 equiv) was charged to the vessel, and the contents were agitated at about 0° C. for about 1 h. MTBE (20 volumes) and water (20 volumes) were charged to the vessel, and the layers were separated. MTBE (20 volumes) was charged to the aqueous layer, and the layers were separated. A 15 wt % solution of sodium chloride in water (20 volumes) was charged to the combined organic layers, and the layers were separated. The organic layer was dried with magnesium sulfate and concentrated to provide EX-147. $^1$H NMR (400 MHz, Chloroform-d) δ 5.61 (ddd, J=16.6, 10.8, 7.8 Hz, 1H), 5.23-5.13 (m, 2H), 3.64 (dd, J=10.2, 4.9 Hz, 1H), 3.52 (dd, J=10.2, 6.8 Hz, 1H), 3.44 (t, J=7.5 Hz, 1H), 3.26 (s, 3H), 2.38-2.24 (m, 1H), 2.22-2.10 (m, 1H), 1.94-1.81 (m, 1H), 1.84-1.72 (m, 1H), 1.72-1.58 (m, 2H), 0.90 (s, 9H), 0.04 (s, 6H).

Deprotection of EX-147 to EX-148:

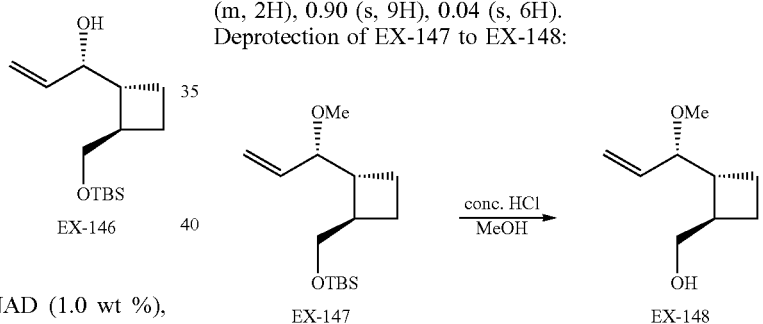

An inert reaction vessel was charged with EX-147 (1.0 equiv, scaling factor) and methanol (10 volumes). To this mixture was charged concentrated HCl (3.0 equiv), and the contents were agitated at about 22° C. for about 3 h. Saturated aqueous sodium bicarbonate (12 volumes) and dichloromethane (12 volumes) were charged to the vessel, and the layers were separated. Dichloromethane (12 volumes) was charged to the aqueous layer, and the layers were separated; this was repeated once more. The combined organic layers were dried with magnesium sulfate and concentrated to give EX-148. $^1$H NMR (400 MHz, Chloroform-d) δ 5.53 (ddd, J=16.4, 11.2, 8.2 Hz, 1H), 5.35-5.21 (m, 2H), 3.61 (dd, J=10.4, 4.3 Hz, 1H), 3.44-3.34 (m, 2H), 3.32 (s, 3H), 2.34 (qd, J=12.6, 12.2, 9.2 Hz, 1H), 2.14-1.96 (m, 1H), 1.94-1.75 (m, 2H), 1.67-1.48 (m, 2H).

Although the foregoing disclosure has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each

What is claimed is:
1. A compound selected from:
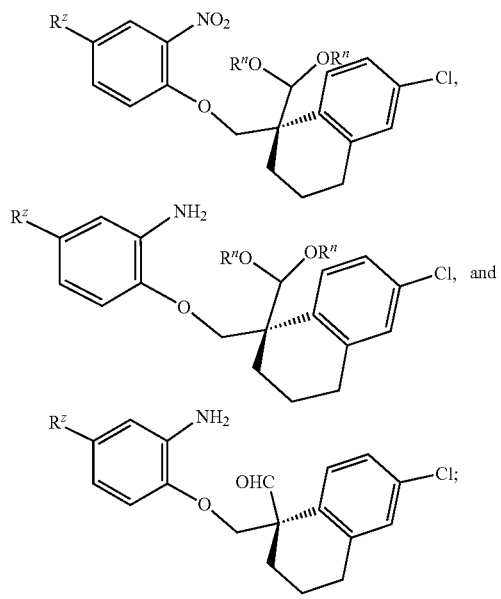
wherein
each $R''$ is independently $C_{1-6}$alkyl, or the two $R''$ moieties join together to form a $C_{2-4}$alkyl bridge, wherein the bridge is optionally substituted by one to four groups independently selected from $C_{1-3}$alkyl and phenyl; and
$R^z$ is halogen or CN.
2. The compound of claim 1 selected from:
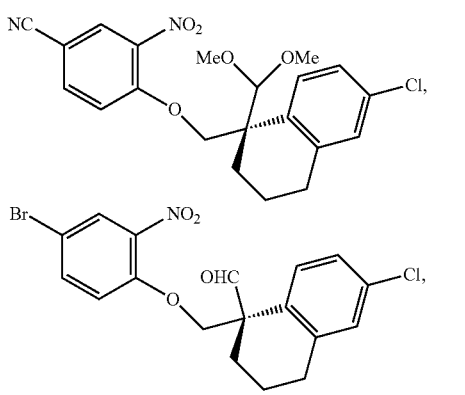
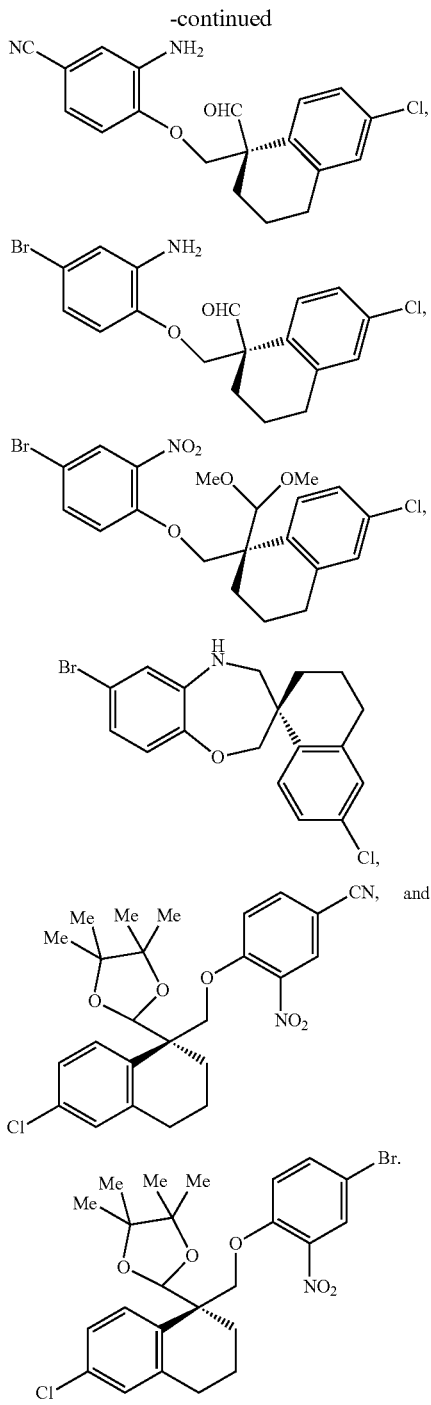
* * * * *